United States Patent
Reche-Gallardo et al.

(10) Patent No.: US 8,075,886 B2
(45) Date of Patent: Dec. 13, 2011

(54) METHOD OF TREATMENT USING AN ANTI-IL-B50 ANTIBODY

(75) Inventors: Pedro A. Reche-Gallardo, Boston, MA (US); Vassili Soumelis, Paris (FR); Yong-Jun Liu, Pearland, TX (US); Rene de Waal Malefyt, Sunnyvale, CA (US); J. Fernando Bazan, Menlo Park, CA (US); Robert A. Kastelein, Portola Valley, CA (US)

(73) Assignee: Schering Corp, Kenilworth, NJ (US)

(*) Notice: Subject to any disclaimer, the term of this patent is extended or adjusted under 35 U.S.C. 154(b) by 0 days.

(21) Appl. No.: 12/493,871

(22) Filed: Jun. 29, 2009

(65) Prior Publication Data

US 2009/0275135 A1 Nov. 5, 2009

Related U.S. Application Data

(62) Division of application No. 11/297,957, filed on Dec. 9, 2005, now Pat. No. 7,569,224, which is a division of application No. 10/927,228, filed on Aug. 25, 2004, now Pat. No. 7,071,308, which is a division of application No. 10/008,566, filed on Nov. 8, 2001, now Pat. No. 6,890,734.

(60) Provisional application No. 60/298,268, filed on Jun. 14, 2001, provisional application No. 60/247,218, filed on Nov. 10, 2000.

(51) Int. Cl.
*A61K 39/395* (2006.01)

(52) U.S. Cl. .............. 424/130.1; 424/139.1; 424/158.1

(58) Field of Classification Search .................. None
See application file for complete search history.

(56) References Cited

U.S. PATENT DOCUMENTS

| | | | |
|---|---|---|---|
| 5,194,375 A | 3/1993 | Park et al. | |
| 6,555,520 B2 | 4/2003 | Sims et al. | |
| 6,844,170 B1 | 1/2005 | Moore et al. | |
| 6,861,227 B2 | 3/2005 | Ruben et al. | |
| 6,890,734 B2 | 5/2005 | Reche-Gallardo et al. | |
| 6,955,895 B2 | 10/2005 | Pandey et al. | |
| 6,982,320 B2 | 1/2006 | Moore et al. | |
| 7,071,308 B2 | 7/2006 | Reche-Gallardo et al. | |
| 7,304,144 B2 | 12/2007 | Sims et al. | |
| 7,405,058 B2 | 7/2008 | Sims et al. | |
| 7,504,105 B2 | 3/2009 | Ruben et al. | |
| 2002/0068323 A1 | 6/2002 | Saris et al. | |
| 2003/0186875 A1 | 10/2003 | De Waal Malefyt et al. | |
| 2004/0091970 A1 | 5/2004 | Bazan et al. | |
| 2007/0048781 A1 | 7/2007 | Bazan et al. | |

FOREIGN PATENT DOCUMENTS

| | | | |
|---|---|---|---|
| EP | 1129190 | 5/2007 | |
| WO | WO 99/47538 | 9/1999 | |
| WO | WO 00/17362 | 3/2000 | |
| WO | WO 00/29581 | * 5/2000 | |
| WO | WO 01/12672 | 2/2001 | |
| WO | WO 02/00724 | 1/2002 | |
| WO | WO 02/068588 | 9/2002 | |

OTHER PUBLICATIONS

Chuntharapai et al (1997), Methods in Enzymology, vol. 288, pp. 15-27.*
Akashi, et al., "Lymphoid precursors", Curr Opin Immunol, 12(2)144-150, Apr. 2000.
Aspinall, et al., "Thymic atrophy in the mouse is a sluble problem of the thymic environment," Vaccine, 18(16):1629-1637, Feb. 25, 2000.
Beverly, et al., "Is immune senescence reversible?", Vaccine, 18(16):1721-1724, Feb. 25, 2000.
Bolin, et al., "HNMP-1: a novel hematopoietic and neural membrane protein differentially regulated in neural development and injury", J. Neurosci, 17(14):5493-5502, Jul. 15, 1997.
Fehniger, et al., "Differential cytokine and chemokine gene expression by human NK cells following activation with Il-15 in combination with IL-12; implications for the innate immune response", J. Immunol, 162(8):4511-4520, Apr. 15, 1999.
Kadowaki, et al., "Natural interferon alpha/beta-producing cells link innate and adaptive immunity," J. Exp. Med., 192(2):219-226, Jul. 17, 2000.
Katz, et al., "Streptavidin-binding and -dimerizing ligands discovered by phage display, topochemistry, and structure-based design" Biomol Eng., 16(1-4):57-65, Dec. 31, 1999.
Kelleher, et al., "Functions of tetramer-stained HIV-specific CD4(+) and CD8(+) T cells", Curr. Opin. Immunol., 12(4):370-374, Aug. 2000.
Kitmura, "New experimental approaches in retrovirus-mediated expression screening", Int. J. Hematol., 67(4): 351-359, Jun. 1998.
Koppelman, et al., "Interleukin-10 down-regulates MHC class II alphabeta peptide complexes at the plasma membrane of moncytes by affecting arrival and recycling", Immunity, 7(6):861-871, Dec. 1997.
Levin, et al., "Thymic stromal lymphopoeitin (TSLP): A cytokine that promotes the development of IgM+B cells in vitro and signals via a novel mechanism", FASEB Journal, vol. 13, No. 4, Part 1, Mar. 12, 1999, p. A322 XP008014578, Annual Meeting of the Professional Research Scientists for Experimental Biology 99, Washington DC, USA, Apr. 17-21, 1999 ISSN 0892-6638, the whole document.
Ogg, et al., "HLA-peptide tetrameric complexes", Curr. Opin. Immunol., 10(4):393-396, Aug. 1998. Pandey, et al., "Cloning of a receptor subunit required for signaling by thymic stromal lymphopoietin", Nature Immunology, vol. 1, No. 1, pp. 59-64, Jul. 2000.
Park, et al., "Cloning of the murine thymic stromal lymphopoietin (TSLP) receptor: Formation of a functional heteromeric complex requires interleukin 7 receptor", J. Exp. Med., 192(5):659-670, Sep. 4, 2000.
Puel, et al., "Mutations in the gene for the IL-7 receptor result in T(−)B(+)NK(+) severe combined immunodeficiency disease", Curr. Opin. Immunol., 12(4):468-73, Aug. 2000.
Sims, et al., "Molecular cloning and biological characterization of a novel murine lymphoid growth factor", J. Exp. Med., 192(5):671-680, Sep. 4, 2000.
Stoddart, et. al., "The role of the preBCR, the interleukin-7 receptor, and homotypic interactions during B-cell development", Immunol. Rev. 175:47-58, Jun. 2000.
Waldmann, et al., "T-cell receptors for cytokines: targets for immunotherapy of leukemia/lymphoma", Ann. Oncol. 11 Suppl. 1:101-106, 2000.

(Continued)

Primary Examiner — Prema Mertz

(57) ABSTRACT

Nucleic acids encoding mammalian cytokine receptor, e.g., for cytokine IL-B50, purified proteins and fragments thereof. Antibodies, both polyclonal and monoclonal, are also provided. Methods of using the compositions for both diagnostic and therapeutic utilities are described.

4 Claims, 35 Drawing Sheets

OTHER PUBLICATIONS

U.S. Appl. No. 12/174,871, Jul. 17, 2008, Bazan et al.
U.S. Appl. No. 12/174,889, Jul. 17, 2008, Bazan et al.
Soumelis, V., et al., Human epithelial cells trigger dendritic cell-mediated allergic inflammation by producing TSLP, Nature Immunology, vol. 3, No. 7, pp. 673-680, 2002.
Hammad, H., et al., "Th2polarization by Der p 1-pulsed monocyte-derived dendritic cells is due to the allergic status of the donors", Blood, vol. 98, No. 4, pp. 1135-1141 (2001).
Mosmann, T.R., "Th1 and Th2 Cells: Different Patterns of Lymphokine Secretion Lead to Different Functional Properties", Ann. Rev. Immunol., vol. 7, pp. 145-173 (1989).
Novak, N., "Dendritic cells in allergy", Allergy, vol. 54, pp. 792-803 (1999).
Reche, P., "Human Thymic Stromal Lymphopoietin Preferentially Stimulates Myeloid Cells", The Journal of Immunology, vol. 167, pp. 336-343 (2001).
Li, Y., "Thymic Stromal Lymphopoietin Promotes Lung Inflammation Through Activation of Dendritic Cells", Journal of Asthma, vol. 47, p. 117-123 (2010).

* cited by examiner

Nucleotide and amino acid sequences (see SEQ ID NO: 1 and 2) of a primate, e.g., human, IL-7Rα; predicted signal cleavage site indicated.

```
ctctctctct atctctctca ga atg aca att cta ggt aca act ttt ggc atg         52
                         Met Thr Ile Leu Gly Thr Thr Phe Gly Met
                                            -20              -15 gtt ttt tct tta ctt caa gtc gtt tct gga gaa agt ggc tat gct caa         100
Val Phe Ser Leu Leu Gln Val Val Ser Gly Glu Ser Gly Tyr Ala Gln
-10                  -5                    -1   1               5 aat gga gac ttg gaa gat gca gaa ctg gat gac tac tca ttc tca tgc         148
Asn Gly Asp Leu Glu Asp Ala Glu Leu Asp Asp Tyr Ser Phe Ser Cys
            10                      15                      20 tat agc cag ttg gaa gtg aat gga gtg aac tcg cag cat tca ctg gaa acc tgt gct         196
Tyr Ser Gln Leu Glu Val Asn Gly Val Asn Ser Gln His Ser Leu Thr Cys Ala
                25                          30                      35 ttt gag gac cca gat gtc aac acc aat ctg gaa ttt gaa ata tgt         244
Phe Glu Asp Pro Asp Val Asn Thr Asn Leu Glu Phe Glu Ile Cys
    40                      45                      50 ggg gcc ctc gtg gag gta aag tgc ctg aat ttc agg aaa cta caa gag         292
Gly Ala Leu Val Glu Val Lys Cys Leu Asn Phe Arg Lys Leu Gln Glu
55                      60                      65              70
```

FIG. 1A

| | | | | | | | | | | |
|---|---|---|---|---|---|---|---|---|---|---|
| ata | tat | ttc | atc | gag | aca | aag | aaa | ttc | tta | ctg | att | gga | aag | agc | aat | 340 |
| Ile | Tyr | Phe | Ile | Glu | Thr | Lys | Lys | Phe | Leu | Leu | Ile | Gly | Lys | Ser | Asn |
| | | | | 75 | | | | | 80 | | | | | 85 | |

```
ata tat ttc atc gag aca aag aaa ttc tta ctg att gga aag agc aat   340
Ile Tyr Phe Ile Glu Thr Lys Lys Phe Leu Leu Ile Gly Lys Ser Asn
                75                  80                  85 ata tgt gtg aag gtt gga gaa aag agt cta acc tgc aaa aaa ata gac   388
Ile Cys Val Lys Val Gly Glu Lys Ser Leu Thr Cys Lys Lys Ile Asp
                90                  95                 100 cta act act ata gtt aaa cct gag gct cct ttt gac ctg agt gtc atc   436
Leu Thr Thr Ile Val Lys Pro Glu Ala Pro Phe Asp Leu Ser Val Ile
               105                 110                 115 tat cgg gaa gga gcc aat gac ttt gtg gtg aca ttt aat aca tca cac   484
Tyr Arg Glu Gly Ala Asn Asp Phe Val Val Thr Phe Asn Thr Ser His
               120                 125                 130 ttg caa aag aag tat gta aaa gtt tta atg cat gat gta gct tac cgc   532
Leu Gln Lys Lys Tyr Val Lys Val Leu Met His Asp Val Ala Tyr Arg
               135                 140                 145                 150 cag gaa aag gat gaa aac aaa tgg acg cat gtg aat tta tcc agc aca   580
Gln Glu Lys Asp Glu Asn Lys Trp Thr His Val Asn Leu Ser Ser Thr
               155                 160                 165
```

FIG. 1B

| | | | | | | | | | | |
|---|---|---|---|---|---|---|---|---|---|---|
| aag | ctg | aca | ctc | ctg | cag | aga | aag | ctc | caa | ccg | gca | atg | tat | gag | 628 |
| Lys | Leu | Thr | Leu | Leu | Gln | Arg | Lys | Leu | Gln | Pro | Ala | Met | Tyr | Glu | |
| | | 170 | | | | | 175 | | | | | 180 | | | | att gtc cga tcc atc cct gat cac tat ttt aaa ggc ttc tgg agt 676
Ile Val Arg Ser Ile Pro Asp His Tyr Phe Lys Gly Phe Trp Ser
            185                         190                         195 gaa tgg agt cca agt tat tac ttc aga act cca gag atc aat agc 724
Glu Trp Ser Pro Ser Tyr Tyr Phe Arg Thr Pro Glu Ile Asn Ser
            200                         205                         210 tca ggg gag atg gat cct atc tta cta acc atc agc att ttg agt ttt 772
Ser Gly Glu Met Asp Pro Ile Leu Leu Thr Ile Ser Ile Leu Ser Phe
            215                         220                         225                         230 ttc tct gtc gct ctg ttg gtg atc ttg gcc tgt gtg tta tgg aaa aaa 820
Phe Ser Val Ala Leu Leu Val Ile Leu Ala Cys Val Leu Trp Lys Lys
            235                         240                         245 agg att aag cct atc gta tgg ccc agt ctc gat cat aag act 868
Arg Ile Lys Pro Ile Val Trp Pro Ser Leu Pro Asp His Lys Lys Thr
            250                         255                         260 ctg gaa cat ctt tgt aag cca aga aaa aat tta aat gtg agt ttc 916
Leu Glu His Leu Cys Lys Pro Arg Lys Asn Leu Asn Val Ser Phe
            265                         270                         275

FIG. 1C

```
aat cct gaa agt ttc ctg gac tgc cag att cat agg gtg gat gac att    964
Asn Pro Glu Ser Phe Leu Asp Cys Gln Ile His Arg Val Asp Asp Ile
        280                 285                 290 caa gct aga gat gaa gtg gaa ggt ttt ctg caa gat acg ttt cct cag   1012
Gln Ala Arg Asp Glu Val Glu Gly Phe Leu Gln Asp Thr Phe Pro Gln
    295                 300                 305                 310 caa cta gaa gaa tct gag aag cag agg ctt gga ggg gat gtg cag agc   1060
Gln Leu Glu Glu Ser Glu Lys Gln Arg Leu Gly Gly Asp Val Gln Ser
        315                 320                 325 ccc aac tgc cca tct gag gat gta gtc gtc act cca gaa agc ttt gga   1108
Pro Asn Cys Pro Ser Glu Asp Val Val Thr Pro Glu Ser Phe Gly
        330                 335                 340 aga gat tca tcc ctc aca tgc ctg gct ggg aat gtc agt gca tgt gac   1156
Arg Asp Ser Ser Leu Thr Cys Leu Ala Gly Asn Val Ser Ala Cys Asp
    345                 350                 355 gcc cct att ctc tcc tct agg tcc cta gac tgc agg gag agt ggc       1204
Ala Pro Ile Leu Ser Ser Arg Ser Leu Asp Cys Arg Glu Ser Gly
        360                 365                 370 aag aat ggg cct cat gtg tac cag gac ctc ctg agc ctt ggg act       1252
Lys Asn Gly Pro His Val Tyr Gln Asp Leu Leu Ser Leu Gly Thr
    375                 380                 385                 390
```

FIG. 1D

```
aca aac agc acg ctg ccc cct cca ttt tct ctc caa tct ctg gga atc ctg    1300
Thr Asn Ser Thr Leu Pro Pro Pro Phe Ser Leu Gln Ser Gly Ile Leu
                     395                             400             405 aca ttg aac cca gtt gct cag ggt cag ccc att ctt act tcc ctg gga        1348
Thr Leu Asn Pro Val Ala Gln Gly Gln Pro Ile Leu Thr Ser Leu Gly
         410                             415                     420 tca aat caa gaa gaa gca tat gtc acc atg tcc agc ttc tac caa aac        1396
Ser Asn Gln Glu Glu Ala Tyr Val Thr Met Ser Ser Phe Tyr Gln Asn
             425                             430                 435 cag tgaagtgtaa gaaacccaga ctgaacttac cgtgagcgac aaagatgatt             1449
Gln taaaagggaa gtctagagtt cctagtctcc ctcacagcac agagaagaca aaattagcaa      1509
aaccccacta cacagtctgc aagattctga aacattgctt tgaccactct tcctgagttc      1569
agtggcactc aacatgagtc aagagcatcc tgcttctacc atgtggattt ggtcacaagg      1629
tttaaggtga cccaatgatt cagctattt                                        1658
```

FIG. 1E

Nucleotide and amino acid sequences (see SEQ ID NO: 3 and 4) of a primate, e.g., human, Rδ2; predicted signal cleavage site indicated.

```
cggcacgagg gc atg ggg cgg ctg gtt ctg tgg gga gct gcc gtc ttt          51
           Met Gly Arg Leu Val Leu Trp Gly Ala Ala Val Phe
               -20                  -15                -10 ctg ctg gga ggc tgg atg gct ttg ggg caa gga gca gaa gga              99
Leu Leu Gly Gly Trp Met Ala Leu Gly Gln Gly Ala Glu Gly
         -5                      -1   1            5 gta cag att cag atc atc tac ttc aat tta gaa acc gtg cag gtg aca     147
Val Gln Ile Gln Ile Ile Tyr Phe Asn Leu Glu Thr Val Gln Val Thr
         10                  15                     20 tgg aat gcc agc aaa tac tcc agg acc cgg aac ctg act ttc cac tac aga  195
Trp Asn Ala Ser Lys Tyr Ser Arg Thr Arg Asn Leu Thr Phe His Tyr Arg
         25                  30                  35 ttc aac ggt gat gag gcc tat gac cag tgc acc aac tac ctt ctc cag      243
Phe Asn Gly Asp Glu Ala Tyr Asp Gln Cys Thr Asn Tyr Leu Leu Gln
         40                  45                     50            55 gaa ggt cac act tcg ggg tgc ctc cta gac gca gag cga gac gac          291
Glu Gly His Thr Ser Gly Cys Leu Leu Asp Ala Glu Arg Asp Asp
         60                      65                  70
```

FIG. 2A

| | | | | | | | | | | | | | | | | |
|---|---|---|---|---|---|---|---|---|---|---|---|---|---|---|---|---|
| att | ctc | tat | ttc | tcc | atc | agg | aat | ggg | acg | cac | ccc | gtt | ttc | acc | gca | 339 |
| Ile | Leu | Tyr | Phe | Ser | Ile | Arg | Asn | Gly | Thr | His | Pro | Val | Phe | Thr | Ala | |
| | | | 75 | | | | | 80 | | | | | | 85 | | |
| agt | cgc | tgg | atg | gtt | tat | tac | ctg | tac | ctg | aaa | ccc | agt | ccg | aag | cac | gtg | 387 |
| Ser | Arg | Trp | Met | Val | Tyr | Tyr | Leu | Tyr | Leu | Lys | Pro | Ser | Pro | Lys | His | Val |
| | | 90 | | | | | 95 | | | | | 100 | | | | |
| aga | ttt | tcg | tgg | cat | cag | gat | gca | gtg | acg | gtg | acg | tgt | tct | gac | ctg | 435 |
| Arg | Phe | Ser | Trp | His | Gln | Asp | Ala | Val | Thr | Val | Thr | Cys | Ser | Asp | Leu | |
| | 105 | | | | | 110 | | | | | 115 | | | | | |
| tcc | tac | ggg | gat | ctc | ctc | tat | gag | gtt | cag | tac | cgg | agc | ccc | ttc | gac | 483 |
| Ser | Tyr | Gly | Asp | Leu | Leu | Tyr | Glu | Val | Gln | Tyr | Arg | Ser | Pro | Phe | Asp | |
| | 120 | | | | 125 | | | | | 130 | | | | | 135 | |
| acc | gag | tgg | cag | tcc | aaa | cag | gaa | aat | acc | tgc | aac | gtc | acc | ata | gaa | 531 |
| Thr | Glu | Trp | Gln | Ser | Lys | Gln | Glu | Asn | Thr | Cys | Asn | Val | Thr | Ile | Glu | |
| | | | 140 | | | | | 145 | | | | | 150 | | | |
| ggc | ttg | gat | gcc | gag | aag | tgt | tac | tct | ttc | tgg | gtc | agg | gtg | aag | gct | 579 |
| Gly | Leu | Asp | Ala | Glu | Lys | Cys | Tyr | Ser | Phe | Trp | Val | Arg | Val | Lys | Ala | |
| | | 155 | | | | | 160 | | | | | 165 | | | | |
| atg | gag | gat | gta | tat | ggg | cca | gac | aca | tac | cca | agc | gac | tgg | tca | gag | 627 |
| Met | Glu | Asp | Val | Tyr | Gly | Pro | Asp | Thr | Tyr | Pro | Ser | Asp | Trp | Ser | Glu | |
| | 170 | | | | | 175 | | | | | 180 | | | | | |

FIG. 2B

| | | | | | | | | |
|---|---|---|---|---|---|---|---|---|
| gtg | aca | tgc | tgg | cag | aga | ggc | gag | att | cgg | gat | gcc | tgt | gca | gag | aca | 675 |
| Val | Thr | Cys | Trp | Gln | Arg | Gly | Glu | Ile | Arg | Asp | Ala | Cys | Ala | Glu | Thr | |
| 185 | | | | | | | 190 | | | | | 195 | | | | |

| cca | acg | cct | ccc | aaa | cca | aag | ctg | tcc | aaa | ttt | att | tta | att | tcc | agc | 723 |
| Pro | Thr | Pro | Pro | Lys | Pro | Lys | Leu | Ser | Lys | Phe | Ile | Leu | Ile | Ser | Ser | |
| 200 | | | | 205 | | | | | 210 | | | | | 215 | | |

| ctg | gcc | atc | ctt | ctg | atg | gtg | tct | ctc | ctc | ctg | tct | tta | tgg | aaa | | 771 |
| Leu | Ala | Ile | Leu | Leu | Met | Val | Ser | Leu | Leu | Leu | Ser | Leu | Trp | Lys | | |
| | 220 | | | | | 225 | | | | | 230 | | | | | |

| tta | tgg | aga | gtg | aag | aag | ttt | ctc | att | ccc | agc | gtg | cca | gac | ccg | aaa | 819 |
| Leu | Trp | Arg | Val | Lys | Lys | Phe | Leu | Ile | Pro | Ser | Val | Pro | Asp | Pro | Lys | |
| | 235 | | | | | 240 | | | | | 245 | | | | | |

| tcc | atc | ttc | ccc | ggg | ctc | ttt | gag | ata | cac | caa | ggg | aac | ttc | cag | gag | 867 |
| Ser | Ile | Phe | Pro | Gly | Leu | Phe | Glu | Ile | His | Gln | Gly | Asn | Phe | Gln | Glu | |
| | | 250 | | | | | 255 | | | | | 260 | | | | |

| tgg | atc | aca | gac | acc | cag | aac | gtg | gcc | cac | ctc | cac | aag | atg | gca | ggt | 915 |
| Trp | Ile | Thr | Asp | Thr | Gln | Asn | Val | Ala | His | Leu | His | Lys | Met | Ala | Gly | |
| 265 | | | | 270 | | | | | 275 | | | | | | | |

| gca | gag | caa | gaa | agt | ggc | ccc | gag | gag | ccc | ctg | gta | gtc | cag | ttg | gcc | 963 |
| Ala | Glu | Gln | Glu | Ser | Gly | Pro | Glu | Glu | Pro | Leu | Val | Val | Gln | Leu | Ala | |
| 280 | | | | 285 | | | | | 290 | | | | | 295 | | |

FIG. 2C

```
aag act gaa gcc gag tct ccc agg atg ctg gac cca cag acc gag gag   1011
Lys Thr Glu Ala Glu Ser Pro Arg Met Leu Asp Pro Gln Thr Glu Glu
                300                 305                 310 aaa gag gcc tct ggg gga tcc ctc cag ctt ccc cac cag ccc ctc caa   1059
Lys Glu Ala Ser Gly Gly Ser Leu Gln Leu Pro His Gln Pro Leu Gln
                315                 320                 325 ggc ggt gat gtg gtc aca atc ggg ggc ttc acc ttt gtg atg aat gac   1107
Gly Gly Asp Val Val Thr Ile Gly Gly Phe Thr Phe Val Met Asn Asp
                330                 335                 340 cgc tcc tac gtg gcg ttg tgatggacac accactgtca aagtcaacgt          1155
Arg Ser Tyr Val Ala Leu
        345
```

FIG. 2D

```
caggatccac gttgacattt aaagacagag gggactgtcc cggggactcc acaccaccat   1215
ggatgggaag tctccacgcc aatgatggta ggactaggag actctgaaga cccagcctca   1275
ccgcctaatg cggccactgc cctgctaact ttcccccaca tgagtctctg tgttcaaagg   1335
cttgatggca gatgggagcc aattgctcca ggagatttac tcccagttcc ttttcgtgcc   1395
tgaacgttgt cacataaacc ccaaggcagc acgtccaaaa tgctgtaaaa ccatcttccc   1455
actctgtgag tccccagttc cctgttccat cgtccatgta cctgttccat agcattggat tctcggagga   1515 tttttgtct gttttgagac tccaaaccac ctctacccct ac                      1557
```

FIG. 2E

```
  MFPFALLYVLSVSFRKIFILQLVGLVLTYD    30
  FTNCDFEKIKAAYLSTISKDLITYMSGTKS    60
  TEFNNTVSCSNRPHCLTEIQSLTFNPTAGC    90
  ASLAKEMFAMKTKAALAIWCPGYSETQINA   120
  TQAMKKRRKRKVTTNKCLEQVSQLQGLWRR   150
  FNRPLLKQQ
```

FIG. 3A

```
  1 agtgtgaaac tggggtggaa tgggtgtcca cgtatgttcc ctttgcctt
 51 actatatgtt ctgtcagttt ctttcaggaa aatcttcatc ttacaacttg
101 tagggctggt gttaacttac gacttcacca actgtgactt tgagaagatt
151 aaagcagcct atctcagtac tatttctaaa gacctgatta catatatgag
201 tgggaccaaa agtaccgagt tcaacaacac cgtctcttgt agcaatcggc
251 cacattgcct tactgaaatc cagagcctaa ccttcaatcc caccgccggc
301 tgccgtcgc tcgccaaaga aatgttcgcc atgaaaacta aggctgcctt
351 agctatctgg tgccaggct aggagagaaa tcagataaat gctactcagg
401 caatgaagaa gaggagaaaa aggaaagtca caaccaataa atgtctggaa
451 caagtgtcac aattacaagg attgtggcgt cgcttcaatc gacccttact
501 gaaacaacag taaaccatct ttattatggt catatttcac agcaccaaaa
    ta
```

FIG. 3B

Th2
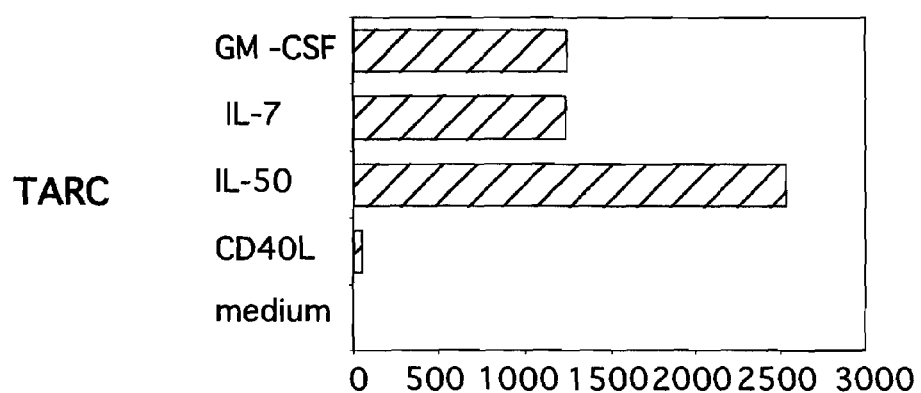
TARC
MDC
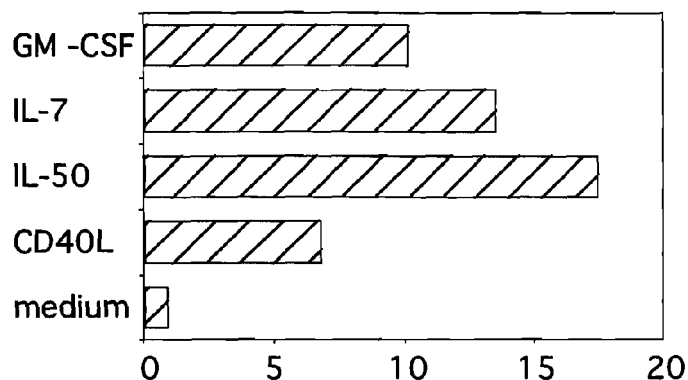
DC+Naive
MIP3-beta
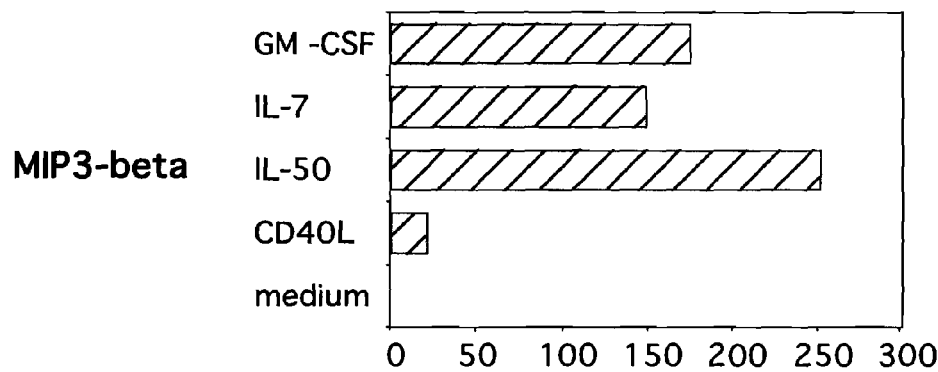
FIG. 14B

Th2+Th1
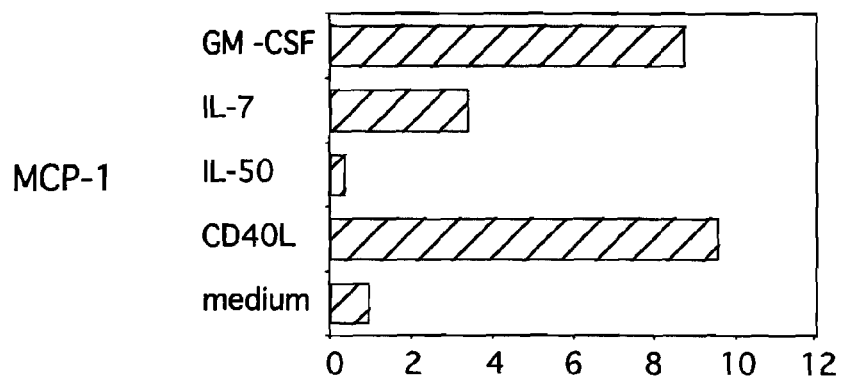
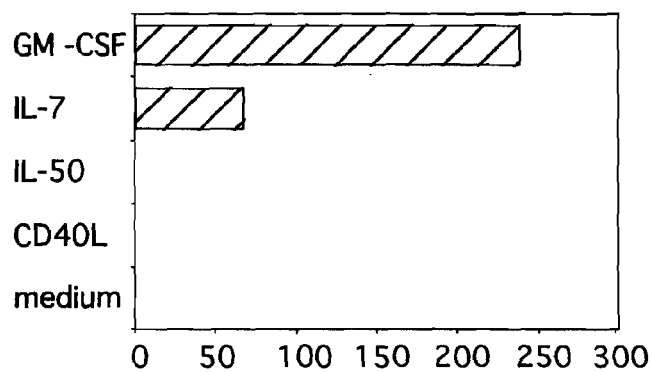
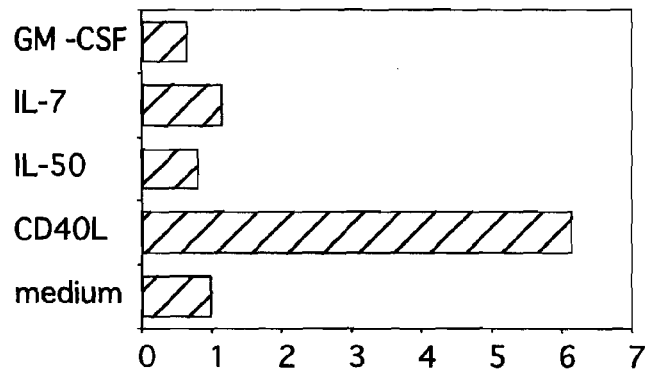
Th1
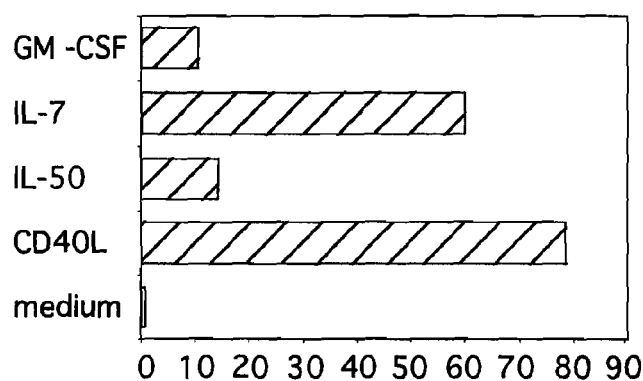
FIG. 14C

METHOD OF TREATMENT USING AN ANTI-IL-B50 ANTIBODY

This application is a divisional of U.S. patent application Ser. No. 11/297,957, filed Dec. 9, 2005, now U.S. Pat. No. 7,569,224, which is a divisional of U.S. patent application Ser. No. 10/927,228, filed Aug. 25, 2004, now U.S. Pat. No. 7,071,308, which is a divisional of U.S. patent application Ser. No. 10/008,566, filed Nov. 8, 2001, now U.S. Pat. No. 6,890,734, which claims benefit of U.S. Provisional Patent Applications Nos. 60/298,268, filed Jun. 14, 2001, and 60/247,218, filed Nov. 10, 2000, each of which is incorporated herein by reference.

FIELD OF THE INVENTION

The present invention relates to compositions and methods for affecting mammalian physiology, including hematopoietic cell proliferation or immune system function. In particular, it provides methods of using nucleic acids, proteins, and antibodies which regulate development and/or the immune system; and provides functional details on ligand-receptor pairing. Diagnostic and therapeutic uses of these materials are also disclosed.

BACKGROUND OF THE INVENTION

Recombinant DNA technology refers generally to techniques of integrating genetic information from a donor source into vectors for subsequent processing, such as through introduction into a host, whereby the transferred genetic information is copied and/or expressed in the new environment. Commonly, the genetic information exists in the form of complementary DNA (cDNA) derived from messenger RNA (mRNA) coding for a desired protein product. The carrier is frequently a plasmid having the capacity to incorporate cDNA for later replication in a host and, in some cases, actually to control expression of the cDNA and thereby direct synthesis of the encoded product in the host.

For some time, it has been known that the mammalian immune response is based on a series of complex cellular interactions, called the "immune network". Recent research has provided new insights into the inner workings of this network. While it remains clear that much of the immune response does, in fact, revolve around the network-like interactions of lymphocytes, macrophages, granulocytes, and other cells, immunologists now generally hold the opinion that soluble proteins, known as lymphokines, cytokines, or monokines, play critical roles in controlling these cellular interactions. Thus, there is considerable interest in the isolation, characterization, and mechanisms of action of cell modulatory factors, an understanding of which will lead to significant advancements in the diagnosis and therapy of numerous medical abnormalities, e.g., immune system disorders.

Lymphokines apparently mediate cellular activities in a variety of ways. They have been shown to support the proliferation, growth, and/or differentiation of pluripotent hematopoietic stem cells into vast numbers of progenitors comprising diverse cellular lineages which make up a complex immune system. Proper and balanced interactions between the cellular components are necessary for a healthy immune response. The different cellular lineages often respond in a different manner when lymphokines are administered in conjunction with other agents.

Cell lineages especially important to the immune response include two classes of lymphocytes: B-cells, which can produce and secrete immunoglobulins (proteins with the capability of recognizing and binding to foreign matter to effect its removal), and T-cells of various subsets that secrete lymphokines and induce or suppress the B-cells and various other cells (including other T-cells) making up the immune network. These lymphocytes interact with many other cell types. Monocytes are precursors of macrophages which, with dendritic cells, are functionally important in their roles as processors and presenters of antigen, an important step in initiation of an immune response.

IL-7 is a cell modulatory factor which affects hematopoietic cell growth and/or differentiation. See, e.g., Mire-Sluis and Thorpe (1998) *Cytokines* Academic Press, San Diego; Thomson (ed. 1998) *The Cytokine Handbook* (3d ed.) Academic Press, San Diego; Metcalf and Nicola (1995) *The Hematopoietic Colony Stimulating Factors* Cambridge University Press; and Aggarwal and Gutterman (1991) *Human Cytokines* Blackwell.

Research to better understand and treat various immune disorders has been hampered by the general inability to maintain cells of the immune system in vitro. Immunologists have discovered that culturing many of these cells can be accomplished through the use of T-cell and other cell supernatants, which contain various growth factors, including many of the lymphokines.

From the foregoing, it is evident that the understanding of the signal transduction pathways and identification of components in such pathways should contribute to new therapies for a wide range of degenerative or abnormal conditions which directly or indirectly involve development, differentiation, or function, e.g., of the immune system and/or hematopoietic cells. Furthermore, soluble regulatory molecules, including cytokines, are known to sometimes act outside the immune system with effects on physiology (leptin), morphogenesis, and tissue and skeletal remodeling (RANKL). Thus, the discovery and understanding of novel cytokine-like molecules and their receptors which enhance or potentiate the beneficial activities of other lymphokines would be highly advantageous.

SUMMARY OF THE INVENTION

The present invention is based, in part, on the discovery of the receptor complex for the cytokine ligand IL-B50. Moreover, identification of the components allows for the identification of cell types and stages which express the necessary components to be responsive to ligand. This provides insights and capacity to predict the physiological and immunological role of the cytokine.

The present invention provides, e.g., methods of producing a ligand:receptor complex, comprising contacting: a substantially pure or recombinant mammalian IL-B50 with a receptor comprising the IL-7Rα or the Rδ2 subunit; a mammalian IL-B50 with a receptor comprising a substantially pure or recombinant IL-7Rα subunit; or a mammalian IL-B50 with a receptor comprising a substantially pure or recombinant Rδ2 subunit; which contacting thereby allows the complex to form. In preferred embodiments, the mammalian IL-B50 is primate IL-B50, such as human IL-B50; the complex formation results in signal transduction, STAT activation, or TARC expression; the receptor is on a cell; the receptor comprises both IL-7Rα and Rδ2 subunit; the complex formation results in a physiological change in the cell expressing the receptor; the contacting is in combination with a proliferative agent, cytokine, or chemokine; the contacting allows quantitative detection of the ligand; or receptor is on a hematopoietic cell, including a lymphoid lineage cell, a myeloid cell such as a monocyte, or dendritic cell.

Another method is provided for modulating physiology or development of an IL-7Rα or Rδ2 expressing cell comprising contacting the cell to an exogenous agonist or antagonist of a mammalian IL-B50. Various embodiments include those wherein: the antagonist is an antibody which neutralizes the mammalian IL-B50, a mutein of the IL-B50; or an antibody which binds to IL-7Rα or Rδ2 or a complex of both; or the physiology is selected from proliferation, lymphoid lineage cell development, antigen presentation, or production of inflammatory mediators, including cytokines, chemokines, or adhesion molecules; or the cell is a hematopoietic cell. Other embodiments include those wherein: the antagonist is an antibody and the physiology is hematopoietic cell proliferation; the agonist is IL-B50 and the physiology is hematopoietic cell differentiation; the physiology is antigen presentation; or the modulating is blocking, and the physiology is lymphoid lineage cell proliferation.

Other embodiments provide methods of modulating a signal to a cell mediated by IL-B50 comprising contacting the cell to an administered agonist or antagonist of IL-B50. These include those wherein the modulating is inhibiting, and the signal is a proliferation signal; the antagonist is a neutralizing antibody to IL-7Rα or the Rδ2 subunit or a complex comprising the subunits; the agonist or antagonist is administered in combination with another antagonist or agonist of IL-B50; the agonist or antagonist is administered in combination with a growth factor, cytokine, chemokine, or immune adjuvant; or the contacting is with another anti-proliferative agent or treatment.

Other methods include those of selectively labeling a population of cells, the method comprising contacting the cells with an antibody which binds: IL-7Rα; Rδ2; or a complex comprising one of the subunits; thereby resulting in the identification of cells expressing the subunit or complex. Certain embodiments include those wherein: the contacting results in modulation of STAT activation; the labeling allows purification of IL-7Rα or Rδ2 subunit expressing cells; or the labeling allows depletion of IL-7Rα or Rδ2 subunit expressing cells. Also provided are populations of cells made by the methods, including those which are prepared by Fluorescent Activated Cell Sorting.

The invention further provides methods of testing a compound for ability to affect receptor-ligand interaction, the method comprising comparing the interaction of a receptor complex comprising IL-7Rα and/or Rδ2 subunit with IL-B50 in the presence and absence of the compound. In certain embodiments, the compound is an antibody which binds one of: IL-7Rα; Rδ2 subunit; a receptor comprising IL-7R and/or Rδ2; or IL-B50.

Certain compositions are provided, e.g., an isolated or recombinant protein complex comprising: at least 15 contiguous amino acid residues of SEQ ID NO: 2 and at least 15 contiguous amino acid residues of SEQ ID NO: 4; at least two distinct segments of at least 8 contiguous amino acid residues of SEQ ID NO: 2 and at least two distinct segments of at least 8 contiguous amino acid residues of SEQ ID NO: 4; or at least one segment at least 21 contiguous nucleotides of SEQ ID NO: 1 and at least one segment at least 21 contiguous nucleotides of SEQ ID NO: 3. In preferred embodiments, one of the segments of SEQ ID NO: 2 is from the extracellular portion of the sequence; one of the segments of SEQ ID NO: 4 is from the extracellular portion of the sequence; or the polypeptide comprises the mature SEQ ID NO: 2 and the mature SEQ ID NO: 4 sequences.

Nucleic acid embodiments include an isolated or recombinant polynucleotide encoding described components of the complex, wherein: the polynucleotide comprises a deoxyribonucleotide; the polynucleotide comprises a ribonucleotide; or at least one of the segments is operably linked to a promoter.

Antibodies are also provided which recognize epitopes presented by the complex, e.g., a binding compound comprising an antigen binding portion from an antibody which binds with selectivity to a polypeptide comprising at least 12 contiguous amino acid residues of SEQ ID NO: 2 and at least 12 contiguous amino acid residues of SEQ ID NO: 4.

BRIEF DESCRIPTION OF THE FIGURES

FIGS. 1A-1E show the nucleotide and amino acid sequences (see SEQ ID NO: 1 and 2) of a primate, e.g., human, IL-7Rα; predicted signal cleavage site indicated.

FIGS. 2A-2E show the nucleotide and amino acid sequences (see SEQ ID NO: 3 and 4) of a primate, e.g., human, Rδ2; predicted signal cleavage site indicated.

FIGS. 3A and 3B show the amino acid (SEQ ID NO:6) and nucleotide sequences (SEQ ID NO:5), respectively, of primate, e.g., human, IL-B50; predicted signal cleavage position indicated.

FIG. 11A shows the effect on the production of IL-4;

FIG. 11B shows the effect on the production of IL-13; FIG. 11C shows the effect on the production of IFN-γ, FIG. 11D shows the effect on the production of IL-10 and FIG. 11E shows the effect on the production of TNF-α.

FIGS. 14A-14C show the results of a comparison of IL-B50 with GM-CSF, IL-7, CD40-ligand (CD40L) and medium alone as a control, to stimulate human DCs to produce mRNA for various cytokines and chemokines. FIG. 14A shows effects on IL-1α, IL-1β, IL-6, IL-2p40 and TNF-α. FIG. 14B shows effects on TARC, MDC and MIP3-β. FIG. 14C shows effects on MCP-1, MCP-4, Rantes and MIG.

DETAILED DESCRIPTION OF THE PREFERRED EMBODIMENTS

Outline

Figure 4A:
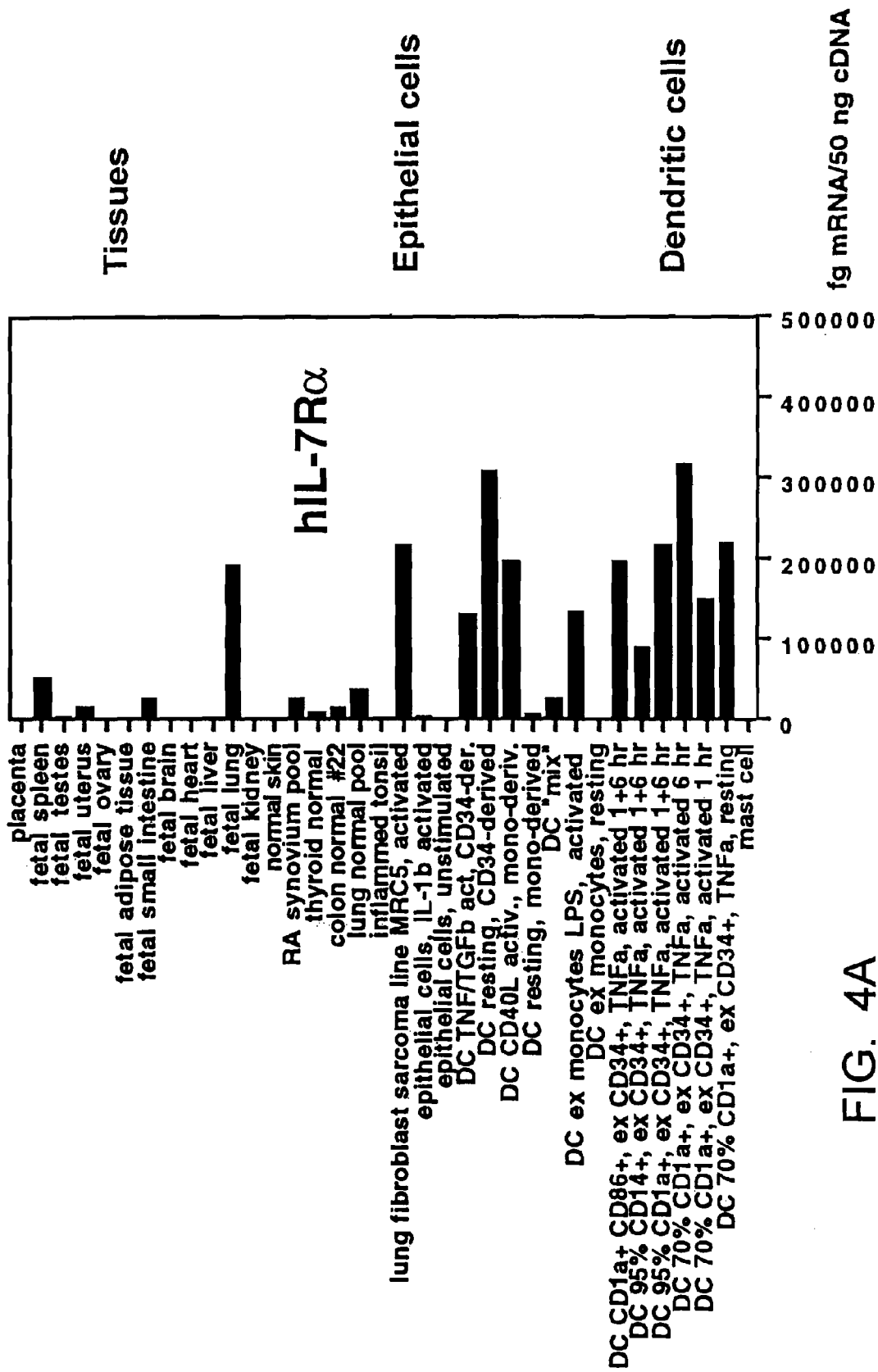
FIGS. 4A-4E show expression levels of hIL-7Rα (FIGS. 4A-4B), Rδ2 (hTSLPR, FIGS. 4C-4D), and IL-B50 in various tissues and cell types. Expression levels were normalized and expressed as femtograms mRNA per 50 ng total cDNA.
Figure 4B:
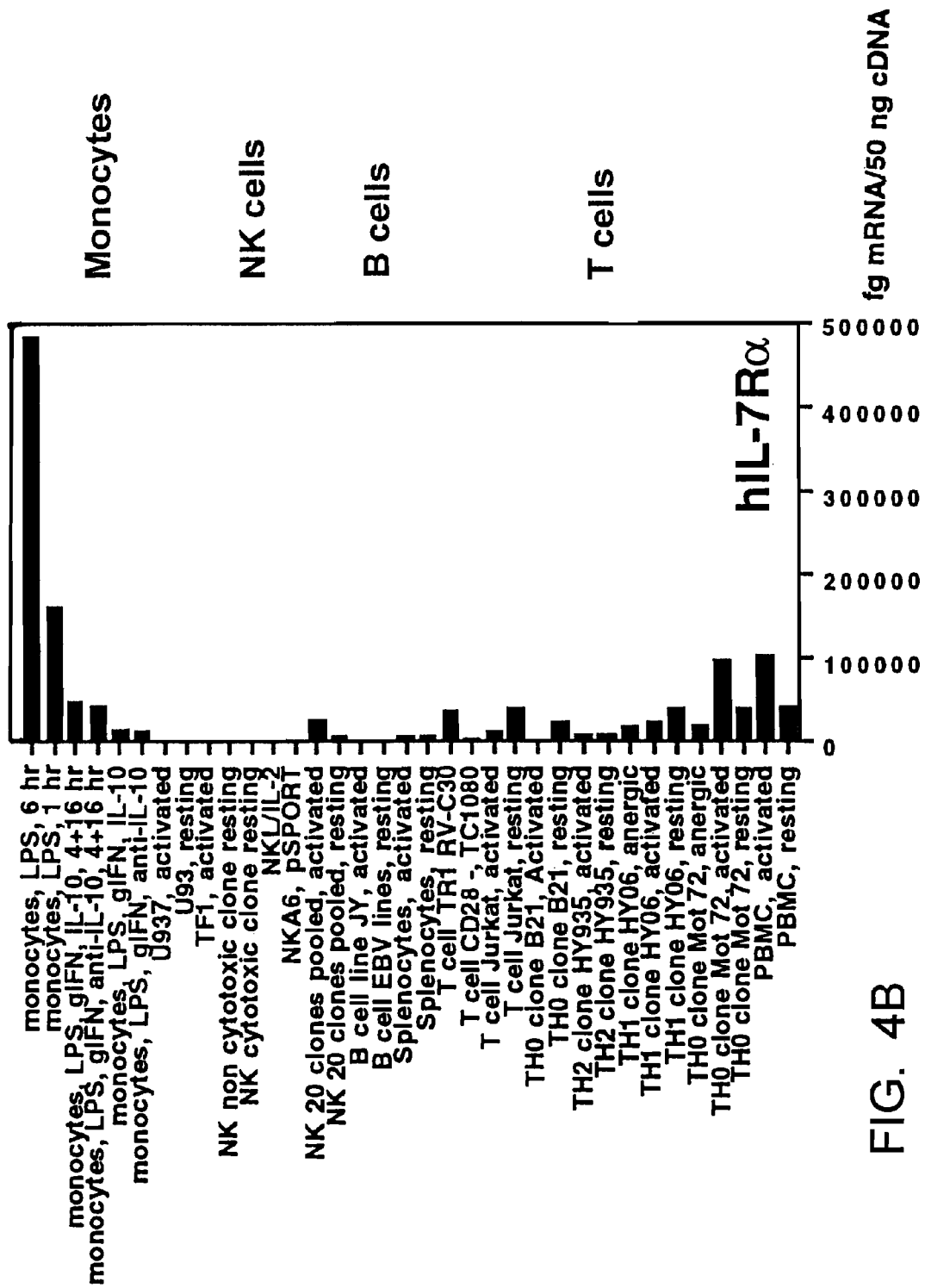
Figure 4C:
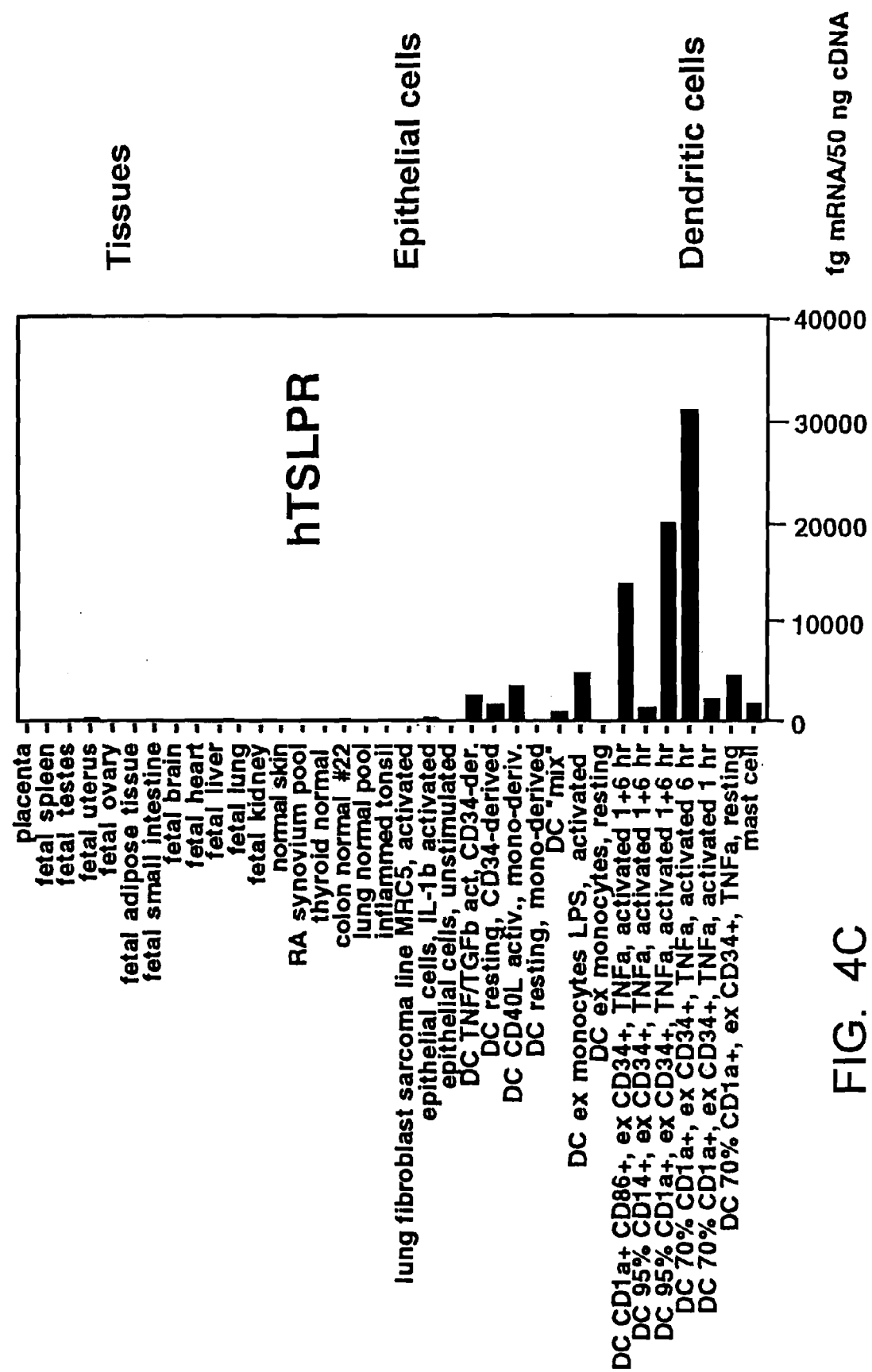
Figure 4D:
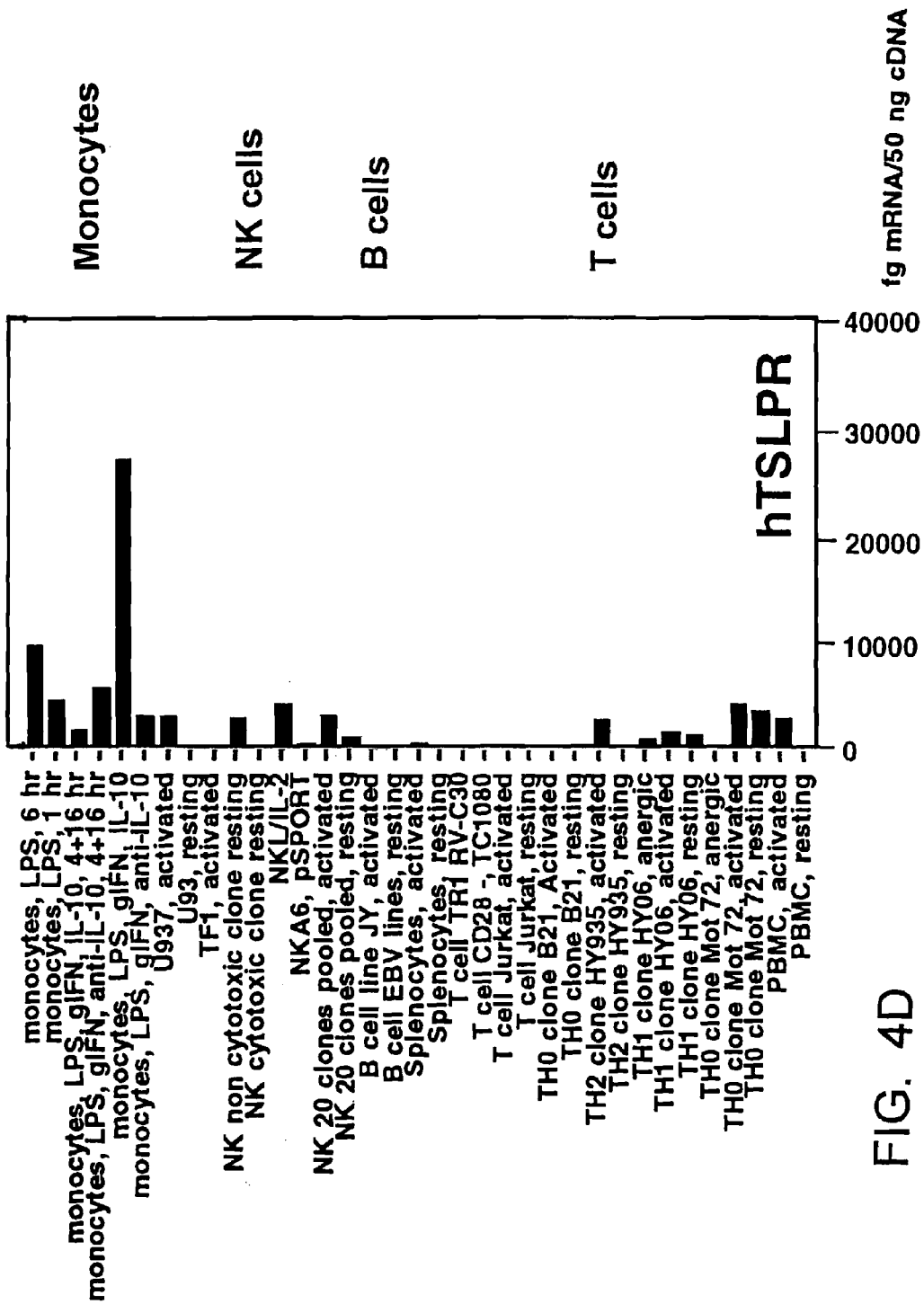

I. General
II. Activities
III. Nucleic Acids
   A. encoding fragments, sequence, probes
   B. mutations, chimeras, fusions
   C. making nucleic acids
   D. vectors, cells comprising
IV. Proteins, Peptides
   A. fragments, sequence, immunogens, antigens
   B. muteins
   C. agonists/antagonists, functional equivalents
   D. making proteins
V. Making nucleic acids, proteins
VI. Antibodies
   A. polyclonals
   B. monoclonal, Kd
   C. anti-idiotypic antibodies
   D. hybridoma cell lines
VII. Kits and Methods to quantify ligand/receptor
   A. ELISA
   B. assay mRNA encoding
   C. qualitative/quantitative
   D. kits
VIII. Therapeutic compositions, methods
   A. combination compositions
   B. unit dose
   C. administration
IX. Receptors

I. General

Before the present compositions, formulations, and methods are described, it is to be understood that this invention is not limited to the particular methods, compositions, and cell lines described herein, as such methods, compositions, and cell lines may, of course, vary. It is also to be understood that the terminology used herein is for the purpose of describing particular embodiments.

As used herein, including the appended claims, singular forms of words such as "a," "an," and "the" include their corresponding plural referents unless the context clearly dictates otherwise. Thus, e.g., reference to "an organism" includes one or more different organisms, reference to "a cell" includes one or more of such cells, and reference to "a method" includes reference to equivalent steps and methods known to a person of ordinary skill in the art, and so forth.

Unless otherwise defined, technical and scientific terms used herein have the same meaning as commonly understood by a person of ordinary skill in the art to which this invention belongs. Although methods and materials similar or equivalent to those described herein can be used in the practice or testing of the present invention, suitable methods and materials are described below. Publications, patent applications, patents, and other references discussed above are provided solely for their disclosure prior to the filing date of the present application. Nothing herein is to be construed as an admission that the invention is not entitled to antedate any such disclosure by virtue of its prior invention. Publications, patent applications, patents, and other references mentioned herein are incorporated by reference in their entirety including all figures and drawings.

The present invention is based on the discovery of the receptor subunits for the IL-B50 cytokine. This allows advantageous coproduction of the subunits on vectors, production of fusion proteins, and antibody preparations which recognize epitopes resulting from the interaction of the subunit components into a functional unit.

IL-7 biology is reasonably well described. See, e.g., Stoddart, et al. (2000) *Immunol. Rev.* 175:47-58; Puel and Leonard (2000) *Curr. Opin. Immunol.* 12:468-473; Akashi, et al. (2000) *Curr. Opin. Immunol.* 12:144-150; Watanabe, et al. (1999) *Immunol. Res.* 20:251-259; Waldmann (2000) *Ann. Oncol.* 11 Suppl 1:101-106; Beverley and Grubeck-Loebenstein (2000) *Vaccine* 18:1721-1724; Aspinall and Andrew (2000) *Vaccine* 18:1629-1637; Appasamy (1999) *Cytokines Cell Mol. Ther.* 5:25-39; Hofmeister, et al. (1999) *Cytokine Growth Factor Rev.* 10:41-60; Or, et al. (1998) *Cytokines Cell Mol. Ther.* 4:287-294; Akashi, et al. (1998) *Immunol. Rev.* 165:13-28; and Offner and Plum (1998) *Leuk. Lymphoma* 30:87-99. Moreover, since the IL-7 receptor and the IL-B50 receptor share one subunit, the signaling pathways and biology should significantly overlap. This is similar to the GM/IL-3/IL-5 family, which is one of the first groups whose overlapping biologies were explained by the sharing of receptor subunits.

Additionally, recognition of the receptor subunits provides the opportunity to determine cell types and developmental stages where the functional receptor components are coordinately expressed. This provides the opportunity to determine what cell types are likely to respond to ligand, and the resulting biological functions mediated by those cells provides suggestions as to the physiological effects mediated by the ligand. This leads to better understanding of therapeutic uses of the ligand or blocking ligand:receptor interaction and signaling.

Some of the standard methods applicable are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols 1-3, CSH Press, NY; Ausubel, et al., *Biology*, Greene Publishing Associates, Brooklyn, N.Y.; or Ausubel, et al. (1987 and periodic supplements) *Current Protocols in Molecular Biology*, Greene/Wiley, New York; each of which is incorporated herein by reference. See also U.S. Ser. No. 09/130,972, which is incorporated herein by reference.

A complete nucleotide (SEQ ID NO: 1) and corresponding amino acid sequence (SEQ ID NO: 2) of a primate, e.g., human, IL-7Rα coding segment is shown in FIG. 1; similarly for Rδ2 in FIG. 2. FIG. 3 provides sequence of primate, e.g., human, IL-B50. See U.S. Ser. No. 09/399,492, which is incorporated herein by reference.

For the IL-7Rα subunit, notable predicted features include, e.g., CK2 phosphorylation sites at about S24-E27, T47-E50, S187-D190, S214-E217, S255-D258, S282-D285, S355-D358, and S423-E426; peroxisomal motif at about S133-L135; PKC phosphorylation sites at about T76-K78, T97-K99, S165-K167, S315-K317, S364-R366, and S373-K375; receptor cyt2 motif at about G195-S201; cAMP kinase motif at about f342-S346; cAMP kinase motif at about R343-S346 or R343-L367; GSK3 motifs at about T129-S133, S201-Y205, T208-n212, S324-p330, T337-[4], S363-S367, and T413-S417; N glycosylation sites at about N29-S31, N45-T47, N131-S133, N162-S164, N212-S214, N213-S215, N275-S277, N353-S355, and N392-T394; tyrosine kinase motif at about E14-Y18; cAMP PK sites at about K94-T97, K84-S87, R343-S346, Cas phos sites at about T208-K210, S215-E217, T262-E264, S331-D333, T337-E339, and S367-D369; cyt C me sites at about T76-F79, C98-I101, Q136-Y139, W244-R247, H259-T261, and C267-P270; histone methylation sites at about F85-L88, Q172-L175, and P270-N273; myristoly sites at about G322-S326, G352-A256, and G389-S392; Phos2 sites at about K184/S187, R343/S345, R343/S346, and R371/S373; and PKC phos sites at about T76-K78, T97-K99, S165-K167, S315-K317, S364-R366, and S373-K375.

Regions of particular interest from the Rδ2 sequence include predictions of, e.g., CK2 phosphorylation sites at about T115-D118, S120-D123, S132-D135, S140-E143, S242-D245, S284-E287, and T297-E300; peroxisomal localization motifs at about S218-F220 and A272-L274; PKC phosphorylation sites at about S76-R78, S99-K101, and S300-R302; tyr phosphorylation sites at about R39/D43/Y46 and K166/E169/Y172; cAMP kinase sites at about i77-T81 and R78-T82; Ca++ kinase site at about R78-h82; GSK3 sites at about T23-S27, S99-v103, T113-S117, S132-t136, T136-S140, T199-p203, T201-p205, T297-S301, and S301-1305; SigPase sites at about A195-A197 and A278-A280; Tyr kinase site at about D70-Y74; cAMP PK sites at about R78-T81, K96-S99, K157-S160, and K312-S315; Ca++phosphatase sites at about T149-E151 and T309-E311; cyt C Me site at about V235-F238; myristoly sites at about F3-G7 and G329-T333; N glycosylation sites at about N25-S27, N33-T35, N79-T81, and N147-T149; phos2 sites at about K28/S30, K96/S98, K96/S99, R104/S106, K206/S208, and K312/S315; PKC phosphorylation sites at about S76-R78, S99-K100, and S301-R303; SPKK sites at about S99-h103 and S301-m303; and Tyr Kinase sites at about R39-Y46.

In the IL-B50 sequence, the region from K97-K103 is known to be subject to proteolysis, and mutations may be targeted to that region to protect the ligand from proteolytic degradation. Thus, pharmacokinetic properties of the ligand may be modified, especially for the indications described herein.

Segments with boundaries adjacent these positions will be particularly useful, as will polynucleotides encoding such segments. Mutagenesis in these regions will be used to determine structure-activity relationship, particularly with the receptor, as provided herein.

As used herein, the term "primate IL-7Rα" shall be used to describe a protein comprising a protein or peptide segment having or sharing the amino acid sequence shown in FIGS. 1A-1E (SEQ ID NO:2), or a substantial fragment thereof; but distinct from rodent sequences. The invention also includes protein variations of the IL-7Rα allele whose sequence is provided, e.g., a mutein agonist or antagonist. Typically, such agonists or antagonists will exhibit less than about 10% sequence differences, and thus will often have between 1- and 11-fold substitutions, e.g., 2-, 3-, 5-, 7-fold, and others. It also encompasses allelic and other variants, e.g., natural polymorphic variants, of the protein described. "Natural" as used herein means umodified by artifice, found, e.g., in natural sources. Typically, it will bind, when in a functional receptor complex, to ligand with high affinity, e.g., at least about 100 nM, usually better than about 30 nM, preferably better than about 10 nM, and more preferably at better than about 3 nM. The term shall also be used herein to refer to related naturally occurring forms, e.g., alleles, polymorphic variants, and metabolic variants of the primate protein. Corresponding meanings apply to uses of terms related to the Rδ2 sequences.

This invention also encompasses proteins or peptides having amino acid sequence homology with combinations of amino acid sequences presented in FIGS. 1 and 2. In particular, it will include fusion constructs or proteins comprising segments from both of the sequences provided.

A substantial polypeptide "fragment", or "segment", is a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. Sequences of segments of different proteins can be compared to one another over appropriate length stretches.

Amino acid sequence homology, or sequence identity, is determined by optimizing residue matches, if necessary, by introducing gaps as required. See, e.g., Needleham, et al., (1970) *J. Mol. Biol.* 48:443-453; Sankoff, et al., (1983) chapter one in *Time Warps, String Edits, and Macromolecules: The Theory and Practice of Sequence Comparison*, Addison-Wesley, Reading, Mass.; and software packages from IntelliGenetics, Mountain View, Calif.; and the University of Wisconsin Genetics Computer Group (GCG), Madison, Wis.; each of which is incorporated herein by reference. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are intended to include natural allelic and interspecies variations in the cytokine sequence. Typical homologous proteins or peptides will have from 50-100% homology (if gaps can be introduced), to 60-100% homology (if conservative substitutions are included) with an amino acid sequence segment of FIG. 1 or 2. Homology measures will be at least about 70%, generally at least 76%, more generally at least 81%, often at least 85%, more often at least 88%, typically at least 90%, more typically at least 92%, usually at least 94%, more usually at least 95%, preferably at least 96%, and more preferably at least 97%, and in particularly preferred embodiments, at least 98% or more. The degree of homology will vary with the length of the compared segments. Homologous proteins or peptides, such as the allelic variants, will share most biological activities with the embodiments shown in FIGS. 1 and 2. As used herein, the term "biological activity" is used to describe, without limitation, effects on immune or other cell proliferation, differentiation, induction of cytokines or chemokines (e.g., TARC, PARC, MDC, MIP3-b, etc.), effects on STAT3 and/or STAT5 mediated signal transduction, antigen presentation effects, changes in cell surface molecule expression, and Th2 specific activities.

The terms ligand, agonist, antagonist, and analog of these receptors, particularly the functional complex, include molecules that modulate the characteristic cellular responses to the IL-B50, as well as molecules possessing the more standard structural binding competition features of ligand-receptor interactions, e.g., where the receptor is a natural receptor or an antibody. The cellular responses likely are mediated through binding of IL-B50 to cellular receptors, as described. Also, a ligand is a molecule which serves either as a natural ligand to which said receptor, or an analog thereof, binds, or a molecule which is a functional analog of the natural ligand. The functional analog may be a ligand with structural modifications, or may be a wholly unrelated molecule which has a molecular shape which interacts with the appropriate ligand binding determinants. The ligands may serve as agonists or antagonists, see, e.g., Goodman, et al. (eds.) (1990) *Goodman & Gilman's: The Pharmacological Bases of Therapeutics*, Pergamon Press, New York.

Rational drug design may also be based upon structural studies of the molecular shapes of a receptor or antibody and other effectors or ligands. Effectors may be other proteins which mediate other functions in response to ligand binding, or other proteins which normally interact with the receptor. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallogaphy*, Academic Press, New York, which is hereby incorporated herein by reference.

II. Activities

The IL-B50 proteins have a number of different biological activities based on coexpression of IL-7Rα and Rδ2, e.g., in the immune system, and include proliferative, developmental, or physiological functions, in particular of lymphoid lineage cells, e.g., macrophages or dendritic cells. The IL-B50 proteins are homologous to other IL-7 ligand family proteins, but each have structural differences. For example, human IL-B50 shows 43% amino acid sequence identity to mouse TSLP. Additionally, the human receptor subunit Rδ2 displays 39% amino acid sequence identity to mouse TSLPR.

The mouse IL-B50 molecule has the ability to stimulate TARC production and various Th2 specific cytokines. The signaling pathway seems to use STAT3 and/or STAT5, and sends proliferation or differentiation signals. Differentiation tends to result in limitation of proliferation, and vice versa. Differentiation typically results in changes in cell surface marker expression.

As shown herein, human IL-B50 improves dendritic cell survival in cultures, upregulates the expression of costimulatory molecules and adhesion molecules, including HLA-DR, CD40, CD80, CD86, CD11a, CD18 and CD83, induces dendritic cells to produce the chemokines TARC, PARC and MDC, and strongly promotes the capacity of dendritic cells to induce naïve T cells to proliferate and to produce cytokines IL4, IL-13, and TNF-alpha. Additionally, IL-B50 has a synergistic effect with CD40-ligand and LPS in activated dendritic cells to upregulate costimulatory molecules CD40, CD80 and CD86. IL-B50 also strongly enhances CD40-ligand-induced production of IL-12 by dendritic cells.

TARC, PARC and MDC are all notably ligands for CCR4, a chemokine receptor predominantly found on Th2-type lymphocytes. Thus, IL-B50 can activate myeloid cells, such as monocytes, to release chemokines that may attract effector cells with a Th2 phenotype. As shown in the examples below, IL-B50-induced expression of TARC was very strong in the CD11c$^+$ subset of DCs. This subset, representing less than 1% of mononuclear cells in the blood, normally differentiates into mature DCs in response to inflammatory stimuli. The expression of TARC in these cells was accompanied by a dramatic enhancement of their maturation as evidenced by the strong induction of the costimulatory molecules CD40 and CD80. These results indicate that this DC subset stimulated with IL-B50 could be a potent inducer of primary T-cell-mediated immune responses. Indeed, CD11+DCs cultured in the presence of IL-B50 are much more potent in their capacity to elicit the proliferation of naïve T cells as compared to DC cultured in medium.

Dendritic cells are professional antigen presenting cells, which are capable of inducing primary antigen-specific T cell-mediated immune responses. Dendritic cells play a critical role in initiating immune responses against tumors and infectious microorganisms. Dendritic cells are also involved in autoimmune diseases, allergic diseases, graft-versus-host disease and rejection of solid organ transplants. Therefore, enhancing dendritic cell function allows for treatment of tumors and infectious diseases. Similarly, blocking dendritic cell function provides therapies for autoimmune diseases, allergic diseases, graft-versus-host diseases and transplantation associated rejection.

Thus, IL-B50 may be used in enhancing dendritic cell function in treating cancers and infectious diseases and IL-B50 antagonists may be used in blocking the function of dendritic cells in treating autoimmune diseases, allergic diseases, graft-versus-host diseases and transplantation associated rejection. The elucidation of the IL-B50 receptor subunits, therefore, allows for the identification of agonists and antagonists of ILB-50 for use in treating the aforementioned diseases.

The present disclosure also describes new assays for activities described for these molecules. Corresponding activities should be found in other mammalian systems, including primates. The new IL-7-like molecules produced by recombinant means exhibit a biological activity of modulating lymphoid lineage cells. Furthermore, there is substantial likelihood of synergy with other IL-7 related agonists or antagonists. It is likely that the receptors, which are expected to include multiple different polypeptide chains, exhibit species specificity for their corresponding ligands.

III. Nucleic Acids

This invention contemplates use of isolated nucleic acid or fragments, e.g., which encode these or closely related proteins, or fragments thereof, e.g., fusion proteins or coordinately expressed or combination expression constructs.

The term "isolated nucleic acid or fragments" as used herein means a nucleic acid, e.g., a DNA or RNA molecule, that is not immediately contiguous with sequences present in the naturally occurring genome of the organism from which it is derived. Thus, the term describes, e.g., a nucleic acid that is incorporated into a vector, such as a plasmid or viral vector; a nucleic acid that is incorporated into the genome of a heterologous cell (or the genome of homologous cell, but at a site different from that at which it normally occurs); and a nucleic acid that exists as a separate molecule, e.g., a DNA fragment produced by PCR amplification or restriction enzyme digestion, or an RNA molecule produced by in vitro transcription. The term also describes a recombinant (e.g., genetically engineered) nucleic acid that forms part of a hybrid gene encoding additional polypeptide sequences that can be used, e.g., in the production of a fusion protein. In addition, this invention embodies any engineered or nucleic acid molecule created by artifice that encodes a biologically active protein or polypeptide having characteristic IL-B50 receptor activity. Typically, the nucleic acid is capable of hybridizing, under appropriate conditions, with nucleic acid sequence segments shown in FIGS. 1 and 2. Further, this invention covers the use of isolated or recombinant nucleic acid, or fragments thereof, which encode proteins having fragments which are homologous to the newly disclosed receptor complex proteins. The isolated nucleic acids can have the respective regulatory sequences in the 5' and 3' flanks, e.g., promoters, enhancers, poly-A addition signals, and others from the natural gene.

An "isolated" nucleic acid is a nucleic acid, e.g., an RNA, DNA, or a mixed polymer, which is substantially pure, e.g., separated from other components which naturally accompany a native sequence, such as ribosomes, polymerases, and flanking genomic sequences from the originating species. The term embraces a nucleic acid sequence which has been removed from its naturally occurring environment, and includes recombinant or cloned DNA isolates, which are thereby distinguishable from naturally occurring compositions, and chemically synthesized analogs or analogs biologically synthesized by heterologous systems. A substantially pure molecule includes isolated forms of the molecule, either completely or substantially pure.

An isolated nucleic acid will generally be a homogeneous composition of molecules, but will, in some embodiments, contain heterogeneity, preferably minor. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence. Typically this intervention involves in vitro manipulation, although under certain circumstances it may involve more classical animal breeding techniques. Alternatively, it can be a nucleic acid made by generating a sequence comprising fusion of two fragments which are not naturally contiguous to each other, but is meant to exclude products of nature, e.g., naturally occurring mutants as found in their natural state. Thus, e.g., products made by transforming cells with any unnaturally occurring vector is encompassed, as are nucleic acids comprising sequence derived using any synthetic oligonucleotide process. Such a process is often done to replace a codon with a redundant codon encoding the same or a conservative amino acid, while typically introducing or removing a restriction enzyme sequence recognition site. Alternatively, the process is performed to join together nucleic acid segments of desired functions to generate a single genetic entity comprising a desired combination of functions not found in the commonly available natural forms, e.g., encoding a fusion protein. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. This will include a dimeric repeat. Specifically included are synthetic nucleic acids which, by genetic code redundancy, encode similar combination polypeptides to fragments of the receptor subunits and fusions of sequences from various different receptors or related molecules, e.g., growth factors.

A "fragment" in a nucleic acid context is a contiguous segment of at least about 17 nucleotides, generally at least 21 nucleotides, more generally at least 25 nucleotides, ordinarily at least 30 nucleotides, more ordinarily at least 35 nucleotides, often at least 39 nucleotides, more often at least 45 nucleotides, typically at least 50 nucleotides, more typically at least 55 nucleotides, usually at least 60 nucleotides, more usually at least 66 nucleotides, preferably at least 72 nucleotides, more preferably at least 79 nucleotides, and in particularly preferred embodiments will be at least 85 or more nucleotides including, e.g., 100, 150, 200, 250, etc. Typically, fragments of different genetic sequences can be compared to one another over appropriate length stretches, particularly defined segments such as the domains described below.

A nucleic acid which codes for an IL-B50 receptor complex will be particularly useful to identify genes, mRNA, and cDNA species which code for itself or closely related proteins, as well as DNAs which code for polymorphic, allelic, or other genetic variants, e.g., from different individuals or related species. Preferred probes for such screens are those regions of the interleukin which are conserved between different polymorphic variants or which contain nucleotides which lack specificity, and will preferably be full length or nearly so. In other situations, polymorphic variant specific sequences will be more useful.

This invention further covers recombinant nucleic acid molecules and fragments having a nucleic acid sequence identical to or highly homologous to the isolated DNA set forth herein. In particular, the sequences will often be operably linked to DNA segments which control transcription, translation, and DNA replication. These additional segments typically assist in expression of the desired nucleic acid segment.

Homologous nucleic acid sequences, when compared to one another or to the sequences shown in FIG. 1 or 2, exhibit significant similarity. The standards for homology in nucleic acids are either measures for homology generally used in the art by sequence comparison or based upon hybridization conditions. Comparative hybridization conditions are described in greater detail below.

Substantial identity in the nucleic acid sequence comparison context means either that the segments, or their complementary strands, when compared, are identical when optimally aligned, with appropriate nucleotide insertions or deletions, in at least about 60% of the nucleotides, generally at least 66%, ordinarily at least 71%, often at least 76%, more often at least 80%, usually at least 84%, more usually at least 88%, typically at least 91%, more typically at least about 93%, preferably at least about 95%, more preferably at least about 96 to 98% or more, and in particular embodiments, as high at about 99% or more of the nucleotides, including, e.g., segments encoding structural domains such as the segments described below. Alternatively, substantial identity will exist when the segments will hybridize under selective hybridization conditions, to a strand or its complement, typically using a sequence derived from the sequences depicted in FIGS. 1 and 2. Typically, selective hybridization will occur when there is at least about 55% homology over a stretch of at least about 14 nucleotides, more typically at least about 65%, preferably at least about 75%, and more preferably at least about 90%. See, Kanehisa (1984) *Nuc. Acids Res.* 12:203-213. The length of homology comparison, as described, may be over longer stretches, and in certain embodiments will be over a stretch of at least about 17 nucleotides, generally at least about 20 nucleotides, ordinarily at least about 24 nucleotides, usually at least about 28 nucleotides, typically at least about 32 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters typically controlled in hybridization reactions. Stringent temperature conditions will usually include temperatures in excess of about 30 degrees C., more usually in excess of about 37 degrees C., typically in excess of about 45 degrees C., more typically in excess of about 55 degrees C., preferably in excess of about 65 degrees C., and more preferably in excess of about 70 degrees C. Stringent salt conditions will ordinarily be less than about 500 mM, usually less than about 400 mM, more usually less than about 300 mM, typically less than about 200 mM, preferably less than about 100 mM, and more preferably less than about 80 mM, even down to less than about 20 mM. Certain detergents or destabilizing reagents may be added, e.g., formamide at 50%, etc. However, the combination of parameters is much more important than the measure of any single parameter. See, e.g., Wetmur and Davidson (1968) *J. Mol. Biol.* 31:349-370, which is hereby incorporated herein by reference.

The isolated DNA can be readily modified by nucleotide substitutions, nucleotide deletions, nucleotide insertions, and inversions of nucleotide stretches. These modifications result in novel DNA sequences which encode this protein or its derivatives. These modified sequences can be used to produce mutant proteins (muteins) or to enhance the expression of variant species. Enhanced expression may involve gene amplification, increased transcription, increased translation, and other mechanisms. Such mutant receptor-like derivatives include predetermined or site-specific mutations of the protein or its fragments, including silent mutations using genetic code degeneracy. "Mutant IL-B50 receptor" as used herein encompasses a polypeptide otherwise falling within the homology definition of the receptor as set forth above, but having an amino acid sequence which differs from that of other IL-7 receptor-like proteins as found in nature, whether by way of deletion, substitution, or insertion. In particular, "site specific mutant IL-B50 receptor" encompasses a protein having substantial homology with a protein shown in FIGS. 1 and 2, and typically shares most of the biological activities of the form disclosed herein.

Although site specific mutation sites are predetermined, mutants need not be site specific. Mammalian IL-B50 receptor mutagenesis can be achieved by making amino acid insertions or deletions in the gene, coupled with expression. Substitutions, deletions, insertions, or any combinations may be generated to arrive at a final construct. Insertions include amino- or carboxy-terminal fusions. Random mutagenesis can be conducted at a target codon and the expressed mammalian IL-B50 receptor mutants can then be screened for the desired activity. Methods for making substitution mutations at predetermined sites in DNA having a known sequence are well known in the art, e.g., by M13 primer mutagenesis. See also Sambrook, et al. (1989) and Ausubel, et al. (1987 and periodic Supplements).

The mutations in the DNA normally should not place coding sequences out of reading frames and preferably will not create complementary regions that could hybridize to produce secondary mRNA structure such as loops or hairpins.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Polymerase chain reaction (PCR) techniques can often be applied in mutagenesis. Alternatively, mutagenesis primers are commonly used methods for generating defined mutations at predetermined sites. See, e.g., Innis, et al. (eds. 1990) *PCR Protocols: A Guide to Methods and Applications* Academic Press, San Diego, Calif.; and Dieffenbach and Dveksler (eds. 1995) *PCR Primer: A Laboratory Manual* Cold Spring Harbor Press, CSH, NY.

IV. Proteins, Peptides

As described above, the present invention encompasses primate IL-B50 receptor, e.g., whose sequences are disclosed in FIGS. 1 and 2, and described above. Allelic and other variants are also contemplated, including, e.g., fusion proteins combining portions of such sequences with others, including epitope tags and functional domains.

The present invention also provides recombinant proteins, e.g., heterologous fusion proteins using segments from these primate proteins. A heterologous fusion protein is a fusion of proteins or segments which are naturally not normally fused in the same manner. Thus, the fusion product of a growth factor receptor with a cytokine receptor is a continuous protein molecule having sequences fused in a typical peptide linkage, typically made as a single translation product and exhibiting properties, e.g., antigenicity, derived from each source peptide. A similar concept applies to heterologous nucleic acid sequences.

In addition, new constructs may be made from combining similar functional or structural domains from other related proteins, e.g., growth factors or other cytokines. For example, receptor-binding or other segments may be "swapped" between different new fusion polypeptides or fragments. See, e.g., Cunningham, et al. (1989) *Science* 243:1330-1336; and O'Dowd, et al. (1988) *J. Biol. Chem.* 263:15985-15992, each of which is incorporated herein by reference. Thus, new chimeric polypeptides exhibiting new combinations of specificities will result from the functional linkage of receptor-binding specificities. For example, the ligand binding domains from other related receptor molecules may be added or substituted for other domains of these or related proteins. The resulting protein will often have hybrid function and properties. For example, a fusion protein may include a labeling epitope which may serve to provide diagnostic locatability of the fusion protein for histology or other methods.

Candidate fusion partners and sequences can be selected from various sequence data bases, e.g., GenBank, c/o IntelliGenetics, Mountain View, Calif.; and BCG, University of Wisconsin Biotechnology Computing Group, Madison, Wis., which are each incorporated herein by reference.

"Derivatives" of the mammalian IL-B50 receptor include amino acid sequence mutants, glycosylation variants, metabolic derivatives and covalent or aggregative conjugates with other chemical moieties. Covalent derivatives can be prepared by linkage of functionalities to groups which are found in the IL-B50 receptor amino acid side chains or at the N- or C-termini, e.g., by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the interleukin or fragments thereof with other proteins of polypeptides. These derivatives can be synthesized in recombinant culture such as N- or C-terminal fusions or by the use of agents known in the art for their usefulness in cross-linking proteins through reactive side groups. Preferred derivatization sites with cross-linking agents are at free amino groups, carbohydrate moieties, and cysteine residues.

Fusion polypeptides between the receptors and other homologous or heterologous proteins are also provided. Homologous polypeptides may be fusions between different receptors, resulting in, for instance, a hybrid protein exhibiting binding specificity for multiple different ligands, or a receptor which may have broadened or weakened specificity of binding to its ligand. Likewise, heterologous fusions may be constructed which would exhibit a combination of properties or activities of the derivative proteins. Typical examples are fusions of a reporter polypeptide, e.g., luciferase, with a segment or domain of a receptor, e.g., a ligand-binding segment, so that the presence or location of a desired receptor may be easily determined. See, e.g., Dull, et al., U.S. Pat. No. 4,859,609, which is hereby incorporated herein by reference. Other gene fusion partners include glutathione-S-transferase (GST), bacterial β-galactosidase, trpE, Protein A, β-lactamase, alpha amylase, alcohol dehydrogenase, yeast alpha mating factor, or other cytokine receptors. See, e.g., Godowski, et al. (1988) *Science* 241:812-816.

The phosphoramidite method described by Beaucage and Carruthers (1981) *Tetra. Letts.* 22:1859-1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, PEGylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), Vols. 1-3, Cold Spring Harbor Laboratory, and Ausubel, et al. (eds. 1987 and periodic supplements) *Current Protocols in Molecular Biology*, Greene/Wiley, New York, which are each incorporated herein by reference. Techniques for synthesis of polypeptides are described, e.g., in Merrifield (1963) *J. Amer. Chem. Soc.* 85:2149-2156; Merrifield (1986) *Science* 232: 341-347; and Atherton, et al. (1989) *Solid Phase Peptide Synthesis: A Practical Aproach*, IRL Press, Oxford; each of which is incorporated herein by reference. See also Dawson, et al. (1994) *Science* 266:776-779 for methods to make larger polypeptides.

The term "substantially purified" as used herein refers to a molecule, such as a peptide that is substantially free of other proteins, lipids, carbohydrates, nucleic acids, or other biological materials with which it is naturally associated. For example, a substantially pure molecule, such as a polypeptide, can be at least 60%, by dry weight, the molecule of interest. One skilled in the art can purify complexes comprising the described sequences using standard protein purification methods and the purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

Changes in the amino acid sequence of the receptor components of the complex are contemplated in the present invention. The IL-7Rα or Rδ2 can be altered by changing the nucleic acid sequence encoding the proteins. Preferably, only conservative amino acid alterations are undertaken, using amino acids that have the same or similar properties. Illustrative amino acid substitutions include the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine, glutamine, or glutamate; methionine to leucine or isoleucine; phenylalanine to tyrosine, leucine or methionine; serine to threonine; threonine to serine; tryptophan to tyrosine; tyrosine to tryptophan or phenylalanine; valine to isoleucine or leucine.

Additionally, other variants and fragments of receptor complexes can be used in the present invention. Variants include analogs, homologues, derivatives, muteins, and mimetics of the receptor complexes or fragments that retain or enhance the ability to block binding between IL-B50 and a target receptor. The variants and fragments can be generated directly from sequences provided, by chemical modification, by proteolytic enzyme digestion, or by combinations thereof. Additionally, genetic engineering techniques, as well as methods of synthesizing polypeptides directly from amino acid residues, can be employed.

Non-peptide compounds that mimic the binding and function of IL-B50 ("mimetics") can be produced by the approach outlined in Saragovi, et al. (1991) *Science* 253:792-95. Mimetics are molecules which mimic elements of protein secondary structure. See, e.g., Johnson et al., "Peptide Turn Mimetics," in Pezzuto, et al. (eds. 1993) *Biotechnology and Pharmacy*, Chapman and Hall, New York. The underlying rationale behind the use of peptide mimetics is that the peptide backbone of proteins exists chiefly to orient amino acid side chains in such a way as to facilitate molecular interactions. For the purposes of the present invention, appropriate mimetics can be considered to be the equivalent of IL-B50 itself.

Variants and fragments also can be created by recombinant techniques employing genomic or cDNA cloning methods. Site-specific and region-directed mutagenesis techniques can be employed. See, e.g., vol. 1, ch. 8 in Ausubel, et al. (eds. 1989 and periodic updates) *Current Protocols in Molecular Biology* Wiley and Sons; and Oxender and Fox (eds.) *Protein Engineering* Liss, Inc. In addition, linker-scanning and PCR-mediated techniques can be employed for mutagenesis. See, e.g., Erlich (ed. 1989) *PCR Technology* Stockton Press. Protein sequencing, structure and modeling approaches for use with any of the above techniques are disclosed, e.g., in Oxender and Fox (eds.) *Protein Engineering* Liss, Inc; and Ausubel, et al. (eds. 1989 and periodic updates) *Current Protocols in Molecular Biology* Wiley and Sons.

This invention also contemplates the use of derivatives of IL-B50 receptor other than variations in amino acid sequence or glycosylation. Such derivatives may involve covalent or aggregative association with chemical moieties. These derivatives generally fall into three classes: (1) salts, (2) side chain and terminal residue covalent modifications, and (3) adsorption complexes, e.g., with cell membranes. Such covalent or aggregative derivatives are useful as immunogens, as reagents in immunoassays, in enhancing pharmacokinetic properties of the protein, or in purification methods such as for affinity purification of a receptor or other binding molecule, e.g., an antibody. For example, an IL-B50 receptor can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of IL-B50 receptor, antibodies, or other similar molecules. The IL-B50 can also be labeled with a detectable group, e.g., radio-iodinated by the chloramine T procedure, covalently bound to rare earth chelates, or conjugated to another fluorescent moiety for use in diagnostic assays.

A receptor complex of this invention can be used as an immunogen for the production of antisera or antibodies specific, e.g., for the complex comprising both protein components. The purified interleukin can be used to screen monoclonal antibodies or antigen-binding fragments prepared by immunization with various forms of impure preparations containing the protein. In particular, the term "antibodies" also encompasses antigen binding fragments of natural antibodies. The purified interleukin can also be used as a reagent to detect any antibodies generated in response to the presence of elevated levels of expression, or immunological disorders which lead to antibody production to the endogenous cytokine. Additionally, receptor complex fragments may also serve as immunogens to produce the antibodies of the present invention, as described immediately below. For example, this invention contemplates antibodies having binding affinity to or being raised against a complex comprising the amino acid sequences shown in FIGS. 1 and 2, fragments thereof, or homologous peptides. In particular, this invention contemplates antibodies having binding affinity to, or having been raised against, specific fragments which are predicted to be, or actually are, exposed at the exterior protein surface of the native receptor.

The blocking of physiological response to the ligand may result from the inhibition of binding of the ligand to the receptor, likely through competitive inhibition. Thus, in vitro assays of the present invention will often use antibodies or receptor binding segments of these antibodies, or fragments attached to solid phase substrates. These assays will also allow for the diagnostic determination of the effects of either binding region mutations and modifications, or receptor mutations and modifications.

This invention also contemplates the use of competitive drug screening assays, e.g., where neutralizing antibodies to the receptor complex or fragments compete with a test compound for binding. In this manner, the neutralizing antibodies or fragments can be used to detect the presence of a polypeptide which shares one or more binding sites to a receptor and can also be used to occupy binding sites on a receptor that might otherwise bind a cytokine, e.g., IL-B50.

V. Making Nucleic Acids and Protein

DNA which encodes the proteins or fragments thereof can be obtained by chemical synthesis, screening cDNA libraries, or by screening genomic libraries prepared from a wide variety of cell lines or tissue samples. Natural sequences can be isolated using standard methods and the sequences provided herein, e.g., in FIGS. 1 and 2. Other species counterparts, e.g., primate, can be identified by hybridization techniques, or by various PCR techniques, combined with or by searching in sequence databases.

These DNAs can be expressed in a wide variety of host cells for the synthesis and formation of the functional receptor complex, or fragments, which can in turn, e.g., be used to generate polyclonal or monoclonal antibodies; for binding studies; for construction and expression of modified agonist/antagonist molecules; for structure/function studies; and for screening studies. A variant or its fragments can be expressed in host cells that are transformed or transfected with appropriate expression vectors. These molecules can be substantially free of protein or cellular contaminants, other than those derived from the recombinant host, and therefore are particularly useful in pharmaceutical compositions when combined with a pharmaceutically acceptable carrier and/or diluent. The proteins, or portions thereof, may be expressed as fusions with other proteins or using combining motifs, e.g., leucine zippers, to form a soluble receptor complex.

Expression vectors are typically self-replicating DNA or RNA constructs containing the desired receptor gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention include those which contain DNA which encodes these proteins, as described, or a fragment comprising sequence from both subunits, typically encoding a functionally, e.g., biologically active, equivalent polypeptide. The DNA can be under the control of a viral promoter and can encode a selection marker. This invention further contemplates use of such expression vectors which are capable of expressing eukaryotic cDNA coding for such a protein or complex in a prokaryotic or eukaryotic host, where the vector is compatible with the host and where the eukaryotic cDNA coding for the receptor is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the receptor or its fragments in various hosts using vectors that do not contain a replication origin that is recognized by the host cell. It is also possible to use vectors that cause integration of the protein encoding portion or its fragments into the host DNA by recombination, e.g., downstream of heterologous promoters, or integration of heterologous promoters upstream from endogenous genes.

Vectors, as used herein, comprise plasmids, viruses, bacteriophage, integratable DNA fragments, and other vehicles, e.g., which may enable the integration of DNA fragments into the genome of the host. Expression vectors are specialized vectors which contain genetic control elements that effect expression of operably linked genes. Plasmids are the most commonly used form of vector but other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y., and Rodriquez, et al. (eds. 1988) *Vectors: A Survey of Molecular Cloning Vectors and Their Uses*, Buttersworth, Boston, which are incorporated herein by reference.

Transformed cells are cells, preferably mammalian, that have been transformed, transfected, or infected with vectors, e.g., constructed using recombinant DNA techniques. Transformed host cells usually express the desired protein or its fragments, but for purposes of cloning, amplifying, and manipulating its DNA, do not need to express the subject protein. This invention further contemplates culturing transformed cells in a nutrient medium, thus permitting the cells to express the protein, including production of soluble receptor complexes or ligand.

For purposes of this invention, nucleic acid sequences are operably linked when they are functionally related to each other. For example, DNA for a pre-sequence or secretory leader is operably linked to a polypeptide if it is expressed as a pre-protein or participates in directing the polypeptide to the cell membrane or in secretion of the polypeptide. A promoter is operably linked to a coding sequence if it promotes the transcription of the polypeptide; a ribosome binding site is operably linked to a coding sequence if it is positioned to induce translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis*. Lower eukaryotes include yeasts, e.g., *S. cerevisiae* and *Pichia* species, and species of the genus *Dictyostelium*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A common vector for amplifying DNA is pBR322 or many of its derivatives. Vectors that can be used to express the receptor or its fragments include, but are not limited to, such vectors as those containing the lac promoter (pUC-series); trp promoter (pBR322-trp); lpp promoter (the pIN-series); lambda-pP or pR promoters (pOTS); or hybrid promoters such as ptac (pDR540). See Brosius, et al. (1988) "Expression Vectors Employing Lambda-, trp-, lac-, and lpp-derived Promoters", in Rodriguez and Denhardt (eds.) *Vectors: A Survey of Molecular Cloning Vectors and Their Uses*, Buttersworth, Boston, Chapter 10, pp. 205-236, which is incorporated herein by reference.

Lower eukaryotes, e.g., yeasts and *Dictyostelium*, may be transformed with IL-B50 receptor sequence containing vectors. For purposes of this invention, the most common lower eukaryotic host is the baker's yeast, *Saccharomyces cerevisiae*. It will be used to generically represent lower eukaryotes although a number of other strains and species are also available. Yeast vectors typically consist of a replication origin (unless of the integrating type), a selection gene, a promoter, DNA encoding the receptor or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells are normally the preferred host cells for expression of the functionally active interleukin protein. In principle, any higher eukaryotic tissue culture cell line is workable, e.g., insect baculovirus expression systems, whether from an invertebrate or vertebrate source. However, mammalian cells are preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama, et al. (1985) *Mol. Cell. Biol.* 5:1136-1142; pMC1neo PolyA, see Thomas, et al. (1987) *Cell* 51:503-512; and a baculovirus vector such as pAC 373 or pAC 610.

For secreted proteins, an open reading frame usually encodes a polypeptide that consists of a mature or secreted product covalently linked at its N-terminus to a signal peptide. The signal peptide is typically cleaved prior to secretion of the mature, or active, polypeptide. The cleavage site can be predicted with a high degree of accuracy from empirical rules, e.g., von-Heijne (1986) *Nucleic Acids Research* 14:4683-4690, and the precise amino acid composition of the signal peptide does not appear to be critical to its function. See, e.g., Randall, et al. (1989) *Science* 243:1156-1159; and Kaiser et al. (1987) *Science* 235:312-317.

It will often be desired to express these polypeptides in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the receptor genes may be co-transformed with one or more genes encoding mammalian or other glycosylating enzymes. Using this approach, certain mammalian glycosylation patterns will be achievable in prokaryote or other cells.

The source of receptor complex can be a eukaryotic or prokaryotic host expressing recombinant receptor subunit DNA, such as is described above. The source can also be a cell line such as mouse Swiss 3T3 fibroblasts, but other mammalian cell lines are also contemplated by this invention, with the preferred cell line being from the human species.

Now that the entire sequence and components of the functional receptor complex is known, the human receptor complex, fragments, or derivatives thereof can be prepared by conventional processes for synthesizing peptides. These include processes such as are described in Stewart and Young (1984) *Solid Phase Peptide Synthesis*, Pierce Chemical Co., Rockford, Ill.; Bodanszky and Bodanszcy (1984) *The Practice of Peptide Synthesis*, Springer-Verlag, New York; and Bodanszky (1984) *The Principles of Peptide Synthesis*, Springer-Verlag, New York; all of each which are incorporated herein by reference. For example, an azide process, an acid chloride process, an acid anhydride process, a mixed anhydride process, an active ester process (e.g., p-nitrophenyl ester, N-hydroxysuccinimide ester, or cyanomethyl ester), a carbodiimidazole process, an oxidative-reductive process, or a dicyclohexylcarbodiimide (DCCD)/additive process can be used. Solid phase and solution phase syntheses are both applicable to the foregoing processes.

The receptor subunit proteins, fragments, or derivatives are suitably prepared in accordance with the above processes as typically employed in peptide synthesis, generally either by a so-called stepwise process which comprises condensing an amino acid to the terminal amino acid, one by one in sequence, or by coupling peptide fragments to the terminal amino acid. Amino groups that are not being used in the coupling reaction typically must be protected to prevent coupling at an incorrect location.

If a solid phase synthesis is adopted, the C-terminal amino acid is bound to an insoluble carrier or support through its carboxyl group. The insoluble carrier is not particularly limited as long as it has a binding capability to a reactive carboxyl group. Examples of such insoluble carriers include halomethyl resins, such as chloromethyl resin or bromomethyl resin, hydroxymethyl resins, phenol resins, tert-alkyloxycarbonylhydrazidated resins, and the like.

An amino group-protected amino acid is bound in sequence through condensation of its activated carboxyl group and the reactive amino group of the previously formed peptide or chain, to synthesize the peptide step by step. After synthesizing the complete sequence, the peptide is split off from the insoluble carrier to produce the peptide. This solid-phase approach is generally described by Merrifield, et al. (1963) in *J. Am. Chem. Soc.* 85:2149-2156, which is incorporated herein by reference.

The prepared proteins and fragments thereof can be isolated and purified from the reaction mixture by means of peptide separation, e.g., by extraction, precipitation, electrophoresis, various forms of chromatography, and the like. The receptors of this invention can be obtained in varying degrees of purity depending upon its desired use. Purification can be accomplished by use of the protein purification techniques disclosed herein, see below, or by the use of the antibodies herein described in methods of immunoabsorbant affinity chromatography. This immunoabsorbant affinity chromatography is typically carried out by first linking the antibodies to a solid support and then contacting the linked antibodies with solubilized lysates of appropriate cells, lysates of other cells expressing the receptor complexes, or lysates or supernatants of cells producing the proteins as a result of DNA techniques, see below.

Generally, the purified protein will be at least about 40% pure, ordinarily at least about 50% pure, usually at least about 60% pure, typically at least about 70% pure, more typically at least about 80% pure, preferable at least about 90% pure and more preferably at least about 95% pure, and in particular embodiments, 97%-99% or more. Purity will usually be on a weight basis, but can also be on a molar basis. Different assays will be applied as appropriate.

VI. Antibodies

The term "antibody" or "antibody molecule" as used in this invention includes intact molecules as well as fragments thereof, such as Fab, F(ab')$_2$, and Fv which are capable of selectively binding the epitopic determinant. These antibody fragments retain some ability to selectively bind with its antigen or receptor and are defined as follows: (1) Fab, the fragment which contains a monovalent antigen-binding fragment of an antibody molecule can be produced by digestion of whole antibody with the enzyme papain to yield an intact light chain and a portion of one heavy chain; (2) Fab', the fragment of an antibody molecule can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')$_2$ is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. See, e.g., Harlow and Lane (current edition) *Antibodies: A Laboratory Manual*, Cold Spring Harbor Laboratory, New York. Therefore, the phrase "antibody molecule" in its various forms as used herein contemplates both an intact antibody (immunoglobulin) molecule and an immunologically active portion of an antibody (immunoglobulin) molecule. Recombinant methods may be applied to make these fragments.

The term "monoclonal antibody" refers to a population of one species of antibody molecule of antigen-specificity. A monoclonal antibody contains only one species of antibody combining site capable of immunoreacting with a particular antigen and thus typically displays a single binding affinity for that antigen. A monoclonal antibody may therefore contain a bispecific antibody molecule having two antibody combining sites, each immunospecific for a different antigen. In one embodiment, the first antibody molecule is affixed to a solid support.

As used in this invention, the term "epitope" means an antigenic determinant on an antigen to which the paratope of an antibody binds. Epitopic determinants usually consist of chemically active surface groupings such as amino acids or sugar side chains and usually have specific three dimensional structural characteristics, as well as specific charge characteristics.

The word "complex" as used herein refers to the product of a specific binding agent-target reaction. An exemplary complex is the combination of two subunits to form a physiological complex of protein subunits, or an immunoreaction product formed by an antibody-antigen reaction.

The term "antigen" refers to a polypeptide or protein that is able to specifically bind to (immunoreact with) an antibody and form an immunoreaction product (immunocomplex). The site on the antigen with which the antibody binds is referred to as an antigenic determinant or epitope, and the binding should be detectable, e.g., 2×, 5× or more above background.

A method of the invention for detection of antibodies that bind to novel epitopes in a sample is performed in vitro, e.g., in immunoassays in which the antibodies can be identified in liquid phase or bound to a solid phase carrier. In various embodiments, the method is performed with a capture antibody bound to a solid support, and/or the capture antibody is a monoclonal antibody molecule. In other instances, the use of tetramer technology may be useful. See, e.g., Kelleher and Rowland-Jones (2000) *Curr. Op. Immunol.* 12:370-374; Katz (1999) *Biomol. Eng.* 16:57-65; and Ogg and McMichael (1998) *Curr. Op. Immunol.* 10:393-396.

Examples of types of immunoassays which can be utilized to detect novel antibodies in a sample, include competitive and non-competitive immunoassays in either a direct or indirect format. Examples of such immunoassays are the radioimmunoassay (RIA) and the sandwich (immunometric) assay. Detection of the antibodies can be done utilizing immunoassays which are run in either the forward, reverse, or simultaneous modes, including competition immunoassays and immunohistochemical assays on physiological samples. Preferably, the method of the invention utilizes a forward immunoassay. Those of skill in the art will know, or can readily discern, other immunoassay formats without undue experimentation.

Solid phase-bound antibody molecules are bound by adsorption from an aqueous medium, although other modes of affixation, such as covalent coupling or other well known means of affixation to the solid matrix can be used. Preferably, the first antibody molecule is bound to a support before forming an immunocomplex with antigen, however, the immunocomplex can be formed prior to binding the complex to the solid support.

Non-specific protein binding sites on the surface of the solid phase support are preferably blocked. After adsorption of solid phase-bound antibodies, an aqueous solution of a protein free from interference with the assay such as bovine, horse, or other serum albumin that is also free from contamination with the antigen is admixed with the solid phase to adsorb the admixed protein onto the surface of the antibody-containing solid support at protein binding sites on the surface that are not occupied by the antibody molecule.

A typical aqueous protein solution contains about 2-10 weight percent bovine serum albumin in PBS at a pH of about 7-8. The aqueous protein solution-solid support mixture is typically maintained for a time period of at least one hour at a temperature of about 4-37 degrees C. and the resulting solid phase is thereafter rinsed free of unbound protein.

The first preselected antibody can be bound to many different carriers and used to detect novel epitope binding antibodies in a sample. Examples of well-known carriers include glass, polystyrene, polypropylene, polyethylene, dextran, nylon, amyloses, natural and modified celluloses, polyacrylamides, agaroses, and magnetite. The nature of the carrier can be either soluble or insoluble for purposes of the invention. Those skilled in the art will know of other suitable carriers for binding antibodies, or will be able to ascertain such, using routine experimentation.

In addition, if desirable, an antibody for detection in these immunoassays can be detectably labeled in various ways. There are many different labels and methods of labeling known. Examples of the types of labels which can be used in the present invention include, e.g., enzymes, radioisotopes, fluorescent compounds, colloidal metals, chemiluminescent compounds, and bio-luminescent compounds. Many other suitable labels exist for binding to the monoclonal antibodies of the invention Antibodies which bind to IL-B50 receptor complex can be prepared using an intact polypeptide or fragments containing peptides of interest as the immunizing antigen. The polypeptide or a peptide used to immunize an animal can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the host animal, e.g., a mouse, a rat, or a rabbit.

If desired, polyclonal or monoclonal antibodies can be further purified, e.g., by binding to and elution from a matrix to which is bound the antigen to which the antibodies were raised. Many techniques are available for purification and/or concentration of polyclonal antibodies, as well as monoclonal antibodies. See, e.g., Coligan, et al. (current ed.) Unit 9, *Current Protocols in Immunology*, Wiley Interscience.

It is also possible to use the anti-idiotype antibody technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

The preparation of polyclonal antibodies is well-known to those skilled in the art. See, e.g., Green, et al. "Production of Polyclonal Antisera" pages 1-5 in Manson (ed.) *Immunochemical Protocols* Humana Press; *Production of Polyclonal Antisera in Rabbits, Rats, Mice and Hamsters* section 2.4.1 in Coligan, et al. *Current Protocols in Immunology*.

The preparation of monoclonal antibodies likewise is typically conventional. See, e.g., Kohler and Milstein (1975) *Nature* 256:495-497; Coligan, et al. *Current Protocols* sections 2.5.1-2.6.7; and Harlow and Lane (1989). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al. *Current Protocols* sections 2.7.1-2.7.12 and 2.9.1-2.9.3; Barnes, et al. in *Methods in Molecular Biology*, Humana Press.

Therapeutic applications are conceivable for the antibodies of the present invention. For example, antibodies of the present invention may also be derived from subhuman primate antibody. General techniques for raising therapeutically useful antibodies in baboons may be found, e.g., in Goldenberg, et al. (1991) WO 91/11465; and Losman, et al. (1990) *Int. J. Cancer* 46:310-314.

Alternatively, a therapeutically useful anti-IL-B50 functional receptor antibody may be derived from a "humanized" monoclonal antibody. Humanized monoclonal antibodies are produced by transferring mouse complementary determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, e.g., by Orlandi, et al. (1989) *Proc. Nat'l Acad. Sci. USA* 86:3833-3837. Techniques for producing humanized monoclonal antibodies are described, e.g., by Jones, et al. (1986) *Nature* 321:522-525; Riechmann, et al. (1988) *Nature* 332:323-327;

Verhoeyen, et al. (1988) *Science* 239:1534-1536; Carter, et al. (1992) *Proc. Nat'l Acad. Sci. USA* 89:4285-4289; Sandhu (1992) *Crit. Rev. Biotech.* 12:437-462; and Singer, et al. (1993) *J. Immunol.* 150:2844-2857.

Antibodies of the invention also may be derived from human antibody fragments isolated from a combinatorial immunoglobulin library. See, e.g., Barbas, et al. (1991) *Methods: A Companion to Methods in Enzymology*, vol. 2, page 119; and Winter, et al. (1994) *Ann. Rev. Immunol.* 12:433-465. Cloning and expression vectors that are useful for producing a human immunoglobulin phage library can be obtained, e.g., from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green, et al. (1994) *Nature Genet.* 7:13-21; Lonberg, et al. (1994) *Nature* 368:856-859; and Taylor, et al. (1994) *Int. Immunol.* 6:579-591.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a fragment denoted $F(ab')_2$. This fragment can be further cleaved using a thiol reducing agent, and optionally a blocking group for the sulfhydryl groups resulting from cleavage of disulfide linkages, to produce Fab' monovalent fragments. Alternatively, an enzymatic cleavage using papain produces two monovalent Fab fragments and an Fc fragment directly. These methods are described, e.g., by Goldenberg, U.S. Pat. No. 4,036,945 and No. 4,331,647, and references contained therein. These patents are hereby incorporated in their entireties by reference including all figures, drawings, and illustrations. See also Nisonhoff, et al. (1960) *Arch. Biochem. Biophys.* 89:230-244; Porter (1959) *Biochem. J.* 73:119-127; Edelman, et al. (1967) *Methods in Enzymology*, vol. 1, Academic Press; and Coligan, et al. *Current Protocols*, at sections 2.8.1-2.8.10 and 2.10.1-2.10.4.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent, as described in Inbar, et al. (1972) *Proc. Nat'l Acad. Sci. USA* 69:2659-2662. Alternatively, the variable chains can be linked by an intermolecular disulfide bond or cross-linked by chemicals such as glutaraldehyde. See, e.g., Sandhu (1992) *Crit. Rev. Biotech.* 12:437-462. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, e.g., by Whitlow, et al. (1991) *Methods: A Companion to Methods in Enzymology*, vol. 2, page 97; Bird, et al. (1988) *Science* 242:423-426; Ladner, et al., U.S. Pat. No. 4,946,778; Pack, et al. (1993) *Bio/Technology* 11: 1271-77; and Sandhu (1992) *Crit. Rev. Biotech.* 12:437-462.

Another form of an antibody fragment is a peptide coding for a single complementarity-determining region (CDR). CDR peptides ("minimal recognition units") can be obtained by constructing genes encoding the CDR of an antibody of interest. Such genes are prepared, e.g., by using the polymerase chain reaction to synthesize the variable region from RNA of antibody-producing cells. See, e.g., Larrick, et al. (1991) *Methods: A Companion to Methods in Enzymology*, vol. 2, page 106.

Antibodies can be raised to the various mammalian, e.g., IL-B50 receptor complex and fragments thereof, both in naturally occurring native forms and in their recombinant forms, the difference being that antibodies to the active ligand are more likely to recognize epitopes which are only present in the native conformations. Denatured antigen detection can also be useful in, e.g., Western blot analysis. Anti-idiotypic antibodies are also contemplated, which would be useful as agonists or antagonists of a natural receptor or an antibody.

A number of immunogens may be used to produce antibodies specifically reactive with receptor complex proteins. Recombinant protein is the preferred immunogen for the production of monoclonal or polyclonal antibodies. Naturally occurring protein may also be used either in pure or impure form. Synthetic peptides made using the human IL-B50 receptor protein sequences described herein may also used as an immunogen for the production of antibodies to receptor complexes. Recombinant protein can be expressed in eukaryotic or prokaryotic cells as described herein, and purified as described. The product is then injected into an animal capable of producing antibodies. Either monoclonal or polyclonal antibodies may be generated for subsequent use in immunoassays to measure the protein.

Methods of producing polyclonal antibodies are known to those of skill in the art. In brief, an immunogen, preferably a purified protein, is mixed with an adjuvant and animals are immunized with the mixture. The animal's immune response to the immunogen preparation is monitored by taking test bleeds and determining the titer of reactivity to the antigen of interest. When appropriately high titers of antibody to the immunogen are obtained, blood is collected from the animal and antisera are prepared. Further fractionation of the antisera to enrich for antibodies reactive to the protein can be done if desired. See Harlow and Lane.

Monoclonal antibodies may be obtained by various techniques familiar to those skilled in the art. Briefly, spleen cells from an animal immunized with a desired antigen are immortalized, commonly by fusion with a myeloma cell. Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. The genes encoding the derived antibodies may be subjected to mutagenesis to enhance binding affinity or pharmacokinetic properties.

Alternatively, one may isolate DNA sequences which encode a monoclonal antibody or a binding fragment thereof by screening a DNA library from human B cells according to the general protocol outlined by Huse, et al. (1989) *Science* 246: 1275-1281.

Antibodies, including binding fragments and single chain versions, against predetermined fragments of the protein can be raised by immunization of animals with conjugates of the fragments with immunogenic proteins. Monoclonal antibodies are prepared from cells secreting the desired antibody. These antibodies can be screened for binding to normal or defective protein, or screened for agonistic or antagonistic activity. These monoclonal antibodies will usually bind with at least a $K_D$ of about 1 mM, more usually at least about 300 µM, typically at least about 100 µM, more typically at least about 30 µM, preferably at least about 10 µM, and more preferably at least about 3 µM or better; including 1 µM, 300 nM, 100 nM, 30 nM, etc.

The antibodies, including antigen binding fragments, of this invention can have significant diagnostic or therapeutic value. They can be potent antagonists that bind to the receptor complex and inhibit binding to the ligand or inhibit the ability of ligand to elicit a biological response. They also can be useful as non-neutralizing antibodies and can be coupled to toxins or radionuclides to bind producing cells. Further, these antibodies can be conjugated to drugs or other therapeutic agents, either directly or indirectly by means of a linker.

The antibodies of this invention can also be useful in diagnostic applications. As capture or non-neutralizing antibodies, they can bind to the interleukin without inhibiting receptor binding. As neutralizing antibodies, they can be useful in competitive binding assays. They will also be useful in detecting or quantifying functional receptor complex. They may be used as reagents for Western blot analysis, or for immunoprecipitation or immunopurification of the respective protein.

Protein fragments may be joined to other materials, particularly polypeptides, as fused or covalently joined polypeptides to be used as immunogens. Primate receptor complex and its fragments may be fused or covalently linked to a variety of immunogens, such as keyhole limpet hemocyanin, bovine serum albumin, tetanus toxoid, etc. See *Microbiology*. Hoeber Medical Division, Harper and Row, 1969; Landsteiner (1962) *Specificity of Serological Reactions*, Dover Publications, New York; and Williams, et al. (1967) *Methods in Immunology and Immunochemistry*, Vol. 1, Academic Press, New York; each of which are incorporated herein by reference, for descriptions of methods of preparing polyclonal antisera. A typical method involves hyperimmunization of an animal with an antigen. The blood of the animal is then collected shortly after the repeated immunizations and the gamma globulin is isolated.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* (2d ed.) Academic Press, New York; and particularly in Kohler and Milstein (1975) in *Nature* 256:495-497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secrete a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275-1281; and Ward, et al. (1989) *Nature* 341:544-546, each of which is hereby incorporated herein by reference, The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant or chimeric immunoglobulins may be produced, see Cabilly, U.S. Pat. No. 4,816,567; or made in transgenic mice, see Mendez, et al. (1997) *Nature Genetics* 15:146-156. These references are incorporated herein by reference.

The antibodies of this invention can also be used for affinity chromatography in isolating primate receptor or cells expressing such. Columns can be prepared where the antibodies are linked to a solid support, e.g., particles, such as agarose, SEPHADEX, or the like, where a cell lysate may be passed through the column, the column washed, followed by increasing concentrations of a mild denaturant, whereby the purified protein will be released. Conversely, protein may be used to purify antibody.

Antibodies may also be used to screen expression libraries for particular expression products. Usually antibodies used in such a procedure will be labeled with a moiety allowing easy detection of presence of antigen by antibody binding.

Antibodies raised against an IL-B50 receptor will also be used to raise anti-idiotypic antibodies. These will be useful in detecting or diagnosing various immunological conditions related to expression of the protein or cells which express receptors for the protein. They also will be useful as agonists or antagonists of the IL-B50, which may be competitive inhibitors or substitutes for naturally occurring ligands.

Binding Composition: Receptor Protein Complex

An IL-B50 receptor that specifically binds to or that is specifically immunoreactive with an antibody, e.g., a polyclonal antibody generated against a defined immunogen, e.g., an immunogen consisting of a complex comprising both IL-7Rα and Rδ2, is typically determined in an immunoassay. Included within the present invention are those nucleic acid sequences described herein, including functional variants, that encode polypeptides that combine to bind to polyclonal antibodies generated against the prototypical primate IL-B50 receptor, but not the prior known individual components. The immunoassay typically uses a polyclonal antiserum which was raised, e.g., to a complex comprising proteins of SEQ ID NO: 2 and 4. This antiserum is selected to have low crossreactivity against other IL-7 receptor family members, preferably from the same species, and to other rodent or similar evolutionarily distant receptors, so that any such cross reactivity is removed by immunoabsorption prior to use in the immunoassay.

In order to produce antisera for use in an immunoassay, the functional complex is isolated as described herein. For example, recombinant protein may be produced in a mammalian cell line. An appropriate host, e.g., an inbred strain of mice such as Balb/c, is immunized with the complex using a standard adjuvant, such as Freund's adjuvant, and a standard mouse immunization protocol (see Harlow and Lane). Alternatively, a synthetic peptide derived from the sequences disclosed herein and conjugated to a carrier protein can be used as an immunogen. Polyclonal sera are collected, perhaps immunodepleted, and titered against the immunogen protein in an immunoassay, e.g., a solid phase immunoassay with the immunogen immobilized on a solid support. Polyclonal antisera with a titer of $10^4$ or greater are selected and tested for their cross reactivity against other IL-7 receptor family members, e.g., using a competitive binding immunoassay such as the one described in Harlow and Lane, supra, at pages 570-573. Preferably at least two IL-7 receptor family members are used in this determination. These IL-7 receptor family members can be produced as recombinant proteins and isolated using standard molecular biology and protein chemistry techniques as described herein.

Immunoassays in the competitive binding format can be used for the crossreactivity determinations. For example, the receptor complex, soluble or membrane associated, can be immobilized to a solid support. Proteins added to the assay compete with the binding of the antisera to the immobilized antigen. The ability of the above proteins to compete with the binding of the antisera to the immobilized complex is compared to the other family members. The percent crossreactivity for the above proteins is calculated, using standard calculations. Those antisera with less than 10% crossreactivity with each of the proteins listed above are selected and pooled. The cross-reacting antibodies are then removed from the pooled antisera by immunoabsorption with the above-listed proteins.

The immunoabsorbed and pooled antisera are then used in a competitive binding immunoassay as described above to compare a second protein complex to the immunogen protein complex. In order to make this comparison, the two proteins are each assayed at a wide range of concentrations and the amount of each protein required to inhibit 50% of the binding of the antisera to the immobilized protein is determined. If the amount of the second protein required is less than twice the amount of the antigen receptor complex that is required, then the second protein is said to specifically bind to an antibody generated to the immunogen.

VII. Kits and Quantitation

Both naturally occurring and recombinant forms of the receptor complex of this invention are particularly useful in kits and assay methods. For example, these methods would also be applied to screening for binding activity, e.g., ligands or antagonists for these receptors. Several methods of automating assays have been developed in recent years so as to permit screening of tens of thousands of compounds per year. See, e.g., a BIOMEK automated workstation, Beckman Instruments, Palo Alto, Calif., and Fodor, et al. (1991) *Science* 251:767-773, which is incorporated herein by reference. The latter describes means for testing binding by a plurality of defined polymers synthesized on a solid substrate. The development of suitable assays to screen for an agonist/antagonist or ligand-like proteins can be greatly facilitated by the availability of large amounts of purified, soluble receptor complexes in an active state such as is provided by this invention.

Purified receptor complexes can be attached to substrates for use in the aforementioned screening techniques. However, non-neutralizing antibodies to these receptors can be used as capture antibodies to immobilize the respective receptor complexes on the solid phase, useful, e.g., in diagnostic uses.

This invention also contemplates use of receptor complexes, fragments thereof, peptides, and their fusion products in a variety of diagnostic kits and methods for detecting the presence of the receptor. Alternatively, or additionally, antibodies against the molecules may be incorporated into the kits and methods. Typically the kit will have a compartment containing either a defined peptide or gene segment or a reagent which recognizes one or the other. Typically, recognition reagents, in the case of peptide, would be a ligand or antibody, or in the case of a gene segment, would usually be a hybridization probe.

A preferred kit for determining the concentration of, e.g., receptor complex, a sample would typically comprise a labeled compound, e.g., IL-B50 or antibody, having known binding affinity for receptor, a source of receptor (naturally occurring or recombinant) as a positive control, and a means for separating the bound from free labeled compound, e.g., a solid phase for immobilizing the receptor in the test sample. Compartments containing reagents, and instructions, will normally be provided.

Antibodies, including antigen binding fragments, specific for mammalian receptor complex or a peptide fragment, or ligand are useful in diagnostic applications to detect the presence of elevated levels of receptor and/or its fragments. Diagnostic assays may be homogeneous (without a separation step between free reagent and antibody-antigen complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SL-FIA) and the like. For example, unlabeled antibodies can be employed by using a second antibody which is labeled and which recognizes the antibody to receptor complex or to a particular fragment thereof. These assays have also been extensively discussed in the literature. See, e.g., Harlow and Lane (1988) *Antibodies: A Laboratory Manual*, CSH., and Coligan (ed. 1991 and periodic supplements) *Current Protocols In Immunology* Greene/Wiley, New York.

Anti-idiotypic antibodies may have similar use to serve as agonists or antagonists of receptor. These should be useful as therapeutic reagents under appropriate circumstances.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled ligand is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent, and will contain instructions for proper use and disposal of reagents. Desirably, the reagents are provided as a dry lyophilized powder, where the reagents may be reconstituted in an aqueous medium having appropriate concentrations for performing the assay.

Many of the aforementioned constituents of the diagnostic assays may be used without modification or may be modified in a variety of ways. For example, labeling may be achieved by covalently or non-covalently joining a moiety which directly or indirectly provides a detectable signal. In any of these assays, a test compound, receptor complex, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both patents are incorporated herein by reference. Possibilities for indirect labeling include biotinylation of one constituent followed by binding to avidin coupled to one of the above label groups.

There are also numerous methods of separating the bound from the free ligand, or alternatively the bound from the free test compound. The receptor complex can be immobilized on various matrixes followed by washing. Suitable matrices include plastic such as an ELISA plate, filters, and beads. Methods of immobilizing the receptor to a matrix include, without limitation, direct adhesion to plastic, use of a capture antibody, chemical coupling, and biotin-avidin. The last step in this approach involves the precipitation of antibody/antigen complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30(9):1457-1461, and the double antibody magnetic particle separation as described in U.S. Pat. No. 4,659,678, each of which is incorporated herein by reference.

The methods for linking protein or fragments to various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequences of these primate receptor subunits. These sequences can be used as probes for detecting levels of the receptors in patients suspected of having an immunological disorder, or to evaluate polymorphic variation. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein duplexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89-97.

VII. Therapeutic Utility

This invention provides reagents with significant therapeutic value. The receptor (naturally occurring or recombinant), fragments thereof, soluble constructs, and antibodies, along with compounds identified as having binding affinity to the receptor, are useful in the treatment of conditions exhibiting abnormal expression of the cytokine or receptor. Such abnormality will typically be manifested by immunological disorders or otherwise, as described. Additionally, this invention provides therapeutic value in various diseases or disorders associated with abnormal expression or abnormal triggering of response to the interleukin.

In addition, the expression profiles of functional receptor subunits suggests what cells should be responsive to the ligand, e.g., IL-B50. In particular, cells of the lymphoid lineage, e.g., macrophages and dendritic cells, express both subunits in sufficient stoichiometric amounts to form functional complexes. In particular, since the IL-7Rα is shared with the IL-7 ligand, it would be expected that much of the signaling pathway will be very similar to IL-7. Thus, much of the biology of the same cells will be closely related. In contrast, the expression of the IL-B50 receptor subunits in different cell types suggests that signaling to those cell types occurs, and will have effects on the physiology effected by such cell types. An antagonist, mutein or antibody, could prove very useful in those situations. See Rich (ed.) *Clinical Immunology: Principles and Practice*, Mosby.

T helper cells mediate effector functions in infectious, allergic, or autoimmune diseases through production of cytokines. CD4+ T cells can be divided into Th1 and Th2 subsets on the basis of their cytokine profile upon antigen stimulation. Evidence has recently been obtained that Th1 and Th2 cells differ in responsiveness and receptor expression. The linkage via TARC expression in response to IL-B50, and production of Th2 type cytokines suggests effect on Th2 responses. The expression profile of the proteins here described indicates that IL-B50 is the ligand for functional receptor complex and, as such, could be important for Th2 effector functions.

Recombinant soluble receptor may be useful as an antagonist, antibodies against the receptor subunits or complex, or IL-B50 antibodies or cytokine muteins can be purified and then administered to a patient. These reagents can be combined for therapeutic use with additional active ingredients, e.g., in conventional pharmaceutically acceptable carriers or diluents, along with physiologically innocuous stabilizers and excipients. These combinations can be sterile, e.g., filtered, and placed into dosage forms as by lyophilization in dosage vials or storage in stabilized aqueous preparations. This invention also contemplates use of antibodies or binding fragments thereof which are not complement binding.

Further analysis can be performed to identify additional molecules involved in the receptor to the cytokine, e.g., additional receptor subunits. Subsequent biological assays can then be utilized to determine if those additional receptor components can affect signal transduction, which can block provide means to further address mechanisms or structures in the signaling pathways. Receptor fragments, e.g., soluble receptor constructs, or ligand muteins can be used as a blocker or antagonist which blocks the activity of IL-B50. Conversely, a compound having intrinsic stimulating activity can activate the receptor and is thus an agonist in that it simulates the activity of IL-B50. This invention further contemplates the therapeutic use of antibodies to the receptor as agonists.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds. 1990) *Goodman and Gilman's: The Pharmacological Bases of Therapeutics,* 8th Ed., Pergamon Press; and *Remington's Pharmaceutical Sciences*, (current ed.), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 μM concentrations, usually less than about 100 mM, preferably less than about 10 pM (picomolar), and most preferably less than about 1 fM (femtomolar), with an appropriate carrier. Slow release formulations, or slow release apparatus will often be utilized for continuous administration.

Receptor subunits, complexes of subunits, fragments thereof, and antibodies or their fragments, antagonists, and agonists, or vectors encoding any of the mentioned entities may be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations comprise at least one active ingredient, as defined above, together with one or more acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds. 1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa.; Avis, et al. (eds. 1993) *Pharmaceutical Dosage Forms: Parenteral Medications* Dekker, NY; Lieberman, et al. (eds. 1990) *Pharmaceutical Dosage Forms: Tablets* Dekker, NY; and Lieberman, et al. (eds. 1990) *Pharmaceutical Dosage Forms: Disperse Systems* Dekker, NY.

Another therapeutic approach included within the invention involves direct administration of reagents or compositions by any conventional administration techniques (e.g., but not restricted to local injection, inhalation, or administered systemically), to the subject with an appropriate medical disorder. The reagent, formulation, or composition may also be targeted to specific cells or receptors by methods described herein. The actual dosage of reagent, formulation or composition that modulates an inflammatory disorder depends on many factors, including the size and health of an organism. See, e.g., Spilker (1984) *Guide to Clinical Studies and Developing Protocols*, Raven Press, New York, particularly pages 7-13, 54-60; Spilker (1991) *Guide to Clinical Trials*, Raven Press, New York, especially pages 93-101; Craig and Stitzel (eds. 1986) *Modern Pharmacology* 2d ed., Little, Brown, Boston, especially pages 127-33; Speight (ed. 1987) *Avery's Drug Treatment: Principles and Practice of Clinical Pharmacology and Therapeutics*, 3d ed., Williams and Wilkins, Baltimore, pages 50-56; and Tallarida, et al. (1988) *Principles in General Pharmacology*, Springer-Verlag, New York, pages 18-20; which describes how to determine the appropriate dosage. Generally, doses in the range of between about 0.5 ng/ml and 500 μg/ml inclusive final concentration are administered per day to an adult in a pharmaceutically-acceptable carrier. The therapy of this invention may be combined with or used in association with other therapeutic agents directed to the indicated conditions, particularly agonists or antagonists of other IL-7 family members.

The IL-B50 receptor complex forms the basis for antagonist drug development (e.g., humanized anti-human receptor antibodies). IL-B50 may form an integral part of the lymphoid lineage immune defense. The IL-B50 appears to signal through the STAT3 and STAT5 molecule pathways.

The broad scope of this invention is best understood with reference to the following examples, which are not intended to limit the inventions to the specific embodiments.

The terms and expressions which have been employed are used as terms of description and not of limitation. It is recognized that various modifications are possible within the scope of the invention claimed. Thus, it should be understood that although the present invention has been specifically disclosed by preferred embodiments and optional features, modification and variation of the concepts herein disclosed may be used by those of ordinary skill in the art, and that such modifications and variations are considered to be within the scope of this invention as defined by the appended claims.

EXAMPLES

I. General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual*, (2d ed.), vols 1-3, CSH Press, NY; Ausubel, et al., *Biology*, Greene Publishing Associates, Brooklyn, N.Y.; or Ausubel, et al. (1987 and Supplements) *Current Protocols in Molecular Biology*, Greene/Wiley, New York. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Meth. Enzymol.*, vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische*

*Industrie* 12:69-70; Hochuli (1990) "Purification of Recombinant Proteins with Metal Chelate Absorbent" in Setlow (ed.) *Genetic Engineering. Principle and Methods* 12:87-98, Plenum Press, N.Y.; and Crowe, et al. (1992) *QIAexpress: The High Level Expression & Protein Purification System* QIAGEN, Inc., Chatsworth, Calif.

Computer sequence analysis is performed, e.g., using available software programs, including those from the GCG (U. Wisconsin) and GenBank sources. Public sequence databases were also used, e.g., from GenBank and others.

Many techniques applicable to the IL-10 receptor may be applied to IL-7Rα and/or Rδ2, as described, e.g., in U.S. Pat. No. 5,985,828, which is incorporated herein by reference for all purposes.

II. Amplification of Receptor Fragments by PCR

Cloning of human receptors is performed by standard procedures. Various methods of amplifying target sequences, such as the polymerase chain reaction, can also be used to prepare DNA encoding these receptor proteins or polypeptides. Polymerase chain reaction (PCR) technology is used to amplify such nucleic acid sequences directly from mRNA, from cDNA, and from genomic libraries or cDNA libraries. This allows for diagnostic methods which allow determination of polymorphic or populational variety, may of which might affect physiology or function of the resulting gene product. Such may allow predictive information to be gathered to diagnose disease or predict therapeutic response.

In PCR techniques, oligonucleotide primers complementary to two 5' regions in the DNA region to be amplified are synthesized. The polymerase chain reaction is then carried out using the two primers. See Innis et al. (current eds.) *PCR Protocols: A Guide to Methods and Applications* Academic Press, San Diego, Calif. Primers can be selected to amplify the entire regions encoding full-length receptor proteins or to amplify smaller DNA segments as desired. Once such regions are PCR-amplified, they can be sequenced and oligonucleotide probes can be prepared from sequence obtained using standard techniques.

Oligonucleotides for use as probes are chemically synthesized according to the solid phase phosphoramidite triester method first described by Beaucage and Carruthers (1983) *Tetrahedron Lett.* 22(20): 1859-1862, or using an automated synthesizer, as described in Needham-VanDevanter et al. (1984) *Nucleic Acids Res.* 12: 6159-6168. Purification of oligonucleotides is performed, e.g., by native acrylamide gel electrophoresis or by anion-exchange HPLC as described in Pearson and Regnier (1983) *J. Chrom.* 255: 137-149. The sequence of the synthetic oligonucleotide can be verified using the chemical degradation method of Maxam and Gilbert in Grossman and Moldave (eds. 1980) *Methods in Enzymology* 65:499-560 Academic Press, New York.

The peptide segments, along with comparison to homologous genes, can also be used to produce appropriate oligonucleotides to screen a library. The genetic code can be used to select appropriate oligonucleotides useful as probes for screening. In combination with polymerase chain reaction (PCR) techniques, synthetic oligonucleotides will be useful in selecting desired clones from a library Complementary sequences will also be used as probes or primers. Based upon identification of the likely amino terminus, other peptides should be particularly useful, e.g., coupled with anchored vector or poly-A complementary PCR techniques or with complementary DNA of other peptides.

To identify a homologous receptor protein, degenerate oligonucleotides are designed. The primers are used for polymerase chain reactions on, e.g., genomic DNA followed by subcloning the PCR products using restriction sites placed at the 5' ends of the primers, picking individual *E. coli* colonies carrying these subcloned inserts, and using a combination of random sequencing and hybridization analysis to eliminate other known family members.

Subsequently, PCR products are gel-purified, digested with appropriate restriction enzymes, gel-purified again, and subcloned in the Bluescript vector (Stratagene, San Diego, Calif.). Bacterial colonies carrying individual subclones are picked into 96 well microtiter plates, and multiple replicas are prepared by plating the cells onto nitrocellulose. The replicate filters are hybridized to probes representing known members of the IL-7 receptor family, and DNA is prepared from non-hybridizing colonies for sequence analysis.

Two appropriate forward and reverse primers are selected using the sequences supplied herein (see FIGS. 1 and 2) and common knowledge. See, e.g., Innis, et al. (current eds.) *PCR Protocols: A Guide to Methods and Applications* Academic Press, San Diego, Calif.; and Dieffenbach and Dveksler (current eds.) *PCR Primer: A Laboratory Manual* Cold Spring Harbor Press, CSH, NY. RT-PCR is used on an appropriate mRNA sample selected for the presence of message to produce a cDNA, e.g., a monocyte or macrophage cell sample.

Full length clones may be isolated by hybridization of cDNA libraries from appropriate tissues pre-selected by PCR signal.

As is commonly known, PCR primers are typically designed to contain at least 15 nucleotides, e.g., 15-30 nucleotides. The design of specific primers containing 21 nucleotides, e.g., that code for the appropriate polypeptides containing at least 4 amino acids from the IL7Rα or Rδ2 sequences are described as follows. Other PCR primers designed to amplify other receptor polypeptide fragments will be designed in a similar fashion, e.g., mutagenesis primers. Preferably, most or all of the nucleotides in such a primer encode conserved amino acids, e.g., amino acid residues of SEQ ID NO: 2 or 4. For example, primers containing at least 40% IL-7Rα or Rδ2 conserved amino acids can be used. Once appropriate amino acids are selected as templates against which primer sequences are to be designed, the primers can be synthesized using, e.g., standard chemical methods. Due to the degeneracy of the genetic code and the bias of preferred species variants, such primers should be designed to include appropriate degenerate sequences, as can be readily determined using common knowledge.

III. Tissue Distribution of IL-7Rα or Rδ2

Message for the gene encoding IL-7Rα has been detected in a human cDNA library, in dendritic cells and monocytes. Message for Rδ2 has been detected in dendritic cells, monocytes, NK, and some T cells. Both are found in certain DC and certain monocyte samples, indicating that the components of functional receptors are on those cells.

Southern Analysis: DNA (5 μg) from a primary amplified cDNA library is digested with appropriate restriction enzymes to release the inserts, run on a 1% agarose gel and transferred to a nylon membrane (Schleicher and Schuell, Keene, N.H.).

Samples for human mRNA isolation could include: peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot 72, activated with anti-CD28 and anti-CD3 for 3, 6, 12 h pooled (T103); T cell, TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111); T cells CD4+CD45RO-T cells polarized 27 days in anti-CD28, IL-4, and anti IFN-γ, TH2 polarized, activated with anti-CD3 and anti-CD28 4 h (T116); T cell tumor lines Jurkat and Hut78, resting (T117); T cell clones, pooled AD130.2, Tc783.12, Tc783.13, Tc783.58, Tc782.69, resting (T118); T cell random γδ T cell clones, resting (T119); Splenocytes, resting (B100); Splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); NK 20 clones pooled, resting (K100); NK 20 clones pooled, activated with PMA and ionomycin for 6 h (K101); NKL clone, derived from peripheral blood of LGL leukemia patient, IL-2 treated (K106); NK cytotoxic clone 640-A30-1, resting (K107); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFNγ, anti-IL-10 for 1, 2, 6, 12, 24 h pooled (M102); elutriated monocytes, activated with LPS, IFNγ, IL-10 for 1, 2, 6, 12, 24 h pooled (M103); elutriated monocytes, activated with LPS, IFN-γ, anti-IL-10 for 4, 16 h pooled (M106); elutriated monocytes, activated with LPS, IFNγ, IL-10 for 4, 16 h pooled (M107); elutriated monocytes, activated LPS for 1 h (M108); elutriated monocytes, activated LPS for 6 h (M109); DC 70% CD1a+, from CD34+ GM-CSF, TNFα 12 days, resting (D101); DC 70% CD1a+, from CD34+ GM-CSF, TNFα 12 days, activated with PMA and ionomycin for 1 hr (D102); DC 70% CD1a+, from CD34+ GM-CSF, TNFα 12 days, activated with PMA and ionomycin for 6 hr (D103); DC 95% CD1a+, from CD34+ GM-CSF, TNFα 12 days FACS sorted, activated with PMA and ionomycin for 1, 6 h pooled (D104); DC 95% CD14+, ex CD34+ GM-CSF, TNFα 12 days FACS sorted, activated with PMA and ionomycin 1, 6 hr pooled (D105); DC CD1a+CD86+, from CD34+ GM-CSF, TNFα 12 days FACS sorted, activated with PMA and ionomycin for 1, 6 h pooled (D106); DC from monocytes GM-CSF, IL-4 5 days, resting (D107); DC from monocytes GM-CSF, IL4 5 days, resting (D108); DC from monocytes GM-CSF, IL4 5 days, activated LPS 4, 16 h pooled (D109); DC from monocytes GM-CSF, IL-4 5 days, activated TNFα, monocyte supe for 4, 16 h pooled (D110); leiomyoma L11 benign tumor (X101); normal myometrium M5 (O115); malignant leiomyosarcoma GS1 (X103); lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102); kidney fetal 28 wk male (O100); lung fetal 28 wk male (O101); liver fetal 28 wk male (O102); heart fetal 28 wk male (O103); brain fetal 28 wk male (O104); gallbladder fetal 28 wk male (O106); small intestine fetal 28 wk male (O107); adipose tissue fetal 28 wk male (O108); ovary fetal 25 wk female (O109); uterus fetal 25 wk female (O 110); testes fetal 28 wk male (O111); spleen fetal 28 wk male (O112); adult placenta 28 wk (O113); and tonsil inflamed, from 12 year old (X100).

IV. Production of Mammalian Receptor Protein

Typically, co-expression will be useful, and constructs can be made to produce soluble receptors. This may be effected by a polycistronic construct in appropriate cells, or by construction of vectors which coexpress both receptor subunits together. Alternatively, fusion constructs can be produced, e.g., to generate antibodies.

An appropriate construct is engineered for expression, e.g., in $E.\ coli$. For example, a mouse IGIF pGex plasmid is constructed and transformed into $E.\ coli$. Freshly transformed cells are grown in LB medium containing 50 μg/ml ampicillin and induced with IPTG (Sigma, St. Louis, Mo.). After overnight induction, the bacteria are harvested and the pellets containing receptors are isolated. The pellets are homogenized in TE buffer (50 mM Tris-base pH 8.0, 10 mM EDTA and 2 mM pefabloc) in 2 liters. This material is passed through a microfluidizer (Microfluidics, Newton, Mass.) three times. The fluidized supernatant is spun down on a Sorvall GS-3 rotor for 1 h at 13,000 rpm. The resulting supernatant containing the receptor is filtered and passed over a glutathione-SEPHAROSE column equilibrated in 50 mM Tris-base pH 8.0. The fractions containing the receptor protein are pooled and cleaved with thrombin (Enzyme Research Laboratories, Inc., South Bend, Ind.). The cleaved pool is then passed over a Q-SEPHAROSE column equilibrated in 50 mM Tris-base. Fractions containing receptor are pooled and diluted in cold distilled $H_2O$, to lower the conductivity, and passed back over a fresh Q-SEPHAROSE column. Fractions containing receptor are pooled, aliquoted, and stored in the −70 degrees C. freezer.

Comparison of the CD spectrum with functional receptor may suggest that the protein is correctly folded. See Hazuda, et al. (1969) $J.\ Biol.\ Chem.$ 264:1689-1693.

Protein expression and purification of human receptor: Adenoviral vectors containing full-length human receptors are constructed by PCR and used to transfect, e.g., Q293 packaging cells. Produced viruses are subsequently purified, with all procedures according to manufacturer's protocols (Invitrogen). Receptor proteins are prepared, e.g., from $5 \times 10^8$ infected Q293 cells (adenoviruses at 10 MOI) which are subsequently incubated for 5 days in a cell factory in a total volume of 1 l of serum-free CMF-1 medium (Gibco BRL). Culture medium is dialyzed (Spectra/Por membrane tubing, MW cut off: 6-8 kD) against 50 mM Tris-HCl, pH 8.0, 1 mM EDTA, and subsequently passed over Hitrap Q sepharose and Heparin columns. The flow-through, containing the receptor proteins, is sterile-filtered and concentrated approximately 70 times using an Amicon 8400 ultrafiltration cell with a 10 kD MW cut off membrane. The samples are dialyzed against PBS, and the protein content quantified by PAGE and Coomassie Blue staining using lysozyme as a standard. Protein identities are confirmed, e.g., by N-terminal sequencing. Identically treated Q293 cells infected with adenovirus encoding green fluorescent protein provide a mock control. Endotoxin levels are determined using the $Limulus\ Amebocyte$ Lysate assay (BioWhittaker) and were less then 4 EU/ml. Protein samples are stored at 4 degrees C.

Expression vectors: For mammmalian expression, vectors encoding full-length human receptor are constructed by inserting PCR-generated cDNA fragments into pME18S. Kitamura, et al. (1991) $Proc.\ Nat'l\ Acad.\ Sci.\ USA$ 88:5082-5086.

V. Preparation of Antibodies Specific for Receptor Complex

Inbred Balb/c mice are immunized intraperitoneally with recombinant forms of the protein, e.g., purified soluble receptor-FLAG or stable transfected NIH-3T3 cells. Animals are boosted at appropriate time points with protein or cells, with or without additional adjuvant, to further stimulate antibody production. Serum is collected, or hybridomas produced with harvested spleens.

Alternatively, Balb/c mice are immunized with cells transformed with the gene or fragments thereof, either endogenous or exogenous cells, or with isolated membranes enriched for expression of the antigen. Serum is collected at the appropriate time, typically after numerous further administrations. Various gene therapy techniques may be useful, e.g., in producing protein in situ, for generating an immune response.

Monoclonal antibodies may be made. For example, splenocytes are fused with an appropriate fusion partner and hybridomas are selected in growth medium by standard procedures. Hybridoma supernatants are screened for the presence of antibodies which bind to the desired receptor, e.g., by ELISA or other assay. Antibodies which specifically recognize receptor or complex may also be selected or prepared.

In another method, synthetic peptides or purified protein are presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual* Cold Spring Harbor Press. In appropriate situations, the binding reagent is either labeled as described above, e.g., fluorescence or otherwise, or immobilized to a substrate for panning methods. Nucleic acids may also be introduced into cells in an animal to produce the antigen, which serves to elicit an immune response. See, e.g., Wang, et al. (1993) *Proc. Nat'l. Acad. Sci.* 90:4156-4160; Barry, et al. (1994) *BioTechnigues* 16:616-619; and Xiang, et al. (1995) Immunity 2: 129-135.

VI. Biological Activity of IL-B50 and Complexes with IL-7Rα and Rδ2

A number of experiments were conducted in order to assess the signaling receptor complex for IL-B50, as well as the biological function of IL-B50. In the following examples, the term "human TSLP" or "hTSLP" is used interchangeably with the term IL-B50. Additionally, the term "human TSLPR" or "hTSLPR" is used interchangeably with the term Rδ2. Materials and methods used in the following experiments were as follows.

Cell lines. Human 293T epithelial cells were maintained in Dulbecco's modified Eagle's medium (DMEM) (Life Technologies Inc.) supplemented with 10% fetal calf serum (FCS) (LTBMC). The Pro-B cell line Ba/F3 was maintained in RPMI 1640 medium (Life Technologies Inc.) supplemented with 10% fetal calf serum and 10 ng/ml of mouse IL-3. QBI-293A human embryonic kidney cells used for adenovirus expression were grown in CMF-1 medium (CellWorks, San Diego, Calif.). BOSC23 cells were maintained in DMEM-10% FCS and guanine phosphoribosyltransferase (GPT) selection reagents (Specialty Media). The cells were transferred to Dulbecco's modified Eagle's medium-10% FCS without GPT selection reagents 2 days before transfection.

Adenovirus expression of human TSLP (IL-B50) and purification of the recombinant protein. The mature coding region of human TSLP (residues 1-131 of FIG. 3) was fused to the signal sequence of mouse SLAM (Bates, et al. (1999) *J. Immunol.* 163:1973) and inserted into a modified version of transfer vector pQB1-AdCMV5-GFP (Quantum Biotechnologies Inc.) by PCR. Recombinant adenovirus was produced as described in Quantum applications manual 24AL98. Recombinant virus was used to infect $5 \times 10^8$ cells in 1 L CMF-1 with culture in a Nunc Cell Factory (Nalge Nunc Int., Naperville, Ill.) for 3 days. The culture medium was clarified by centrifugation, dialyzed and filtered prior to application to a 5 ml Q-Sepharose column. The Q-Sepharose flow-through, which contained human TSLP, was loaded onto a 5 ml HiTrap Heparin (Pharmacia, Uppsala, Sweden) column at 5 ml/min. The column was washed with 50 mM Tris-HCl pH 8.0, 1 mM EDTA, and eluted with a gradient from 0-2.5 M NaCl in 50 mM Tris-HCl pH 8.0, 1 mM EDTA. The peak fractions were concentrated, dialyzed against PBS and quantitated by SDS-PAGE and Coomassie staining using lysozyme as a standard. A similar procedure was followed to prepare mouse TSLP.

Ba/F3 retroviral-mediated gene transfer and proliferation assays. Human IL-7Rα cDNA and human TSLPR cDNA were cloned by PCR in the retroviral vectors pMX and its derivative pMX-puro to give pMX-hIL-7Rα and pMX-puro-TSLPR, respectively (Kitamura, T. (1998) *Int. J. Hematol.* 67:351). The BOSC23 packaging cell line was transiently transfected with retrovirus constructs using Fugene 6 (GIBCO BRL) according to the manufacturer protocol. Retrovirus containing supernatants were collected after two days. Ba/F3 cells were infected with retroviral supernatants for 48 hr on petri dishes coated with 40 µg/ml recombinant fibronectin fragments (Retronectin, Takara). After 48 hr puromycine (1 µg/ml) was added to those cells infected with virus obtained from pMX-puro constructs. The efficiency of infection of Ba/F3 cells was over 90% as assessed by parallel infection with the test construct pMXI-EGFP encoding the enhanced green fluorescent protein (EGFP). Proliferation assays using Ba/F cells were as previously described (Ho, et al. (1993) *Proc. Natl. Acad. Sci. USA* 90:11267). Cells were washed three times with RPMI media and plated at a density of 5000 cells/well. Cells were grown with serial threefold dilutions of mouse IL-3, human and mouse TSLP, or human IL-7 (all starting concentrations 225 ng/ml). After 36 hr at 37 degrees C. Alamar Blue® REDOX indicator (Trek Diagnostic systems) was added to a final concentration of 10% (vol/vol) to each well. Cells were allowed to grow for 5-8 more hours after which plates were measured with a fluorometer.

Quantitation of mRNA expression. cDNA libraries from various tissues and cellular sources were prepared as described previously (Bolin, et al. (1997) *J. Neurosci.* 17:5493) and used as templates for Taqman-PCR analyses. cDNAs (50 ng per reaction) were analyzed for the expression of hTSLP, hTSLPR and hIL7Rα genes by the Fluorogenic 5'-nuclease PCR assay (Holland, et al. (1991) *Proc. Natl. Acad. Sci. USA* 88:7276), using an ABI Prism 7700 Sequence Detection System (Perkin Elmer, Foster City, Calif.). Reactions were incubated for 2 min at 50 degrees C., denatured for 10 min at 95 degrees C. and subjected to 40 two-step amplification cycles with annealing/extension at 60 degrees C. for 1 min followed by denaturation at 95 degrees C. for 15 sec. The amplicons used for hTSLP, hTSLPR and IL-7Rα covered bp 246-315, bp 263-335 and bp 519-596, respectively (numbering starts at start codon), and were analyzed with FAM-labeled probes. Values were expressed as fg/50 ng total cDNA. Primers and probes for human chemokine and chemokine receptors were obtained from Perkin-Elmer as PreDeveloped Assay Reagents (PDAR's). Chemokine and chemokine receptor expression was adjusted for the amount of 18SrRNA and compared to the control (calibrator) samples using the comparative CT method (Fehniger, et al. (1999) *J. Immunol.* 162:4511). Samples were measured in duplicate. 18SrRNA levels were determined under primer limited conditions in multiplex reactions as recommended using a Vic labelled probe (Perkin Elmer, Foster City, Calif.).

Cell isolation and culture. Peripheral Blood Mononuclear Cells (PBMC) were purified from buffy coats of healthy volunteers (Stanford Blood Bank, Palo Alto, Calif.) by centrifugation over Ficoll. Human monocytes were isolated from PBMC by negative depletion using anti-CD2 (Leu-5A), anti-CD3 (Leu-4), anti-CD8 (Leu 2a), anti-CD19 (Leu-12), anti-CD20 (Leu-16), anti-CD56 (Leu-19), (BD, San Jose Calif.), anti-CD67 (IOM 67) (Immunotech, Westbrook, Me.) and anti-glycophorin A (10F7MN, ATCC, Rockville, Md.) mAbs and sheep anti-mouse IgG coupled magnetic beads (Dynal, Oslo, Norway) as described previously (Koppelman, et al. (1997) *Immunity* 7:861). Monocytes were cultured in RPMI+ 10% FCS at a density of $10^6$ cells/ml in the presence or absence of IL-7 (50 ng/ml) and/or hTSLP (50 ng/ml) for 24 hrs and culture supernatants and cells were harvested for quantitation of cytokine production or gene expression analyses. Human CD11c+dendrific cells (DC) were isolated from PBMC as previously described (Kadowaki, et al. (2000) *J. Exp. Med.* 192:219). Briefly, PBMC were incubated with anti-CD3, anti-CD14, anti-CD19, anti-CD56 mAbs, depleted from lineage+ cells using magnetic beads (Dynal) and CD11c+Lineage-blood DC were subsequently isolated by cell sorting to reach a purity of more than 99%. Freshly sorted cells were cultured in RPMI1640 containing 10% FCS at $5 \times 10^4/100$ µl in flat-bottom 96-well half-area culture plates or at $1 \times 10^5/200$ µl in flat-bottom 96-well plates, with or without IL-B50 (15 ng/ml).

TARC Elisa. The production of TARC/CCL17 in culture supernatants was determined by chemokine specific elisa using MAB364 as capture reagent and BAF364 as detection reagent (R&D Systems, Minneapolis Minn.). The sensitivity of the assay was 50 pg/ml.

DC viability and flow cytometric analysis. After 24 hours of culture, DC were harvested and resuspended in an EDTA-containing medium to dissociate the clusters. Viable DC were first counted using trypan blue exclusion of dead cells. Remaining cells were stained with a variety of mouse anti-human FITC-conjugated monoclonal antibodies (mAb) including anti-HLA-DR (Becton Dickinson), anti-CD40, anti-CD80 and CD86 (all from Pharmingen) or an Ig-G1 isotype control (Becton Dickinson), and were analyzed with a FACScan® flow cytometer (Becton Dickinson). Dead cells were excluded based on side and forward scatter characteristics.

T cell proliferation assay. Naïve CD4+/CD45RA+ T cells were isolated from adult blood buffy coats by negative depletion of cells expressing CD14, CD19, CD56, CD8, CD45RO, HLA-DR and glycophorin A using magnetic beads (Dynal). More than 95% of the purified cells had the CD4+ CD45RA+ naïve T cell phenotype. CD11c+DC were washed twice to remove any cytokine and co-cultured with $5 \times 10^4$ allogeneic naïve CD4+ T cells in round-bottom 96-well culture plates at increasing DC/T cell ratios. All co-cultures were carried out in triplicate. DC alone and T cells alone were used as controls. After 5 days, cells were pulsed with 1 µCi $^3$H-Thymidine (Amersham) for 16 hours before harvesting and counting radioactivity.

Stat3 and Stat5 activation assays. Stable Ba/F3 transfectant cells (~$2.5 \times 10^7$ cells) were starved for 4-6 hours, and then stimulated at $10^6$ cells/ml for 15 min with either 10 ng/ml of mIL-3 or 30 ng/ml of hTSLP. After stimulation, cells were harvested and incubated for 15 min at 4 degrees C. in lysis buffer containing 50 mM Tris-HCL pH 7.5, 300 mM NaCl, 2 mM EDTA, 0.875% Brij 97, 0.125% NP40, 10 mg/ml aprotinin, 10 mg/ml leupeptin, 1 mM PMSF, 1 mM Na3VO4, and 1 mM NaF. Cell lysates were clarified by centrifugation at 12,000×g for 15 min, and supernatants were subjected to 8% SDS-PAGE. Proteins were electrotransferred onto nylon membranes (Immobilon-P, Millipore, Bradford, Mass.) and detected by Western Blot analysis using rabbit Abs against anti-phospho Stat3 and anti-phospho Stat5 (New England Biolabs) or anti-Stat3 and anti-Stat5 (Santa Cruz Biotechnology), followed by mouse anti-rabbit Ig HRP. Immunoreactive bands were visualized with enhanced chemiluminescence (ECL) (SuperSignal West Dura Extended Duration Substrate, Pierce, Rockford, Ill.) on ECL film (Kodak). For reprobing, blots were stripped with 200 mM glycine, 1% SDS, pH 2.5 for 30 min at 65 degrees C.

VI.A. IL-B50 Signals via IL-7Rα and Rδ2

The cytokine human IL-B50 has as closest homologs human and mouse IL-7 and the recently described mouse TSLP (Sims, et al. (2000) *J. Expt'l Med.* 192:671-680). In mouse, both IL-7 and TSLP function as T- and B-cell growth and differentiation factors. The signaling receptor complexes for mouse IL-7 and mouse TSLP consist of two subunits, respectively mouse IL-7Rα and mouse Rγc (common receptor for IL-2, IL-4, IL-7, IL-9, and IL-15) for mouse IL-7, and mouse IL-7Rα and mouse TSLPR(Rδ1) for the mTSLP ligand (Park, et al. (2000) *J. Expt'l Med.* 192:659-670).

In an attempt to identify the signaling receptor complex for human IL-B50, Ba/F3 cells were co-transfected with expression constructs for human IL-7Rα and an orphan human cytokine receptor known as Rδ2, a subunit related to Rγc and mTSLPR(Rδ1), using the methods described above. Any functional relationship between the mTSLPR subunit Rδ1 and the human Rδ2 had been unclear. Co-transfected Ba/F3 cells showed a proliferative response in the presence of hIL-B50, but not with hIL-7 or medium. Ba/F3 cells transfected with either hIL-7Rα or hRδ2 alone did not show a proliferative response with hIL-B50. Additionally, no cross-reactivity between mTSLP and the hTSLP receptor complex was observed. These findings establish the signaling complex for human IL-B50 as consisting of hIL-7Rα and hRδ2.

The corresponding activation status of Stat5 and Stat3 was also measured in the various BaF3 cell populations. Both Stat5 and Stat3 were phosphorylated upon addition of hTSLP, but only when both hTSLPR and hIL-7Rα was present VI.B. Expression Analysis of IL-B50, hIL-7Rα and hRδ2

Figure 4E:
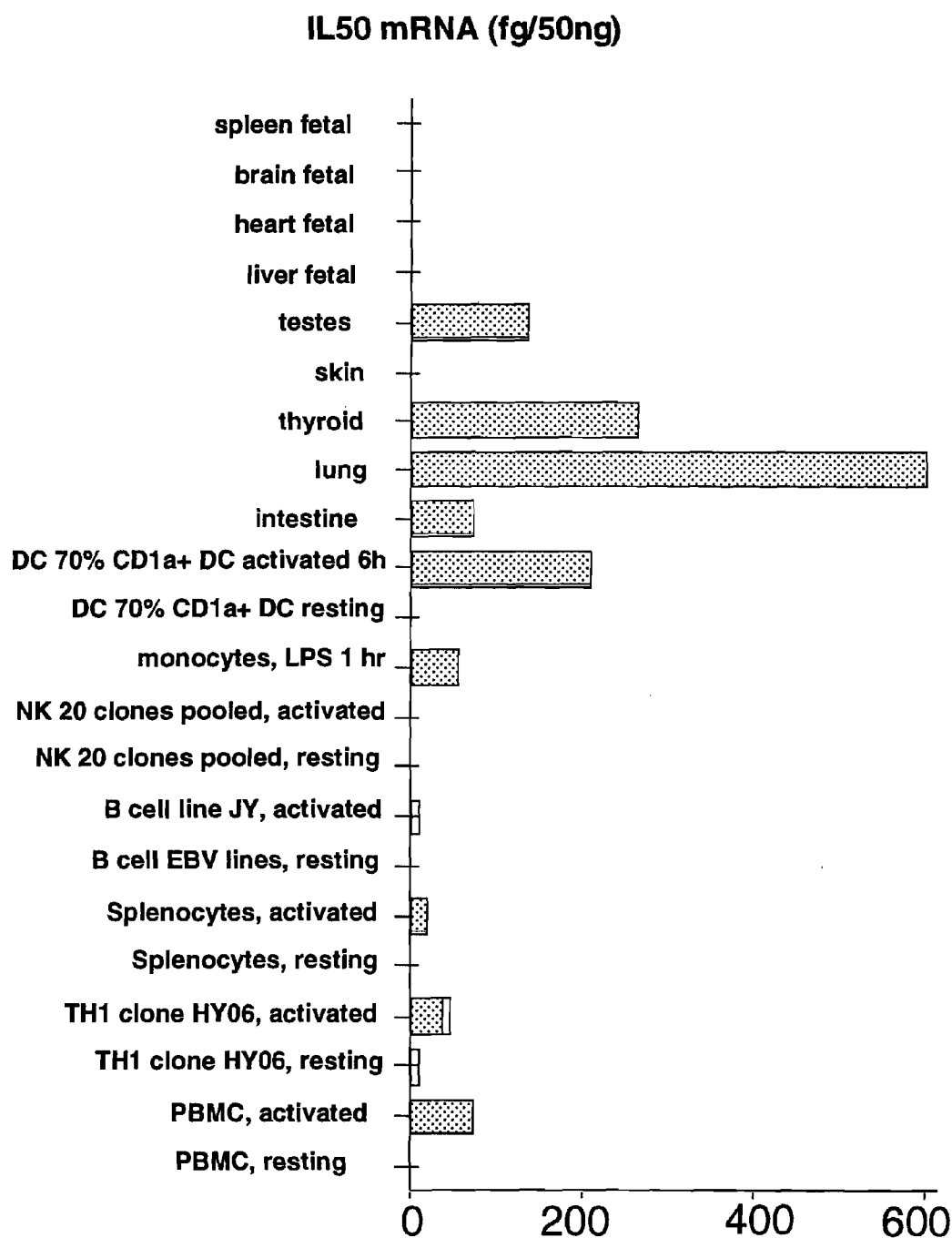

In order to identify target cells capable of responding to IL-B50888888, a large panel of cDNA libraries was analyzed for the simultaneous expression of both hIL-7Rα and hRδ2, using quatitative PCR. Results of the expression analysis, conducted as described in materials and methods, are presented in FIGS. 4A-4E. In particular, expression analysis of the two receptor subunits indicated that they were co-expressed primarily in activated dendritic cells, monocytes, and T cells (see, FIGS. 4A, 4B, 4C and 4D) indicating that these cell types respond to human IL-B50. As shown in FIG. 4E, IL-B50 was expressed in various tissue types, with high expression in the human lung.

VI.C. Human IL-B50 Induces Chemokine Expression on Freshly Isolated Monocyte Population and CD11c+Blood DC The spectrum of biological activities induced by IL-B50 was investigated based on the overlapping expression patterns of IL-B50 receptor components. cDNA was prepared from human monocytes cultured for 24 hrs in the presence of IL-B50 or IL-7, and the expression of 38 human chemokines and 20 human chemokine receptors were analyzed by quantitative "real time" PCR. Interestingly, IL-B50 (TSLP) and IL-7 influenced the expression of distinct sets of chemokines (Table 1), but did not affect the expression of chemokine receptors. IL-B50 enhanced the expression of TARC/CCL17, DC-CK1/PARC/CCL18, MDC/CCL22, and MIP3β/CL19. IL-7 also enhanced expression of TARC/CCL17, MDC/CCL22, and MIP3β/CCL19 but in addition, enhanced expression of IL-8/CXCL8, CTAPIII/CXCL7, ENA78/CXCL5, and GROabg/CXCL123 and decreased the expression levels of IP-10/CXCL10, I-TACK/CXCL11, SDF1/CXCL12, MCP2/CCL8 and MCP4/CCL13 (Table 1).

Figure 14A:
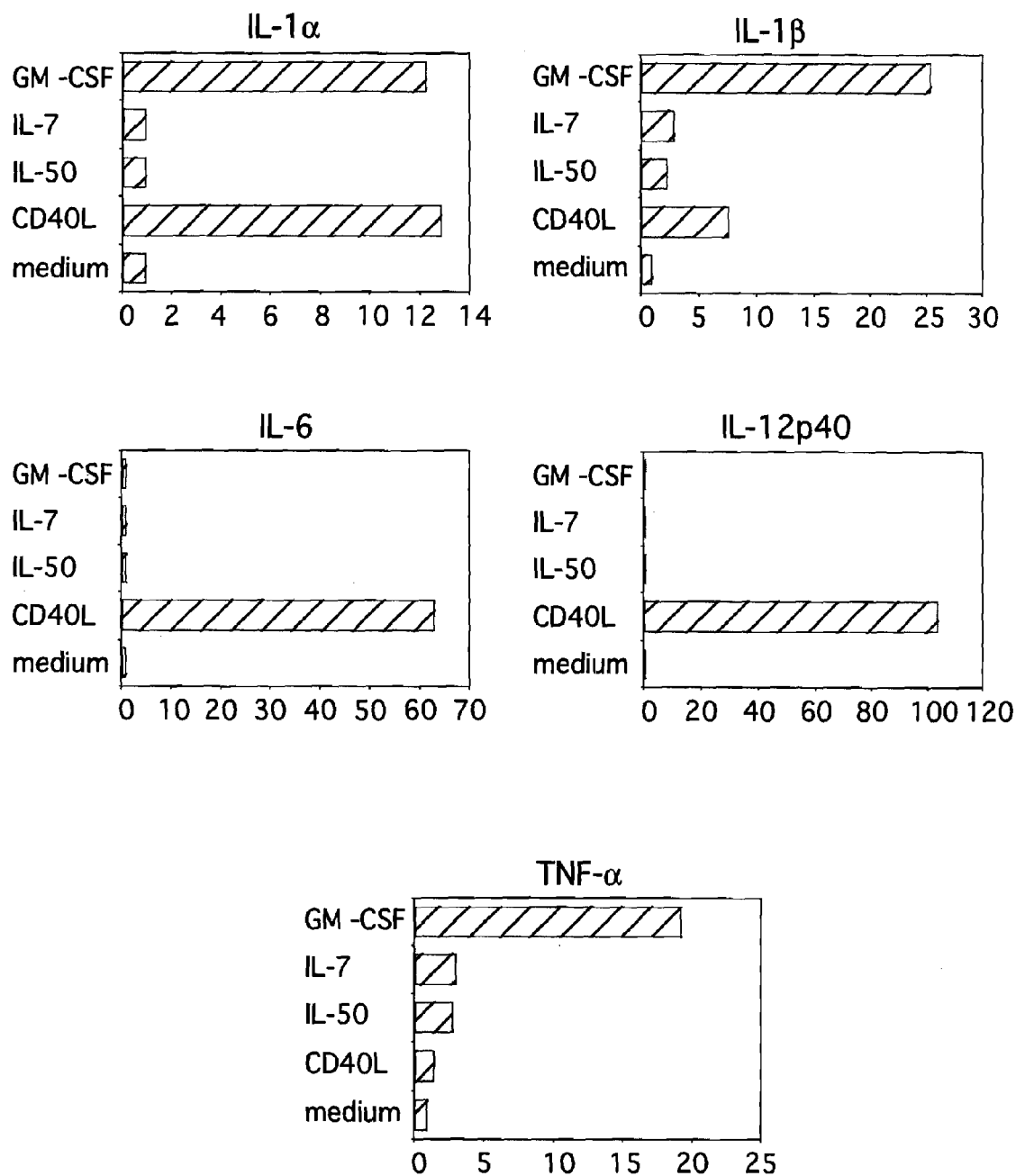

Additionally, the ability of IL-B50 to stimulate DCs to produce mRNAs for various cytokines and chemokines was compared with that of GM-CSF, IL-7, CD40-ligand (CD40L) and medium alone as a control, as follows. Purified CD11c+ DCs were cultured for 15-17 hours with IL-B50 (15 ng/ml), GM-CSF (100 ng/ml), IL-7 (50 ng/ml), CD40-ligand transfected L-cells (1 L-cell/4 DC) or medium alone. Total RNA was extracted and studied using real time quantitative PCR as described above. As shown in FIGS. 14A and 14C, IL-B50 did not stimulate human DCs to produce mRNA for IL-1α, IL-1β, IL-6, IL-12p40, TNF-α, MCP-1, MCP-4, Rantes and MIG, but did stimulate human DCs to produde mRNA for the chemokines TARC, MDC and MIP3-β (FIG. 14B).

Figure 5:
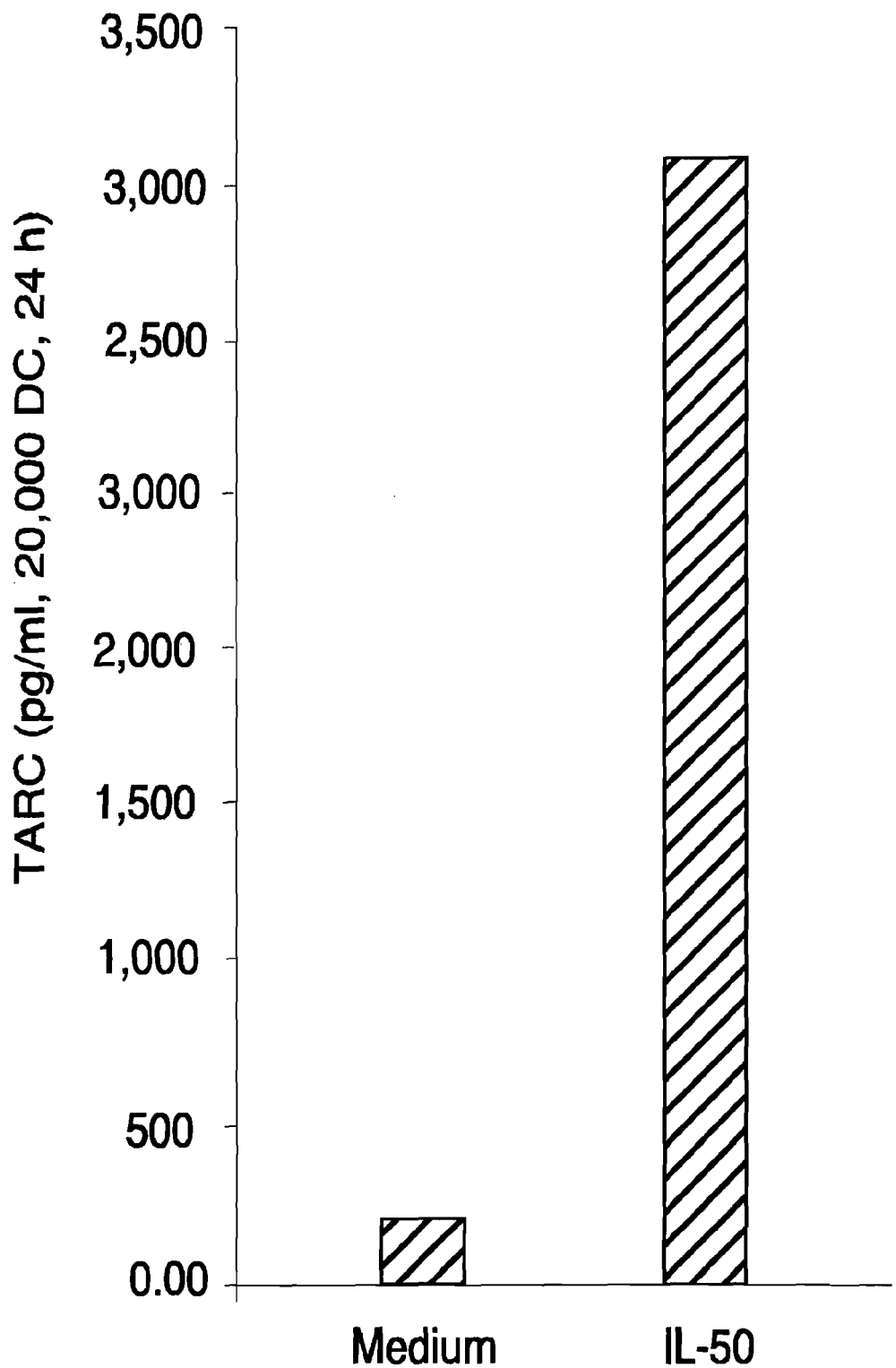
FIG. 5 shows the induction of TARC by IL-B50. Human CD11c+DC were cultured in the absence or the presence of IL-B50 (50 ng/ml) and the production of TARC was determined in the culture supernatant by ELISA.

The induction of TARC protein by IL-B50 on monocyte and dendritic cell populations was confirmed by ELISA. The level of TARC production by CD11c+dendritic cells was at least ten-fold higher than that of monocytes (FIG. 5).

Figure 15:
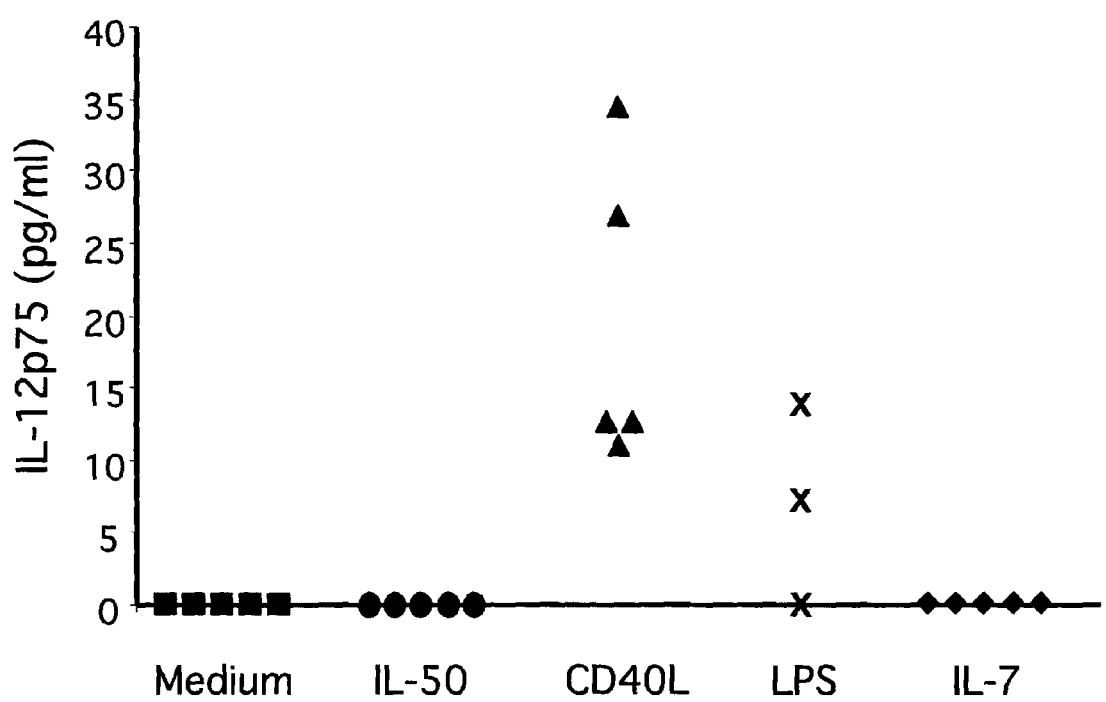
FIG. 15 shows the effect of IL-B50 on the induction of IL12p75 protein.

The induction of IL12p75 protein by IL-B50 was also examined. To do so, purified CD11c+DCs were culture for 24 hours with IL-B50 (15 ng/ml), IL-7 (50 ng/ml), CD40-ligand-transfected L-cells (1 L-cell/4 DC), bacterial lipopolysaccharide (LPS: 1 mg/ml) or medium alone. Culture supernatant was harvested and bioactive IL12p75 was measured using a high-sensitivity ELISA kit. As shown in FIG. 15, IL-B50 did not stimulate human DCs to produce IL12p75 protein.

TABLE 1

Effects of IL-B50 and IL-7 on Chemokine Expression*

| Chemokine | Media | IL-B50 | IL-7 |
|---|---|---|---|
| CCL1 | 40.0 | 1.0 | 1.4 |
| CCL2 | 24.8 | 1.0 | 1.5 |
| CCL3 | 31.5 | 0.7 | 2.0 |
| CCL4 | 28.9 | 1.0 | 1.6 |
| CCL5 | 30.4 | 1.1 | 0.6 |
| CCL7 | 31.3 | 0.7 | 1.4 |
| CCL8 | 30.2 | 0.8 | 0.2 |
| CCL11 | 40.0 | 1.6 | 1.4 |
| CCL13 | 37.3 | 1.6 | 0.1 |
| CCL14 | 40.0 | 1.3 | 1.3 |
| CCL15 | 40.0 | 1.1 | 1.3 |
| CCL16 | 40.0 | 2.2 | 7.0 |
| CCL17 | 39.8 | 195.4 | 20.1 |
| CCL18 | 35.8 | 2.9 | 1.7 |
| CCL19 | 36.7 | 8.5 | 8.3 |
| CCL20 | 40.0 | 1.2 | 1.2 |
| CCL21 | 40.0 | 1.0 | 1.0 |
| CCL22 | 34.3 | 8.8 | 3.0 |
| CCL24 | 29.3 | 2.0 | 1.2 |
| CCL25 | 40.0 | 1.1 | 1.1 |
| CCL26 | 38.9 | 1.1 | 2.5 |
| CCL27 | 40.0 | 0.8 | 1.2 |
| CCL28 | 40.0 | 1.0 | 1.0 |
| CXCL1-3 | 28.7 | 1.0 | 4.4 |
| CXCL4 | 27.9 | 1.2 | 1.9 |
| CXCL5 | 28.7 | 1.1 | 8.0 |
| CXCL6 | 40.0 | 1.5 | 1.3 |
| CXCL7 | 28.7 | 1.1 | 2.0 |
| CXCL8 | 27.3 | 1.4 | 8.5 |
| CXCL9 | 34.9 | 0.6 | 0.7 |
| CXCL10 | 29.7 | 0.6 | 0.1 |
| CXCL11 | 32.9 | 0.7 | 0.0 |
| CXCL12 | 33.1 | 0.6 | 0.2 |
| CXCL13 | 35.4 | 0.2 | 0.8 |
| CXCL14 | 39.7 | 1.0 | 1.0 |
| XCL1 | 40.0 | 0.9 | 3.8 |
| CX3CL1 | 40.0 | 1.4 | 1.3 |

*Human monocytes were cultured in the absence or presence of IL-B50 (50 ng/ml) or IL-7 (50 ng/ml) for 18 h, and expression of chemokine genes was determined by quantitative PCR. Results are expressed as 1) $C_T$ values of nonactivated samples and 2) fold difference relative to the calibrator sample (media).

VI.D. IL-B50 Activates CD11c+Dendritic Cells.

Figure 6A:
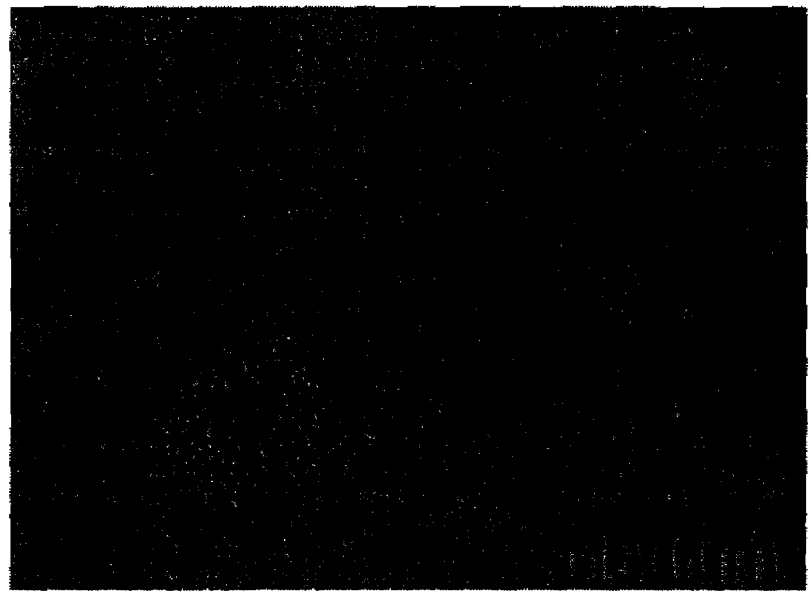
FIG. 6A depicts a culture of sorted CD11c+DC after 24 h in medium alone. DC form small and irregular clumps with a dark center, indicating the presence of dying cells.
Figure 6B:
FIG. 6B depicts a culture of sorted CD 11c+DC from the same donor as in FIG. 6A, treated with 15 ng/ml of IL-B50. DC form larger and round clumps with fine dendrites visible at the periphery, indicating the maturation of the DC.
Figure 7:
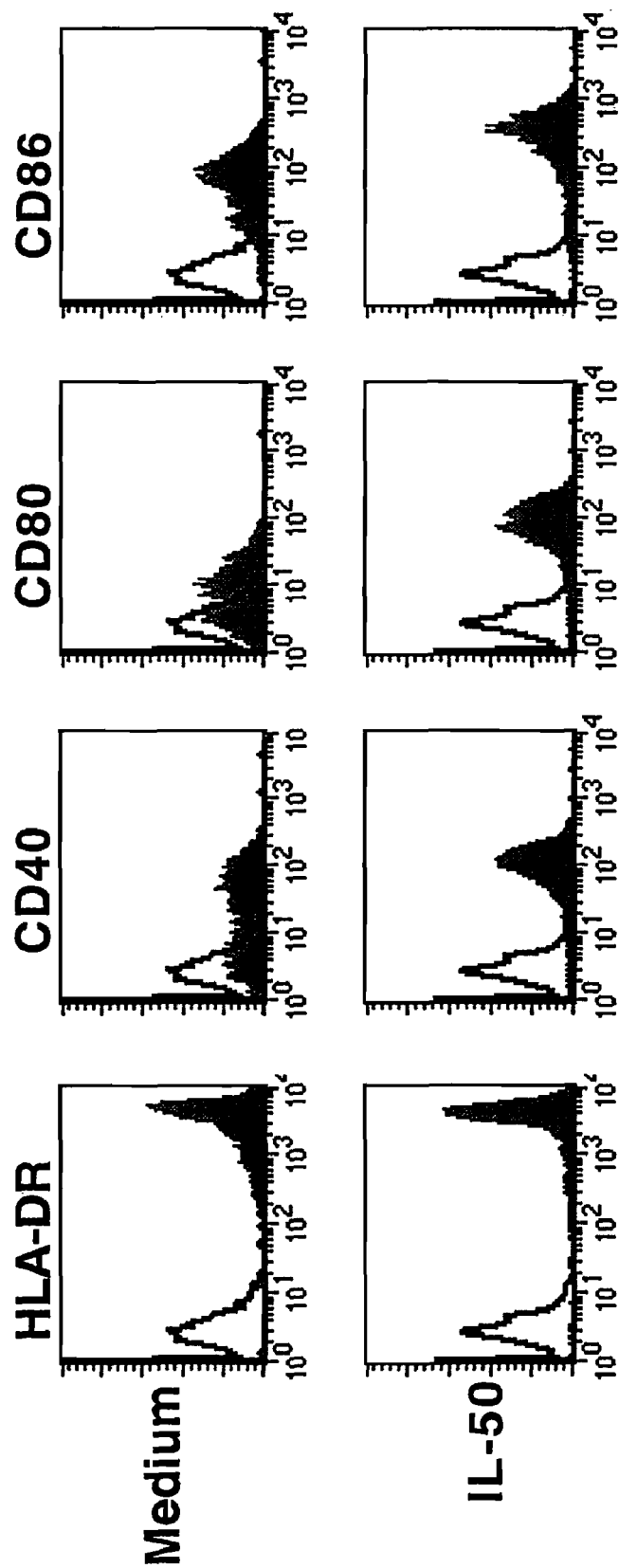
FIG. 7 shows the surface phenotype of CD11c+DC after 24 h of culture with and without (medium alone) IL-B50 and shows the upregulation of HLA-DR, as well as the costimulatory molecules CD40, CD80 and CD86. Results shown are from one representative of four independent experiments.
Figure 8A:
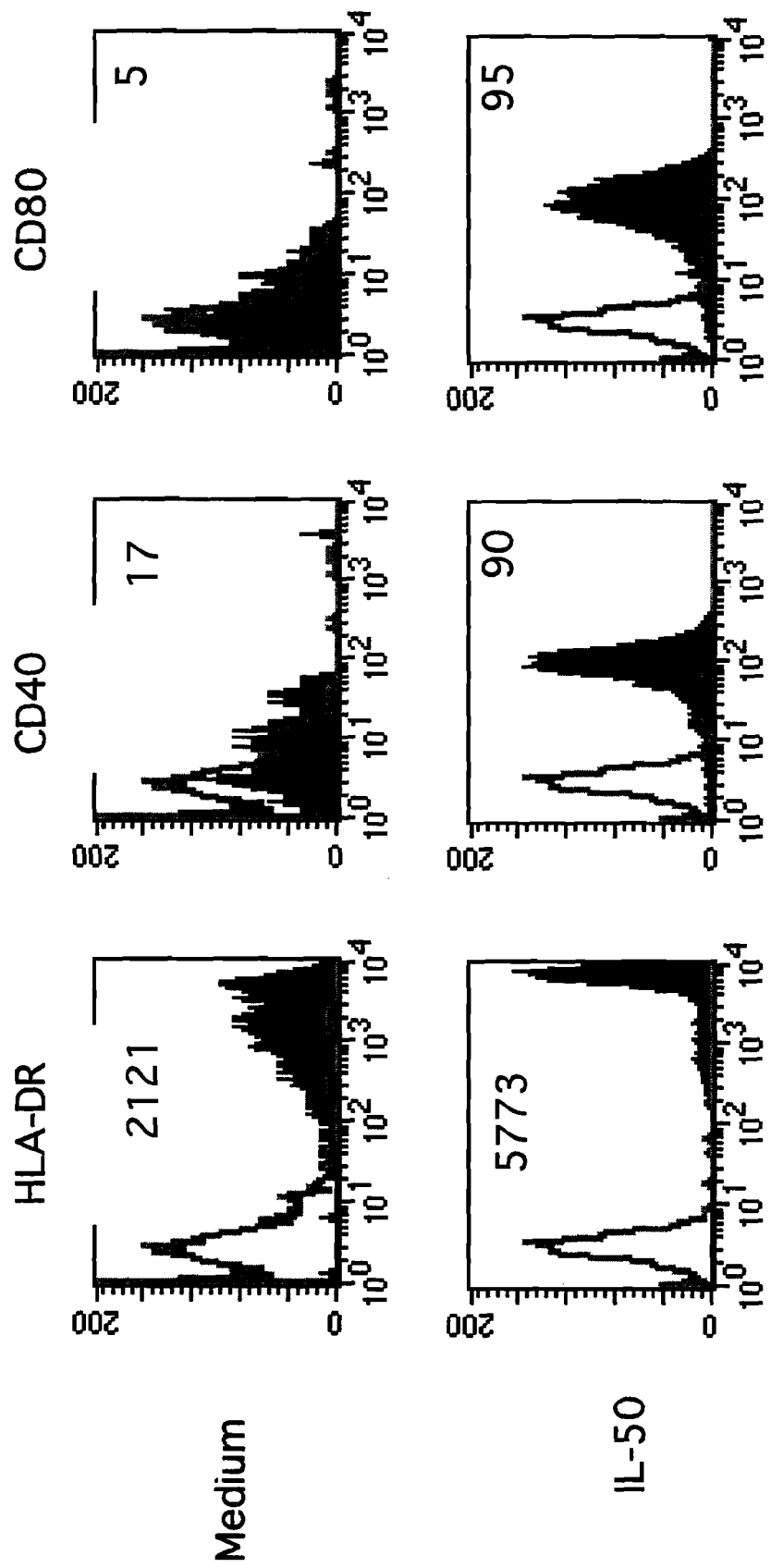
FIGS. 8A-8C show the surface phenotype of DC after treatment with medium alone, IL-B50, CD40-ligand (CD40L), IL-7 and LPS. IL-B50 is more potent than CD40-ligand and IL-7 in upregulating costimulatory molecules CD40 and CD80.
Figure 8B:
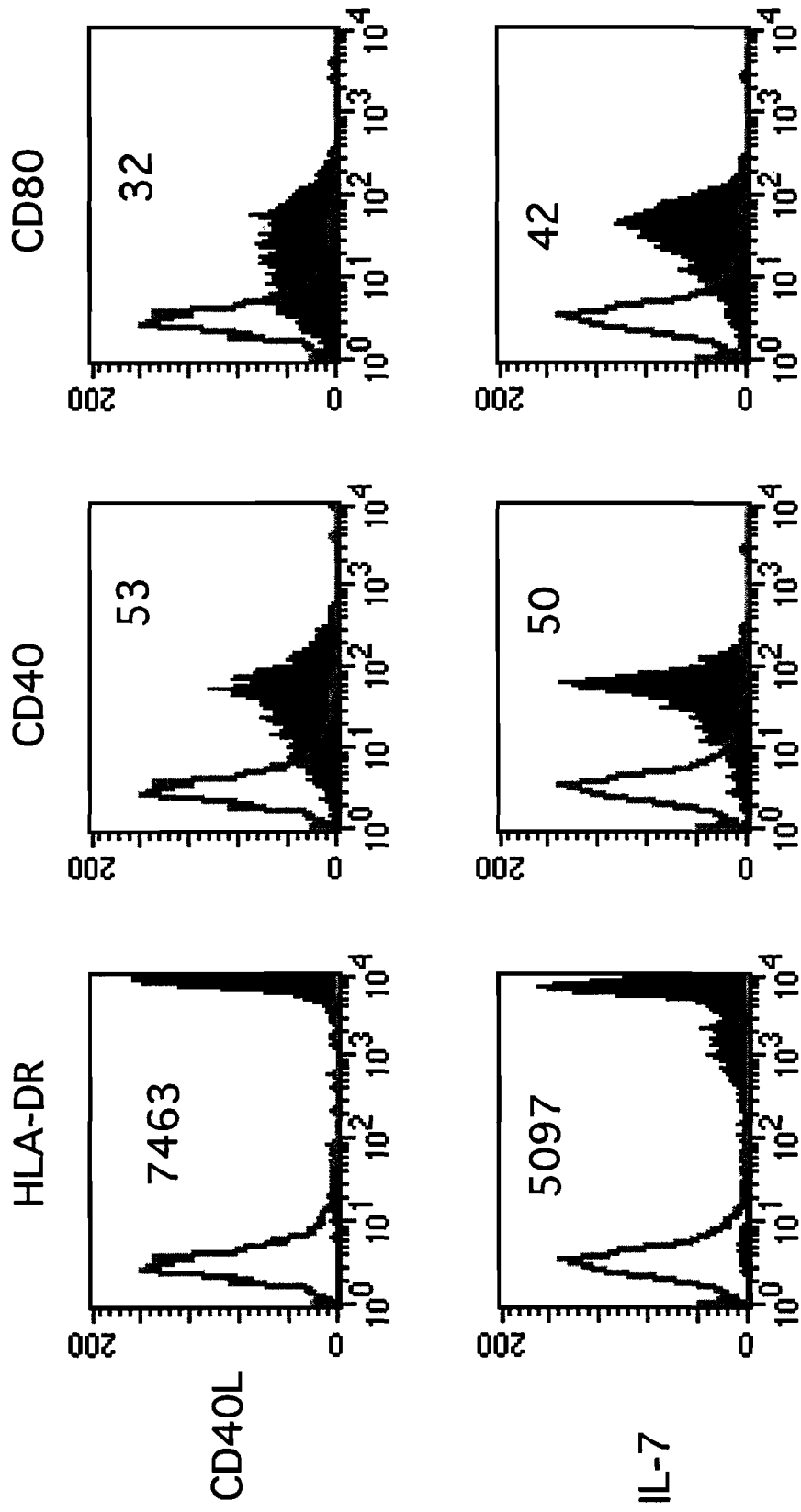
Figure 8C:
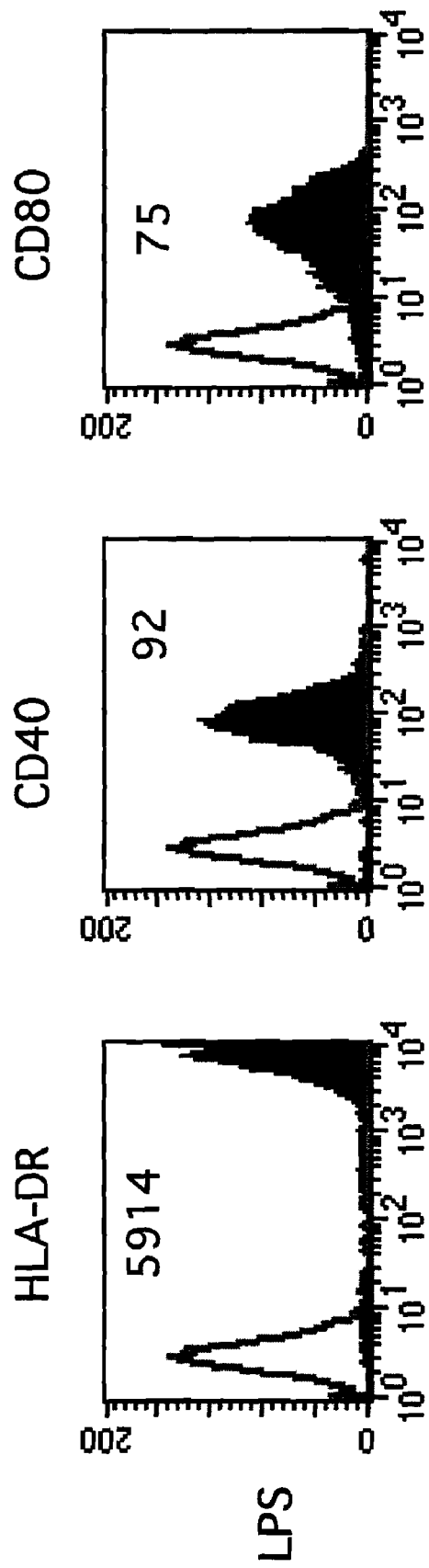

Freshly purified immature CD11c+blood DC are known to spontaneously mature in culture. As shown in FIG. 6A, loose and irregular clumps in the DC culture were evident after 24 hrs in medium alone. In the presence of IL-B50, this maturation process was dramatically enhanced. DC in culture formed tight and round clumps with fine dendrites visible at the periphery of each clump (FIG. 6B). The IL-B50-induced maturation was confirmed by analyzing the surface phenotype of DC using flow cytometry. Whereas IL-B50 slightly upregulated the expression of HLA-DR and CD86, it strongly induced the costimulatory molecules CD40 and CD80 (FIG. 7). This maturation process was accompanied by an increased viability of the DC. Additionally, IL-B50 was more potent than CD40-ligand (CD40L) and IL-7 in upregulating CD40 and CD80 (FIGS. 8A-8C). A titration of IL-B50 using log dilutions of the cytokine showed that both the effect on survival and the induction of costimulatory molecules on DC was maximal at 15 ng/ml and above, and still significant at concentrations as low as 15 pg/ml.

Figure 9:
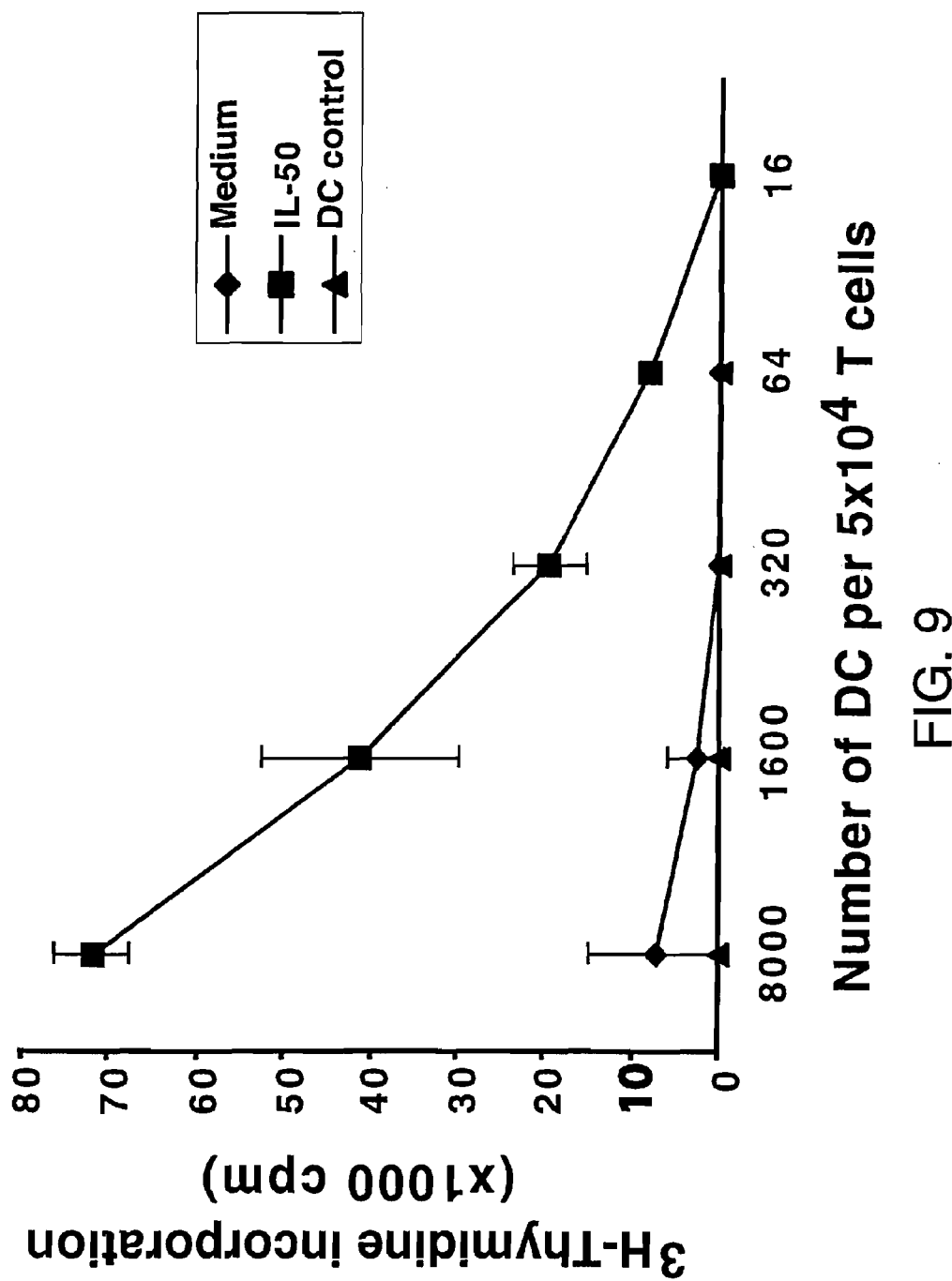
FIG. 9 shows the results of a T cell proliferation assay using CD11c+DC matured for 24 h in medium or with IL-B50 (15 ng/ml) and cocultured with $5 \times 10^4$ allogenic CD4+CD45RA+ naïve T cells at increasing DC/T cell ratios. Proliferation was assessed on day 6 by measuring [$^3$H]thymidine incorporation. Each point represents the mean [$^3$H]thymidine incorporation of triplicate cocultures. Vertical bars indicate the SD. DC alone (□) were used as a control and did not significantly proliferate. Results shown are from one representative of the two independent experiments.

The T cell stimulatory capacity of CD11+DC, cultured 24 hrs in medium alone or in the presence of IL-B50, was analyzed. DCs were cocultured with $5 \times 10^4$ naïve CD4+ CD45RA+allogeneic T cells at increasing DC/T cell ratios. As assessed by $^3$H-thymidine incorporation at day 5 of the coculture, DC cultured with IL-B50 induced up to 10-fold stronger naïve T cell proliferation as compared to DC cultured in medium (FIG. 9).

Figure 10:
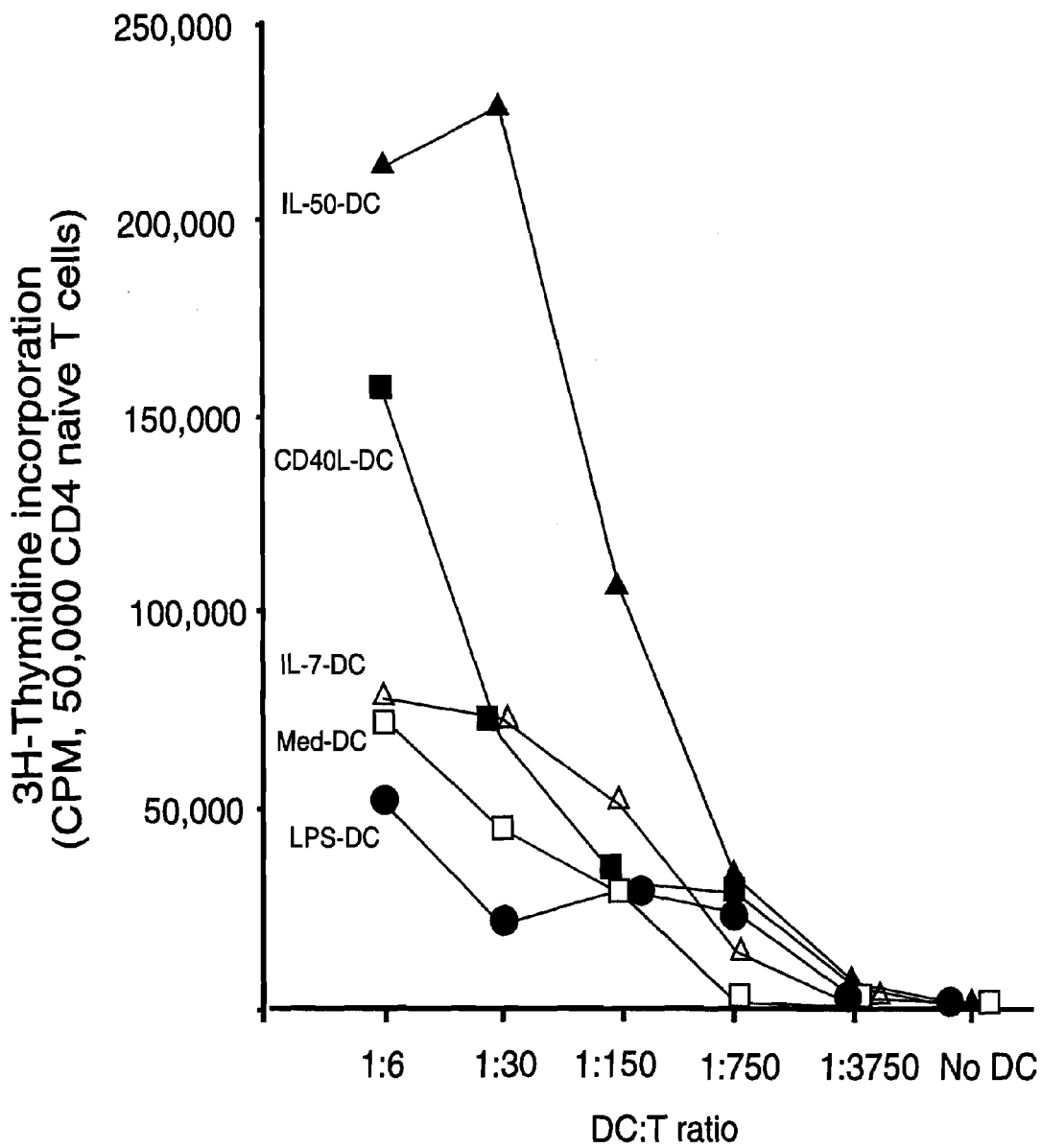
FIG. 10 shows the results of a similar experiment as described for FIG. 9, using DC matured in medium, IL-B50, CD40-ligand (CD40L), IL-7 and LPS.
Figure 11A:
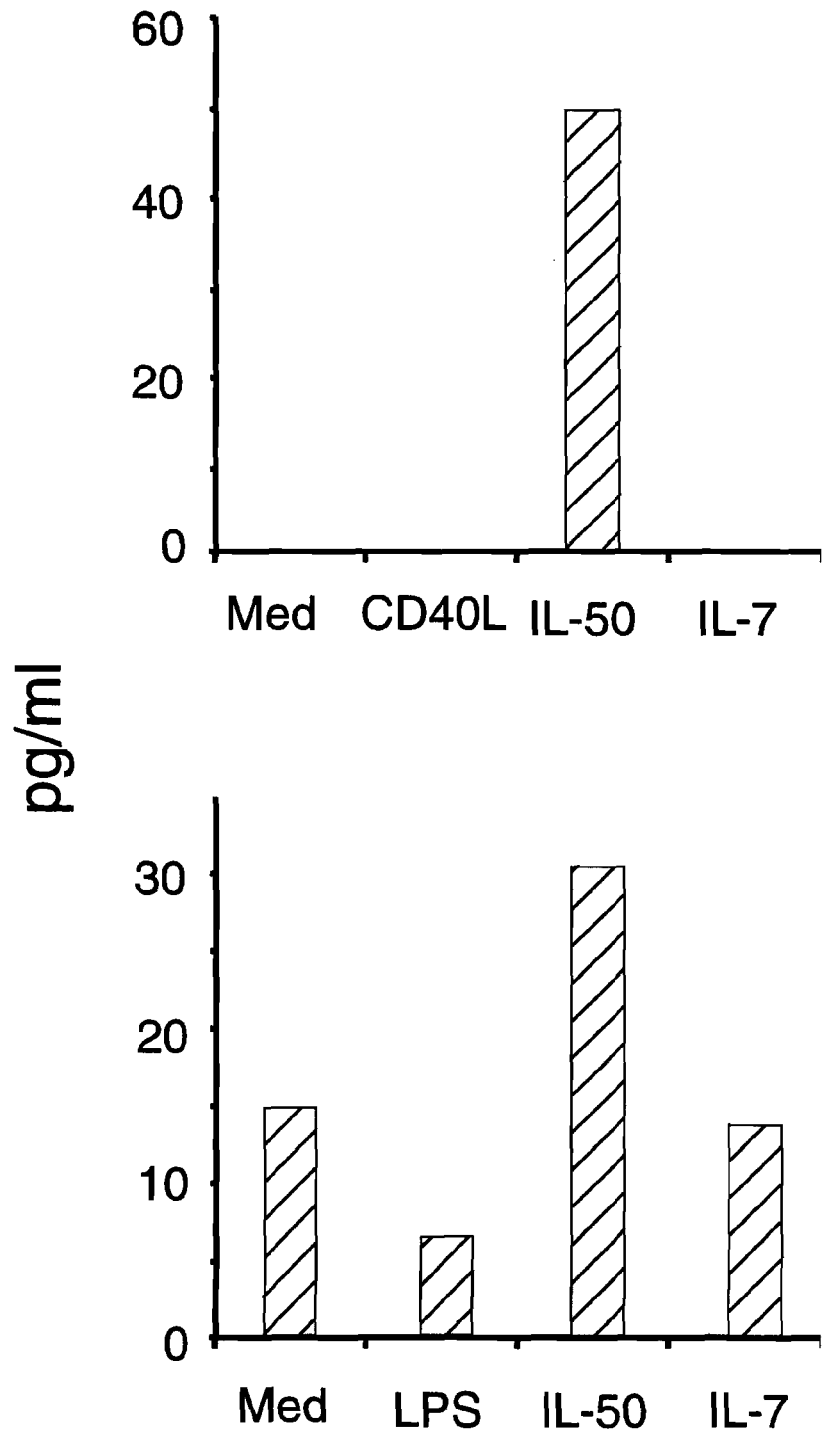
FIGS. 11A-11E show the production of various cytokines (expressed as pg/ml) by naïve CD4 T cells cocultured with DC matured in medium alone, IL-B50, CD40-ligand (CD40L), IL-7 and LPS.
Figure 11B:
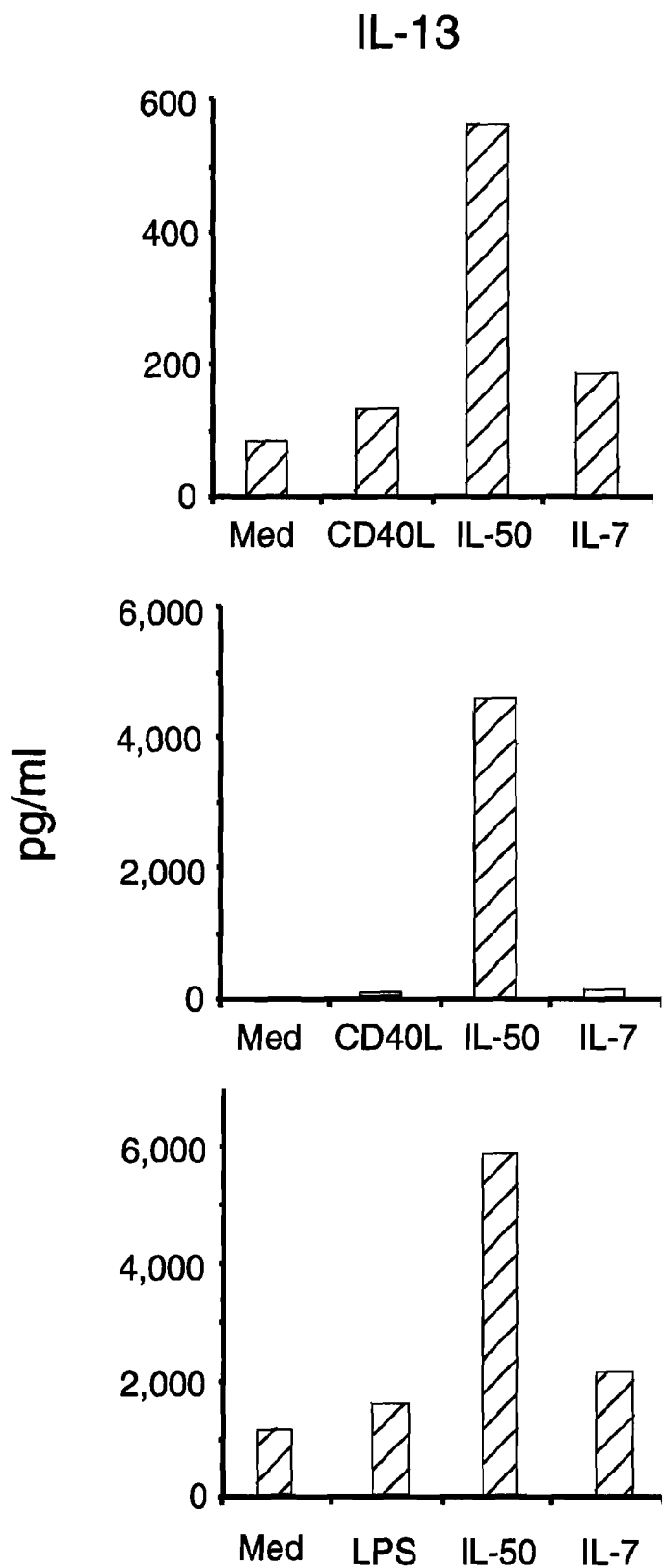
Figure 11C:
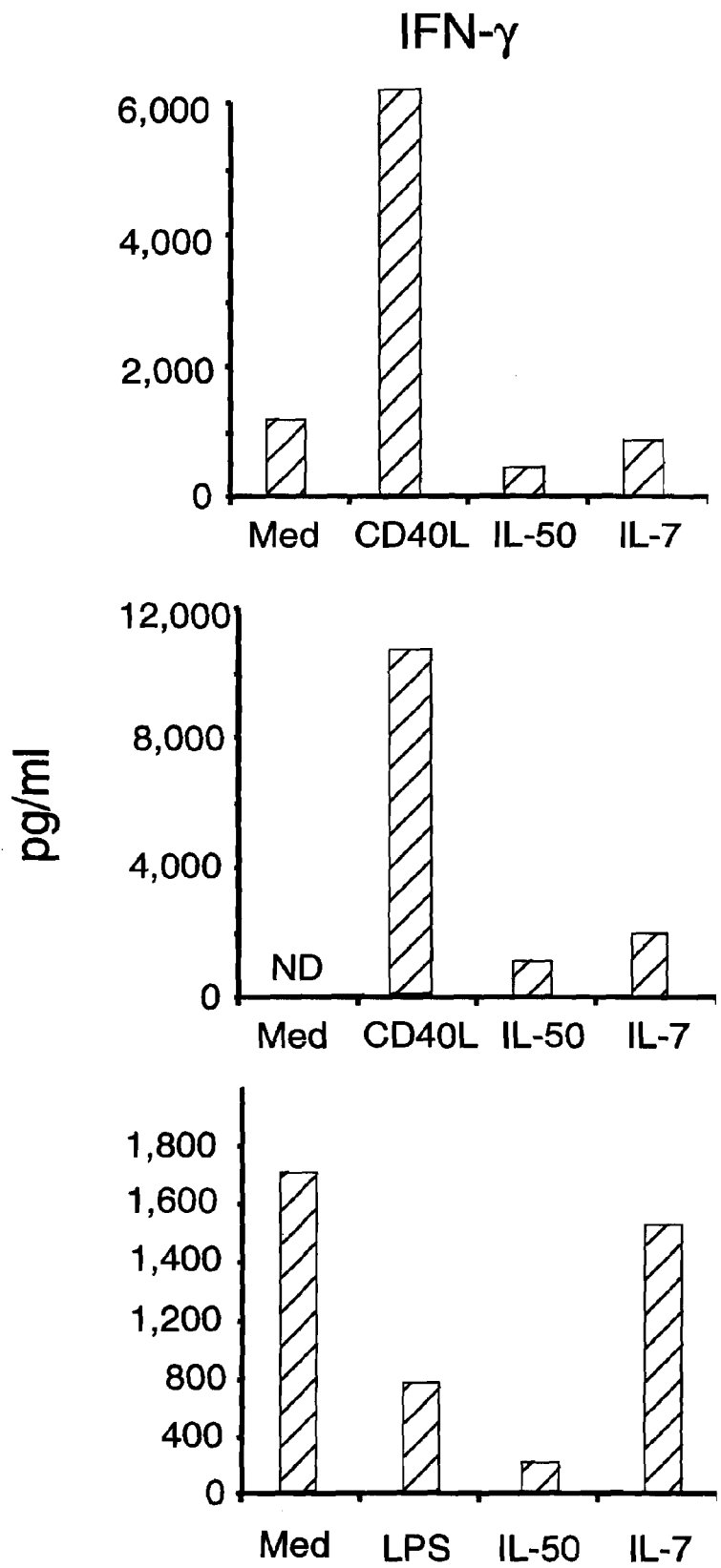
Figure 11D:
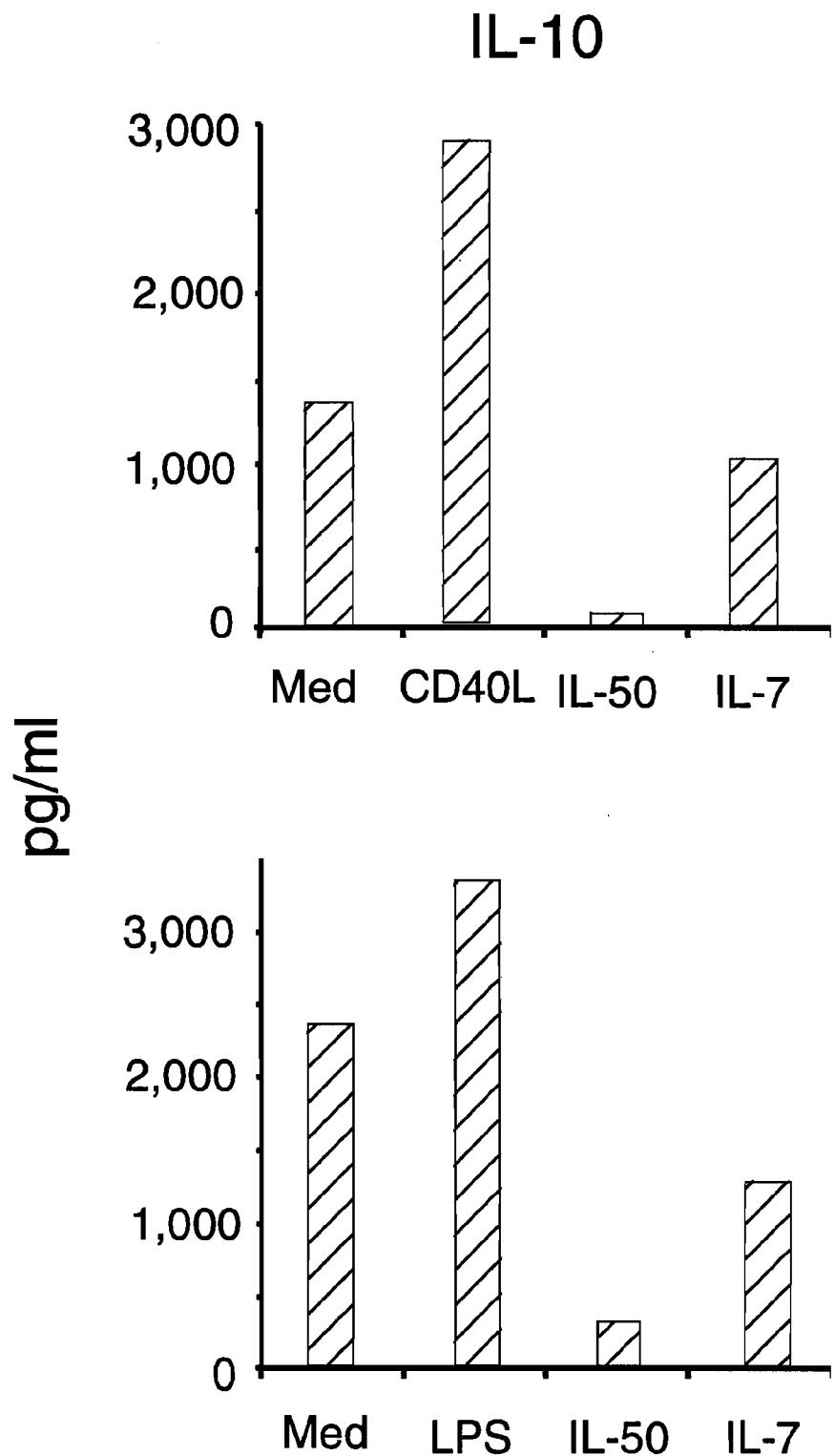
Figure 11E:
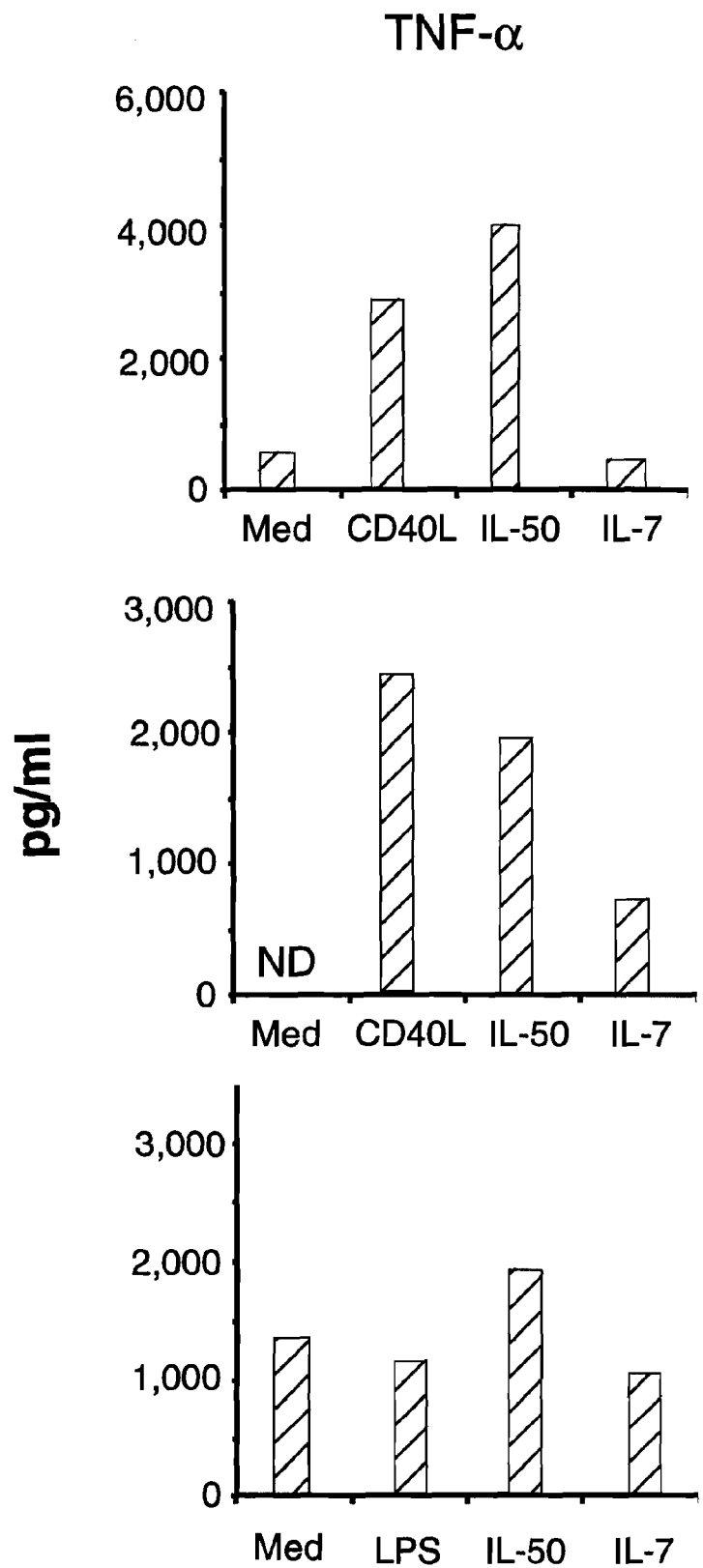

Additionally, the T cell stimulatory capacity of CD11+DC, cultured with LPS, medium alone, IL-7, CD40-ligand and IL-B50, was compared by determining $^3$H-thymidine incorporation. As shown in FIG. 10, IL-B50-activated DCs were more potent than DCs activated with CD40-ligand, IL-7 and LPS in inducing proliferation of allogeneic naïve CD4 T cells.

DCs, cultured in medium alone, IL-B50, CD40-ligand, IL-7 and LPS, were cocultured with naïve CD4 T cells. After 6 days of coculture, CD4 T cells were restimulated for 24 hours with anti-CD3 and anti-CD28 and the culture supernatants were analyzed by ELISA to quantify the cytokine production by T cells. As shown in FIGS. 11A-11E, IL-B50-activated human DCs primed naïve CD4 T cells to produce IL-4, IL-13 and TNF-α, but inhibited production of IL-10 and IFN-γ.

Figure 12:
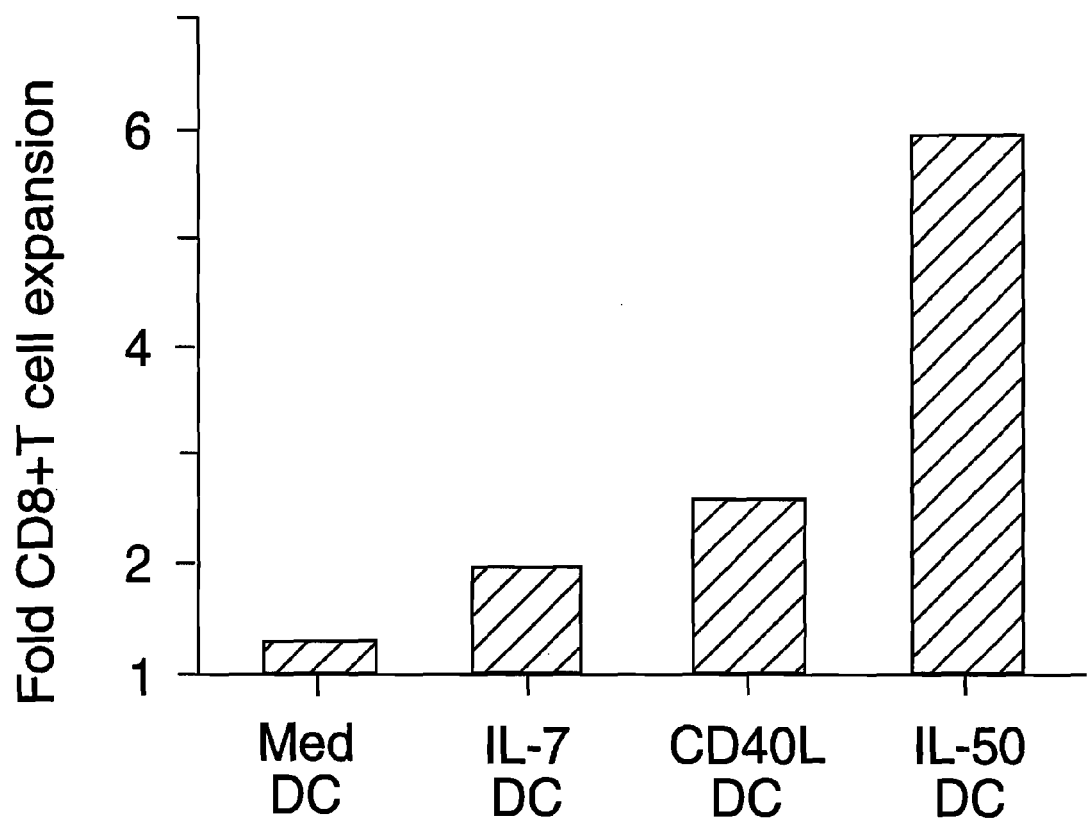
FIG. 12 shows the effect of DCs treated with medium alone, IL-B50, IL-7, and CD40-ligand on CD8 T cell expansion.
Figure 13:
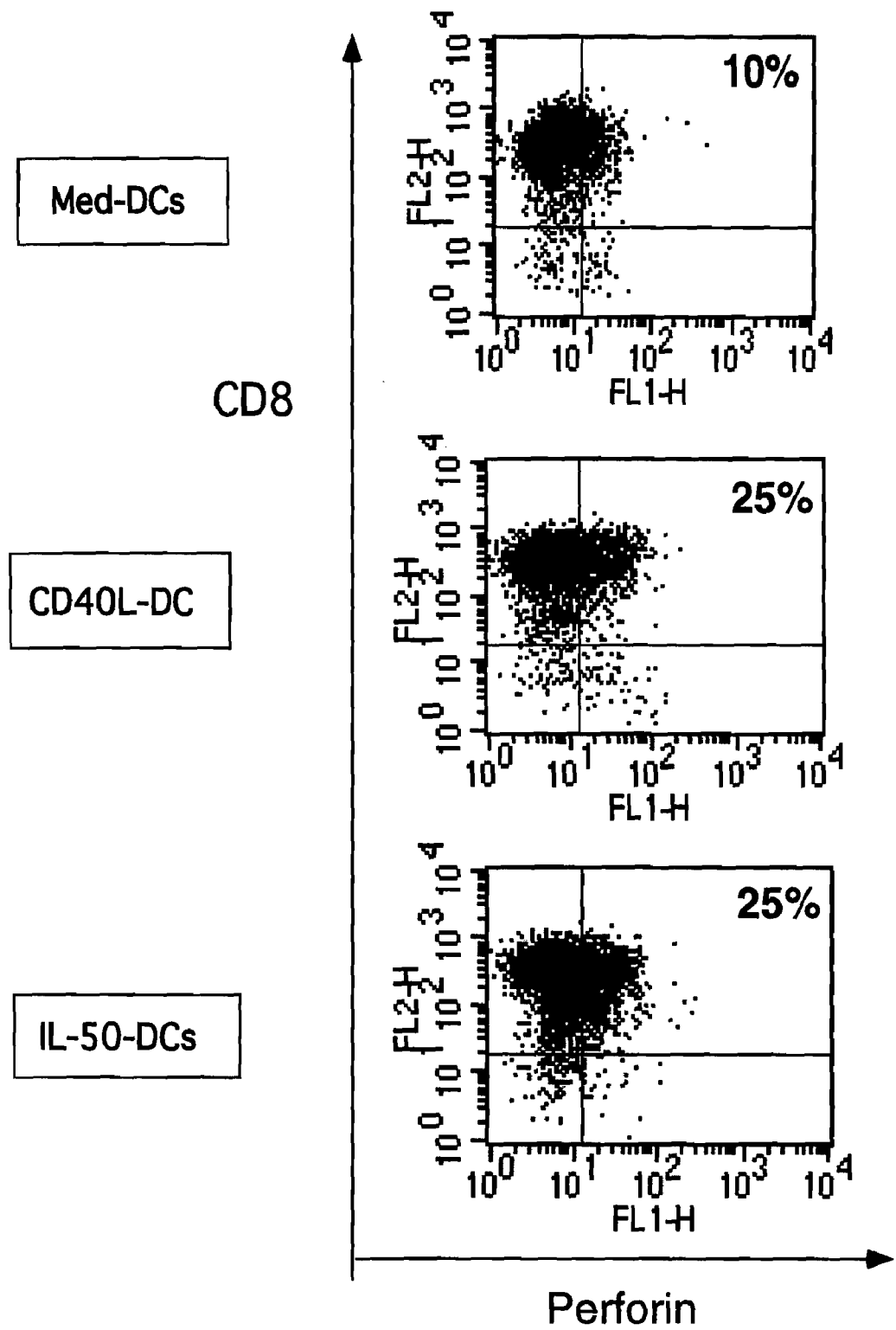
FIG. 13 compares expression of perforin by human naïve CD8 T cells induced by DCs treated with medium alone, IL-B50 or CD40-ligand.

DCs were cultured for 24 hours in medium alone, IL-B50, IL-7, CD40-ligand or LPS, to prime purified naïve CD8 T cells over 6 days in coculture. IL-B50-activated DCs strongly induced expansion of allogeneic naïve CD8 T cells (FIG. 12), as well as the expression of perforin (FIG. 13).

The data herein indicate, among other things, that human IL-B50 is a novel hematopoietic cytokine most closely related to IL-7. It represents a human ortholog of mTSLP. The human IL-B50 signaling makes use of the combination of hIL-7Rα and hRδ2, which together form a novel hematopoietic cytokine receptor. Both receptor subunits are notably present on macrophages and dendritic cells, indicating functional effects of the cytokine on those cell types, and mediating functions provided by those cell types. The human IL-B50 also promotes the phosphorylation of STAT3 and STAT5 transcription factors.

Therapeutic uses of IL-B50 are apparent. For example, SCID patients with mutations in IL-7Rα are T-cell deficient. Since IL-B50 uses IL-7Rα, IL-B50 share signaling pathway components, and may play a significant role in human T-cell differentiation and may enhance T-cell recovery in circumstances of T-cell depletion.

Likewise, IL-B50 antagonists are useful. The antagonists take various forms such as ligand muteins, antibodies to ligand, and antibodies to receptor, e.g., which block ligand binding. Since the hIL-B50 likely plays a role in the development of T- and B-cell lymphomas, then blocking IL-B50 signaling, either at the ligand or at its receptor components, is useful in treatment of some of these lymphomas.

Herein, based upon the binding studies, hIL-B50 receptor subunit mapping identified IL-7Rα and novel human receptor Rδ2 (a close relative of human γc or IL-2Rγ) as signaling receptor complex (co-expression in Ba/F3 cells delivers a proliferative signal in response to IL-B50). Receptor expression profiles indicate both IL-7Rα and Rδ2 are primarily expressed on dendritic cells, though they are both also expressed in monocytes. The dendritic cell expression indicates a role for the cytokine in maturation of cells or pathways important in antigen presentation, indicating use of the cytokine for expansion, e.g., ex vivo, of antigen presenting cells.

All citations herein are incorporated herein by reference to the same extent as if each individual publication or patent application was specifically and individually indicated to be incorporated by reference including all figures and drawings.

Many modifications and variations of this invention, as will be apparent to one of ordinary skill in the art can be made to adapt to a particular situation, material, composition of matter, process, process step or steps, to preserve the objective, spirit and scope of the invention. All such modifications are intended to be within the scope of the claims appended hereto without departing from the spirit and scope of the invention. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method for treating allergic disease comprising administering to a patient in need thereof an antagonistic antibody or a fragment thereof that specifically binds to a polypeptide consisting of the amino acid sequence set forth in SEQ ID NO:6 in an amount sufficient to inhibit an activity selected from the group consisting of:

i. dendritic cell production of TARC, PARC or MDC; and ii. up-regulation of a co-stimulatory or adhesion molecule on a dendritic cell, wherein said molecule is selected from the group consisting of HLA-DR, CD40, CD80, CD86, CD11a, CD18 and CD83, wherein the allergic disease is thereby treated.

2. The method of claim 1, wherein the activity that is inhibited is dendritic cell production of TARC, PARC or MDC.

3. The method of claim 1, wherein the activity that is inhibited is up-regulation of HLA-DR, CD40, CD80, CD86, CD11a, CD18 and CD83.

4. The method of claim 1, wherein the activity that is inhibited is up-regulation of HLA-DR, CD40 and CD80.

* * * * *

SEQUENCE LISTING

```
<160> NUMBER OF SEQ ID NOS: 6

<210> SEQ ID NO 1
<211> LENGTH: 1658
<212> TYPE: DNA
<213> ORGANISM: Homo sapiens
<220> FEATURE:
<221> NAME/KEY: CDS
<222> LOCATION: (23)..(1399)
<223> OTHER INFORMATION:

<400> SEQUENCE: 1
ctctctctct atctctctca ga atg aca att cta ggt aca act ttt ggc atg         52
                        Met Thr Ile Leu Gly Thr Thr Phe Gly Met
                         1               5                  10 gtt ttt tct tta ctt caa gtc gtt tct gga gaa agt ggc tat gct caa         100
Val Phe Ser Leu Leu Gln Val Val Ser Gly Glu Ser Gly Tyr Ala Gln
              15                  20                  25 aat gga gac ttg gaa gat gca gaa ctg gat gac tac tca ttc tca tgc         148
Asn Gly Asp Leu Glu Asp Ala Glu Leu Asp Asp Tyr Ser Phe Ser Cys
         30                  35                  40 tat agc cag ttg gaa gtg aat gga tcg cag cat tca ctg acc tgt gct         196
Tyr Ser Gln Leu Glu Val Asn Gly Ser Gln His Ser Leu Thr Cys Ala
     45                  50                  55 ttt gag gac cca gat gtc aac acc acc aat ctg gaa ttt gaa ata tgt         244
Phe Glu Asp Pro Asp Val Asn Thr Thr Asn Leu Glu Phe Glu Ile Cys
 60                  65                  70 ggg gcc ctc gtg gag gta aag tgc ctg aat ttc agg aaa cta caa gag         292
Gly Ala Leu Val Glu Val Lys Cys Leu Asn Phe Arg Lys Leu Gln Glu
 75                  80                  85                  90 ata tat ttc atc gag aca aag aaa ttc tta ctg att gga aag agc aat         340
Ile Tyr Phe Ile Glu Thr Lys Lys Phe Leu Leu Ile Gly Lys Ser Asn
                 95                 100                 105 ata tgt gtg aag gtt gga gaa aag agt cta acc tgc aaa aaa ata gac         388
Ile Cys Val Lys Val Gly Glu Lys Ser Leu Thr Cys Lys Lys Ile Asp
             110                 115                 120 cta acc act ata gtt aaa cct gag gct cct ttt gac ctg agt gtc atc         436
Leu Thr Thr Ile Val Lys Pro Glu Ala Pro Phe Asp Leu Ser Val Ile
         125                 130                 135 tat cgg gaa gga gcc aat gac ttt gtg gtg aca ttt aat aca tca cac         484
Tyr Arg Glu Gly Ala Asn Asp Phe Val Val Thr Phe Asn Thr Ser His
     140                 145                 150 ttg caa aag aag tat gta aaa gtt tta atg cat gat gta gct tac cgc         532
Leu Gln Lys Lys Tyr Val Lys Val Leu Met His Asp Val Ala Tyr Arg
155                 160                 165                 170
```

```
cag gaa aag gat gaa aac aaa tgg acg cat gtg aat tta tcc agc aca        580
Gln Glu Lys Asp Glu Asn Lys Trp Thr His Val Asn Leu Ser Ser Thr
                175                 180                 185 aag ctg aca ctc ctg cag aga aag ctc caa ccg gca gca atg tat gag        628
Lys Leu Thr Leu Leu Gln Arg Lys Leu Gln Pro Ala Ala Met Tyr Glu
                190                 195                 200 att aaa gtt cga tcc atc cct gat cac tat ttt aaa ggc ttc tgg agt        676
Ile Lys Val Arg Ser Ile Pro Asp His Tyr Phe Lys Gly Phe Trp Ser
            205                 210                 215 gaa tgg agt cca agt tat tac ttc aga act cca gag atc aat aat agc        724
Glu Trp Ser Pro Ser Tyr Tyr Phe Arg Thr Pro Glu Ile Asn Asn Ser
        220                 225                 230 tca ggg gag atg gat cct atc tta cta acc atc agc att ttg agt ttt        772
Ser Gly Glu Met Asp Pro Ile Leu Leu Thr Ile Ser Ile Leu Ser Phe
235                 240                 245                 250 ttc tct gtc gct ctg ttg gtc atc ttg gcc tgt gtg tta tgg aaa aaa        820
Phe Ser Val Ala Leu Leu Val Ile Leu Ala Cys Val Leu Trp Lys Lys
                255                 260                 265 agg att aag cct atc gta tgg ccc agt ctc ccc gat cat aag aag act        868
Arg Ile Lys Pro Ile Val Trp Pro Ser Leu Pro Asp His Lys Lys Thr
                270                 275                 280 ctg gaa cat ctt tgt aag aaa cca aga aaa aat tta aat gtg agt ttc        916
Leu Glu His Leu Cys Lys Lys Pro Arg Lys Asn Leu Asn Val Ser Phe
            285                 290                 295 aat cct gaa agt ttc ctg gac tgc cag att cat agg gtg gat gac att        964
Asn Pro Glu Ser Phe Leu Asp Cys Gln Ile His Arg Val Asp Asp Ile
        300                 305                 310 caa gct aga gat gaa gtg gaa ggt ttt ctg caa gat acg ttt cct cag       1012
Gln Ala Arg Asp Glu Val Glu Gly Phe Leu Gln Asp Thr Phe Pro Gln
315                 320                 325                 330 caa cta gaa gaa tct gag aag cag agg ctt gga ggg gat gtg cag agc       1060
Gln Leu Glu Glu Ser Glu Lys Gln Arg Leu Gly Gly Asp Val Gln Ser
                335                 340                 345 ccc aac tgc cca tct gag gat gta gtc gtc act cca gaa agc ttt gga       1108
Pro Asn Cys Pro Ser Glu Asp Val Val Val Thr Pro Glu Ser Phe Gly
                350                 355                 360 aga gat tca tcc ctc aca tgc ctg gct ggg aat gtc agt gca tgt gac       1156
Arg Asp Ser Ser Leu Thr Cys Leu Ala Gly Asn Val Ser Ala Cys Asp
            365                 370                 375 gcc cct att ctc tcc tct tcc agg tcc cta gac tgc agg gag agt ggc       1204
Ala Pro Ile Leu Ser Ser Ser Arg Ser Leu Asp Cys Arg Glu Ser Gly
        380                 385                 390 aag aat ggg cct cat gtg tac cag gac ctc ctg ctt agc ctt ggg act       1252
Lys Asn Gly Pro His Val Tyr Gln Asp Leu Leu Leu Ser Leu Gly Thr
395                 400                 405                 410 aca aac agc acg ctg ccc cct cca ttt tct ctc caa tct gga atc ctg       1300
Thr Asn Ser Thr Leu Pro Pro Pro Phe Ser Leu Gln Ser Gly Ile Leu
                415                 420                 425 aca ttg aac cca gtt gct cag ggt cag ccc att ctt act tcc ctg gga       1348
Thr Leu Asn Pro Val Ala Gln Gly Gln Pro Ile Leu Thr Ser Leu Gly
                430                 435                 440 tca aat caa gaa gaa gca tat gtc acc atg tcc agc ttc tac caa aac       1396
Ser Asn Gln Glu Glu Ala Tyr Val Thr Met Ser Ser Phe Tyr Gln Asn
            445                 450                 455 cag tgaagtgtaa gaaacccaga ctgaacttac cgtgagcgac aaagatgatt           1449
Gln taaaagggaa gtctagagtt cctagtctcc ctcacagcac agagaagaca aaattagcaa    1509
aaccccacta cacagtctgc aagattctga aacattgctt tgaccactct tcctgagttc    1569
```

```
agtggcactc aacatgagtc aagagcatcc tgcttctacc atgtggattt ggtcacaagg    1629
tttaaggtga cccaatgatt cagctattt                                      1658
```

<210> SEQ ID NO 2
<211> LENGTH: 459
<212> TYPE: PRT
<213> ORGANISM: Homo sapiens

<400> SEQUENCE: 2

```
Met Thr Ile Leu Gly Thr Thr Phe Gly Met Val Phe Ser Leu Leu Gln
 1               5                  10                  15

Val Val Ser Gly Glu Ser Gly Tyr Ala Gln Asn Gly Asp Leu Glu Asp
                20                  25                  30

Ala Glu Leu Asp Asp Tyr Ser Phe Ser Cys Tyr Ser Gln Leu Glu Val
            35                  40                  45

Asn Gly Ser Gln His Ser Leu Thr Cys Ala Phe Glu Asp Pro Asp Val
        50                  55                  60

Asn Thr Thr Asn Leu Glu Phe Glu Ile Cys Gly Ala Leu Val Glu Val
65                  70                  75                  80

Lys Cys Leu Asn Phe Arg Lys Leu Gln Glu Ile Tyr Phe Ile Glu Thr
                85                  90                  95

Lys Lys Phe Leu Leu Ile Gly Lys Ser Asn Ile Cys Val Lys Val Gly
            100                 105                 110

Glu Lys Ser Leu Thr Cys Lys Lys Ile Asp Leu Thr Thr Ile Val Lys
        115                 120                 125

Pro Glu Ala Pro Phe Asp Leu Ser Val Ile Tyr Arg Glu Gly Ala Asn
    130                 135                 140

Asp Phe Val Val Thr Phe Asn Thr Ser His Leu Gln Lys Lys Tyr Val
145                 150                 155                 160

Lys Val Leu Met His Asp Val Ala Tyr Arg Gln Glu Lys Asp Glu Asn
                165                 170                 175

Lys Trp Thr His Val Asn Leu Ser Ser Thr Lys Leu Thr Leu Leu Gln
            180                 185                 190

Arg Lys Leu Gln Pro Ala Ala Met Tyr Glu Ile Lys Val Arg Ser Ile
        195                 200                 205

Pro Asp His Tyr Phe Lys Gly Phe Trp Ser Glu Trp Ser Pro Ser Tyr
    210                 215                 220

Tyr Phe Arg Thr Pro Glu Ile Asn Asn Ser Ser Gly Glu Met Asp Pro
225                 230                 235                 240

Ile Leu Leu Thr Ile Ser Ile Leu Ser Phe Phe Ser Val Ala Leu Leu
                245                 250                 255

Val Ile Leu Ala Cys Val Leu Trp Lys Lys Arg Ile Lys Pro Ile Val
            260                 265                 270

Trp Pro Ser Leu Pro Asp His Lys Lys Thr Leu Glu His Leu Cys Lys
        275                 280                 285

Lys Pro Arg Lys Asn Leu Asn Val Ser Phe Asn Pro Glu Ser Phe Leu
    290                 295                 300

Asp Cys Gln Ile His Arg Val Asp Asp Ile Gln Ala Arg Asp Glu Val
305                 310                 315                 320

Glu Gly Phe Leu Gln Asp Thr Phe Pro Gln Gln Leu Glu Glu Ser Glu
                325                 330                 335

Lys Gln Arg Leu Gly Gly Asp Val Gln Ser Pro Asn Cys Pro Ser Glu
            340                 345                 350

Asp Val Val Val Thr Pro Glu Ser Phe Gly Arg Asp Ser Ser Leu Thr
        355                 360                 365
```

```
Cys Leu Ala Gly Asn Val Ser Ala Cys Asp Ala Pro Ile Leu Ser Ser
    370                 375                 380

Ser Arg Ser Leu Asp Cys Arg Glu Ser Gly Lys Asn Gly Pro His Val
385                 390                 395                 400

Tyr Gln Asp Leu Leu Leu Ser Leu Gly Thr Thr Asn Ser Thr Leu Pro
                405                 410                 415

Pro Pro Phe Ser Leu Gln Ser Gly Ile Leu Thr Leu Asn Pro Val Ala
            420                 425                 430

Gln Gly Gln Pro Ile Leu Thr Ser Leu Gly Ser Asn Gln Glu Glu Ala
        435                 440                 445

Tyr Val Thr Met Ser Ser Phe Tyr Gln Asn Gln
    450                 455

<210> SEQ ID NO 3
<211> LENGTH: 1557
<212> TYPE: DNA
<213> ORGANISM: Homo sapiens
<220> FEATURE:
<221> NAME/KEY: CDS
<222> LOCATION: (13)..(1125)
<223> OTHER INFORMATION:

<400> SEQUENCE: 3
cggcacgagg gc atg ggg cgg ctg gtt ctg ctg tgg gga gct gcc gtc ttt       51
          Met Gly Arg Leu Val Leu Leu Trp Gly Ala Ala Val Phe
          1               5                   10 ctg ctg gga ggc tgg atg gct ttg ggg caa gga gga gca gca gaa gga        99
Leu Leu Gly Gly Trp Met Ala Leu Gly Gln Gly Gly Ala Ala Glu Gly
    15                  20                  25 gta cag att cag atc atc tac ttc aat tta gaa acc gtg cag gtg aca       147
Val Gln Ile Gln Ile Ile Tyr Phe Asn Leu Glu Thr Val Gln Val Thr
30                  35                  40                  45 tgg aat gcc agc aaa tac tcc agg acc aac ctg act ttc cac tac aga       195
Trp Asn Ala Ser Lys Tyr Ser Arg Thr Asn Leu Thr Phe His Tyr Arg
                50                  55                  60 ttc aac ggt gat gag gcc tat gac cag tgc acc aac tac ctt ctc cag       243
Phe Asn Gly Asp Glu Ala Tyr Asp Gln Cys Thr Asn Tyr Leu Leu Gln
            65                  70                  75 gaa ggt cac act tcg ggg tgc ctc cta gac gca gag cag cga gac gac       291
Glu Gly His Thr Ser Gly Cys Leu Leu Asp Ala Glu Gln Arg Asp Asp
        80                  85                  90 att ctc tat ttc tcc atc agg aat ggg acg cac ccc gtt ttc acc gca       339
Ile Leu Tyr Phe Ser Ile Arg Asn Gly Thr His Pro Val Phe Thr Ala
    95                  100                 105 agt cgc tgg atg gtt tat tac ctg aaa ccc agt tcc ccg aag cac gtg       387
Ser Arg Trp Met Val Tyr Tyr Leu Lys Pro Ser Ser Pro Lys His Val
110                 115                 120                 125 aga ttt tcg tgg cat cag gat gca gtg acg gtg acg tgt tct gac ctg       435
Arg Phe Ser Trp His Gln Asp Ala Val Thr Val Thr Cys Ser Asp Leu
                130                 135                 140 tcc tac ggg gat ctc ctc tat gag gtt cag tac cgg agc ccc ttc gac       483
Ser Tyr Gly Asp Leu Leu Tyr Glu Val Gln Tyr Arg Ser Pro Phe Asp
            145                 150                 155 acc gag tgg cag tcc aaa cag gaa aat acc tgc aac gtc acc ata gaa       531
Thr Glu Trp Gln Ser Lys Gln Glu Asn Thr Cys Asn Val Thr Ile Glu
        160                 165                 170 ggc ttg gat gcc gag aag tgt tac tct ttc tgg gtc agg gtg aag gct       579
Gly Leu Asp Ala Glu Lys Cys Tyr Ser Phe Trp Val Arg Val Lys Ala
    175                 180                 185 atg gag gat gta tat ggg cca gac aca tac cca agc gac tgg tca gag       627
```

-continued

| | | |
|---|---|---|
| Met Glu Asp Val Tyr Gly Pro Asp Thr Tyr Pro Ser Asp Trp Ser Glu<br>190                       195                     200                  205 | |
| gtg aca tgc tgg cag aga ggc gag att cgg gat gcc tgt gca gag aca<br>Val Thr Cys Trp Gln Arg Gly Glu Ile Arg Asp Ala Cys Ala Glu Thr<br>                    210                           215                        220 | 675 |
| cca acg cct ccc aaa cca aag ctg tcc aaa ttt att tta att tcc agc<br>Pro Thr Pro Pro Lys Pro Lys Leu Ser Lys Phe Ile Leu Ile Ser Ser<br>          225                       230                       235 | 723 |
| ctg gcc atc ctt ctg atg gtg tct ctc ctt ctg tct tta tgg aaa<br>Leu Ala Ile Leu Leu Met Val Ser Leu Leu Leu Leu Ser Leu Trp Lys<br>240                       245                     250 | 771 |
| tta tgg aga gtg aag aag ttt ctc att ccc agc gtg cca gac ccg aaa<br>Leu Trp Arg Val Lys Lys Phe Leu Ile Pro Ser Val Pro Asp Pro Lys<br>          255                       260                       265 | 819 |
| tcc atc ttc ccc ggg ctc ttt gag ata cac caa ggg aac ttc cag gag<br>Ser Ile Phe Pro Gly Leu Phe Glu Ile His Gln Gly Asn Phe Gln Glu<br>270                       275                     280                     285 | 867 |
| tgg atc aca gac acc cag aac gtg gcc cac ctc cac aag atg gca ggt<br>Trp Ile Thr Asp Thr Gln Asn Val Ala His Leu His Lys Met Ala Gly<br>                    290                         295                       300 | 915 |
| gca gag caa gaa agt ggc ccc gag gag ccc ctg gta gtc cag ttg gcc<br>Ala Glu Gln Glu Ser Gly Pro Glu Glu Pro Leu Val Val Gln Leu Ala<br>305                       310                     315 | 963 |
| aag act gaa gcc gag tct ccc agg atg ctg gac cca cag acc gag gag<br>Lys Thr Glu Ala Glu Ser Pro Arg Met Leu Asp Pro Gln Thr Glu Glu<br>          320                       325                      330 | 1011 |
| aaa gag gcc tct ggg gga tcc ctc cag ctt ccc cac cag ccc ctc caa<br>Lys Glu Ala Ser Gly Gly Ser Leu Gln Leu Pro His Gln Pro Leu Gln<br>335                       340                     345 | 1059 |
| ggc ggt gat gtg gtc aca atc ggg ggc ttc acc ttt gtg atg aat gac<br>Gly Gly Asp Val Val Thr Ile Gly Gly Phe Thr Phe Val Met Asn Asp<br>350                       355                     360                   365 | 1107 |
| cgc tcc tac gtg gcg ttg tgatggacac accactgtca aagtcaacgt<br>Arg Ser Tyr Val Ala Leu<br>                    370 | 1155 |
| caggatccac gttgacattt aaagacagag gggactgtcc cggggactcc acaccaccat | 1215 |
| ggatgggaag tctccacgcc aatgatggta ggactaggag actctgaaga cccagcctca | 1275 |
| ccgcctaatg cggccactgc cctgctaact ttcccccaca tgagtctctg tgttcaaagg | 1335 |
| cttgatggca gatgggagcc aattgctcca ggagatttac tcccagttcc ttttcgtgcc | 1395 |
| tgaacgttgt cacataaacc ccaaggcagc acgtccaaaa tgctgtaaaa ccatcttccc | 1455 |
| actctgtgag tccccagttc cgtccatgta cctgttccat agcattggat tctcggagga | 1515 |
| ttttttgtct gttttgagac tccaaaccac ctctacccct ac | 1557 |

<210> SEQ ID NO 4
<211> LENGTH: 371
<212> TYPE: PRT
<213> ORGANISM: Homo sapiens

<400> SEQUENCE: 4

Met Gly Arg Leu Val Leu Leu Trp Gly Ala Ala Val Phe Leu Leu Gly
1                   5                       10                      15

Gly Trp Met Ala Leu Gly Gln Gly Gly Ala Ala Glu Gly Val Gln Ile
                 20                       25                       30

Gln Ile Ile Tyr Phe Asn Leu Glu Thr Val Gln Val Thr Trp Asn Ala
               35                      40                       45

Ser Lys Tyr Ser Arg Thr Asn Leu Thr Phe His Tyr Arg Phe Asn Gly
     50                       55                       60

-continued

```
Asp Glu Ala Tyr Asp Gln Cys Thr Asn Tyr Leu Leu Gln Glu Gly His
 65                  70                  75                  80

Thr Ser Gly Cys Leu Leu Asp Ala Glu Gln Arg Asp Ile Leu Tyr
             85                  90                  95

Phe Ser Ile Arg Asn Gly Thr His Pro Val Phe Thr Ala Ser Arg Trp
        100                 105                 110

Met Val Tyr Tyr Leu Lys Pro Ser Pro Lys His Val Arg Phe Ser
        115                 120                 125

Trp His Gln Asp Ala Val Thr Val Thr Cys Ser Asp Leu Ser Tyr Gly
    130                 135                 140

Asp Leu Leu Tyr Glu Val Gln Tyr Arg Ser Pro Phe Asp Thr Glu Trp
145                 150                 155                 160

Gln Ser Lys Gln Glu Asn Thr Cys Asn Val Thr Ile Glu Gly Leu Asp
                165                 170                 175

Ala Glu Lys Cys Tyr Ser Phe Trp Val Arg Val Lys Ala Met Glu Asp
            180                 185                 190

Val Tyr Gly Pro Asp Thr Tyr Pro Ser Asp Trp Ser Glu Val Thr Cys
        195                 200                 205

Trp Gln Arg Gly Glu Ile Arg Asp Ala Cys Ala Glu Thr Pro Thr Pro
    210                 215                 220

Pro Lys Pro Lys Leu Ser Lys Phe Ile Leu Ile Ser Ser Leu Ala Ile
225                 230                 235                 240

Leu Leu Met Val Ser Leu Leu Leu Ser Leu Trp Lys Leu Trp Arg
                245                 250                 255

Val Lys Lys Phe Leu Ile Pro Ser Val Pro Asp Pro Lys Ser Ile Phe
            260                 265                 270

Pro Gly Leu Phe Glu Ile His Gln Gly Asn Phe Gln Glu Trp Ile Thr
        275                 280                 285

Asp Thr Gln Asn Val Ala His Leu His Lys Met Ala Gly Ala Glu Gln
290                 295                 300

Glu Ser Gly Pro Glu Glu Pro Leu Val Val Gln Leu Ala Lys Thr Glu
305                 310                 315                 320

Ala Glu Ser Pro Arg Met Leu Asp Pro Gln Thr Glu Glu Lys Glu Ala
                325                 330                 335

Ser Gly Gly Ser Leu Gln Leu Pro His Gln Pro Leu Gln Gly Gly Asp
            340                 345                 350

Val Val Thr Ile Gly Gly Phe Thr Phe Val Met Asn Asp Arg Ser Tyr
        355                 360                 365

Val Ala Leu
    370

<210> SEQ ID NO 5
<211> LENGTH: 480
<212> TYPE: DNA
<213> ORGANISM: Homo sapiens
<220> FEATURE:
<221> NAME/KEY: CDS
<222> LOCATION: (1)..(477)
<223> OTHER INFORMATION:

<400> SEQUENCE: 5 atg ttc cct ttt gcc tta cta tat gtt ctg tca gtt tct ttc agg aaa      48
Met Phe Pro Phe Ala Leu Leu Tyr Val Leu Ser Val Ser Phe Arg Lys
  1               5                  10                  15 atc ttc atc tta caa ctt gta ggg ctg gtg tta act tac gac ttc act      96
Ile Phe Ile Leu Gln Leu Val Gly Leu Val Leu Thr Tyr Asp Phe Thr
             20                  25                  30
```

```
aac tgt gac ttt gag aag att aaa gca gcc tat ctc agt act att tct    144
Asn Cys Asp Phe Glu Lys Ile Lys Ala Ala Tyr Leu Ser Thr Ile Ser
        35                  40                  45 aaa gac ctg att aca tat atg agt ggg acc aaa agt acc gag ttc aac    192
Lys Asp Leu Ile Thr Tyr Met Ser Gly Thr Lys Ser Thr Glu Phe Asn
 50                  55                  60 aac acc gtc tct tgt agc aat cgg cca cat tgc ctt act gaa atc cag    240
Asn Thr Val Ser Cys Ser Asn Arg Pro His Cys Leu Thr Glu Ile Gln
 65                  70                  75                  80 agc cta acc ttc aat ccc acc gcc ggc tgc gcg tcg ctc gcc aaa gaa    288
Ser Leu Thr Phe Asn Pro Thr Ala Gly Cys Ala Ser Leu Ala Lys Glu
                 85                  90                  95 atg ttc gcc atg aaa act aag gct gcc tta gct atc tgg tgc cca ggc    336
Met Phe Ala Met Lys Thr Lys Ala Ala Leu Ala Ile Trp Cys Pro Gly
            100                 105                 110 tat tcg gaa act cag ata aat gct act cag gca atg aag aag agg aga    384
Tyr Ser Glu Thr Gln Ile Asn Ala Thr Gln Ala Met Lys Lys Arg Arg
        115                 120                 125 aaa agg aaa gtc aca acc aat aaa tgt ctg gaa caa gtg tca caa tta    432
Lys Arg Lys Val Thr Thr Asn Lys Cys Leu Glu Gln Val Ser Gln Leu
130                 135                 140 caa gga ttg tgg cgt cgc ttc aat cga cct tta ctg aaa caa cag taa    480
Gln Gly Leu Trp Arg Arg Phe Asn Arg Pro Leu Leu Lys Gln Gln
145                 150                 155

<210> SEQ ID NO 6
<211> LENGTH: 159
<212> TYPE: PRT
<213> ORGANISM: Homo sapiens

<400> SEQUENCE: 6

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
 50                  55                  60

Asn Thr Val Ser Cys Ser Asn Arg Pro His Cys Leu Thr Glu Ile Gln
 65                  70                  75                  80

Ser Leu Thr Phe Asn Pro Thr Ala Gly Cys Ala Ser Leu Ala Lys Glu
                 85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
130                 135                 140

Gln Gly Leu Trp Arg Arg Phe Asn Arg Pro Leu Leu Lys Gln Gln
145                 150                 155
```